(12) United States Patent
Boyer et al.

(10) Patent No.: US 8,637,553 B2
(45) Date of Patent: Jan. 28, 2014

(54) FLUORO SUBSTITUTED OMEGA-CARBOXYARYL DIPHENYL UREA FOR THE TREATMENT AND PREVENTION OF DISEASES AND CONDITIONS

(75) Inventors: Stephen Boyer, Hilden (DE); Jacques Dumas, Bethany, CT (US); Bernd Riedl, Wuppertal (DE); Scott Wilhelm, Orange, CT (US)

(73) Assignee: Bayer Healthcare LLC, Tarrytown, NY (US)

( * ) Notice: Subject to any disclaimer, the term of this patent is extended or adjusted under 35 U.S.C. 154(b) by 1812 days.

(21) Appl. No.: 10/895,985

(22) Filed: Jul. 22, 2004

(65) Prior Publication Data

US 2005/0038080 A1 Feb. 17, 2005

Related U.S. Application Data

(60) Provisional application No. 60/489,102, filed on Jul. 23, 2003, provisional application No. 60/540,326, filed on Feb. 2, 2004.

(51) Int. Cl.
*A61K 31/4412* (2006.01)
*C07D 213/62* (2006.01)

(52) U.S. Cl.
USPC .......................... 514/350; 546/298

(58) Field of Classification Search
USPC .......................... 546/298; 514/350
See application file for complete search history.

(56) References Cited

U.S. PATENT DOCUMENTS

| | | |
|---|---|---|
| 502,504 A | 8/1893 | Thoms |
| 1,792,156 A | 2/1931 | Fitzky |
| 2,046,375 A | 7/1936 | Goldstein et al. |
| 2,093,265 A | 9/1937 | Coffey et al. |
| 2,288,422 A | 6/1942 | Rohm et al. |
| 2,649,476 A | 8/1953 | Martin |
| 2,683,082 A | 7/1954 | Hill et al. |
| 2,722,544 A | 11/1955 | Martin |
| 2,745,874 A | 5/1956 | Schetty et al. |
| 2,781,330 A | 2/1957 | Downey |
| 2,797,214 A | 6/1957 | Bossard |
| 2,867,659 A | 1/1959 | Model et al. |
| 2,877,268 A | 3/1959 | Applegath et al. |
| 2,960,488 A | 11/1960 | Tamblyn et al. |
| 2,973,386 A | 2/1961 | Weldon |
| 3,151,023 A | 9/1964 | Martin |
| 3,200,035 A | 8/1965 | Martin et al. |
| 3,230,141 A | 1/1966 | Frick et al. |
| 3,284,433 A | 11/1966 | Becker et al. |
| 3,424,760 A | 1/1969 | Helsley et al. |
| 3,424,761 A | 1/1969 | Helsley et al. |
| 3,424,762 A | 1/1969 | Helsley et al. |
| 3,547,940 A | 12/1970 | Brantley |
| 3,639,668 A | 2/1972 | Alles et al. |
| 3,646,059 A | 2/1972 | Brantley |
| 3,668,222 A | 6/1972 | Hauser |
| 3,689,550 A | 9/1972 | Schellenbaum et al. |
| 3,743,498 A | 7/1973 | Brantley |
| 3,754,887 A | 8/1973 | Brantley |
| 3,823,161 A | 7/1974 | Lesser |
| 3,828,001 A | 8/1974 | Broad et al. |
| 3,860,645 A | 1/1975 | Nikawitz |
| 3,990,879 A | 11/1976 | Soper |
| 4,001,256 A | 1/1977 | Callahan et al. |
| 4,009,847 A | 3/1977 | Aldrich et al. |
| 4,042,372 A | 8/1977 | Harper |
| 4,062,861 A | 12/1977 | Yukinaga et al. |
| 4,071,524 A | 1/1978 | Banitt |
| 4,103,022 A | 7/1978 | Sirrenberg et al. |
| 4,111,680 A | 9/1978 | Yukinaga et al. |
| 4,111,683 A | 9/1978 | Singer |
| 4,116,671 A | 9/1978 | Yukinaga et al. |
| 4,173,637 A | 11/1979 | Nishiyama et al. |
| 4,173,638 A | 11/1979 | Nishiyama et al. |
| 4,183,854 A | 1/1980 | Crossley |
| 4,212,981 A | 7/1980 | Yukinaga et al. |

(Continued)

FOREIGN PATENT DOCUMENTS

| | | |
|---|---|---|
| CH | 47/9557 | 11/1969 |
| CL | 38688 | 6/1993 |

(Continued)

OTHER PUBLICATIONS

Caplus 86:72448, Abstract JP 57053785, Pyridine derivatives, Maeda Ryozo et al., Nov. 15, 1982.
Caplus 84:180049, Abstract JP 56029871, Hamada Yoshinori et al., Jul. 10, 1981.
Caplus 84:43857, Abstract JP 58021626, Maeda Ryozo et al., May 2, 1983.
Abstract of JP 55162772, Substituted acetic derivatives, Shionogi & Co., May 23, 1980.
Abstract of EP 0 202 538 A1, "Growth Promoting Agents," Nov. 26, 1986.

(Continued)

*Primary Examiner* — Kamal Saeed
*Assistant Examiner* — Janet L Coppins
(74) *Attorney, Agent, or Firm* — Millen, White, Zelano & Branigan, P.C.

(57) ABSTRACT

A compound of Formula (I):

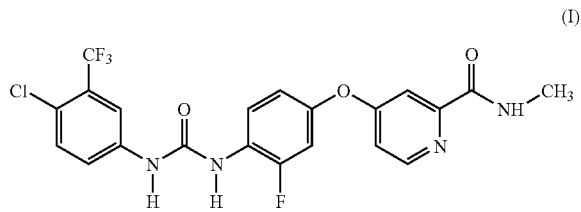

(I)

salts thereof, prodrugs thereof, metabolites thereof, pharmaceutical compositions containing such a compound, and use of such compound and compositions to treat diseases mediated by raf, VEGFR, PDGFR, p38 and flt-3.

16 Claims, No Drawings

(56) References Cited

U.S. PATENT DOCUMENTS

| | | |
|---|---|---|
| 4,240,820 A | 12/1980 | Dickore et al. |
| 4,279,639 A | 7/1981 | Okamoto et al. |
| 4,358,596 A | 11/1982 | Kriiger |
| 4,405,644 A | 9/1983 | Kabbe et al. |
| 4,410,697 A | 10/1983 | Török et al. |
| 4,418,066 A | 11/1983 | Boger et al. |
| 4,437,878 A | 3/1984 | Acker et al. |
| 4,468,380 A | 8/1984 | O'Doherty et al. |
| 4,473,579 A | 9/1984 | Devries et al. |
| 4,499,097 A | 2/1985 | Tomcufcik et al. |
| 4,511,571 A | 4/1985 | Böger et al. |
| 4,514,571 A | 4/1985 | Nakai et al. |
| 4,526,997 A | 7/1985 | O'Doherty et al |
| 4,540,566 A | 9/1985 | Davis et al. |
| 4,546,191 A | 10/1985 | Nishiyama et al. |
| 4,587,240 A | 5/1986 | Hider et al. |
| 4,623,662 A | 11/1986 | DeVries |
| 4,643,849 A | 2/1987 | Hirai et al. |
| 4,677,111 A | 6/1987 | Haga et al. |
| 4,740,520 A | 4/1988 | Hallenbach et al. |
| 4,760,063 A | 7/1988 | Hallenbach et al. |
| 4,775,763 A | 10/1988 | Dalton et al. |
| 4,808,588 A | 2/1989 | King |
| 4,820,871 A | 4/1989 | Kissener et al. |
| 4,835,180 A | 5/1989 | Schlegel et al. |
| 4,863,924 A | 9/1989 | Haga et al. |
| 4,898,886 A | 2/1990 | Amat-Larraz |
| 4,904,668 A | 2/1990 | Kondo et al. |
| 4,973,675 A | 11/1990 | Israel et al. |
| 4,983,605 A | 1/1991 | Kondo et al. |
| 4,985,449 A | 1/1991 | Haga et al. |
| 5,036,072 A | 7/1991 | Nakajima et al. |
| 5,059,614 A | 10/1991 | Lepage et al. |
| 5,063,247 A | 11/1991 | Sekiya et al. |
| 5,098,907 A | 3/1992 | Kondo et al. |
| 5,100,883 A | 3/1992 | Schiehser |
| 5,118,677 A | 6/1992 | Caufield |
| 5,118,678 A | 6/1992 | Kao et al. |
| 5,120,842 A | 6/1992 | Failli et al. |
| 5,130,331 A | 7/1992 | Pascual |
| 5,151,344 A | 9/1992 | Abe et al. |
| 5,151,413 A | 9/1992 | Caufield et al. |
| 5,162,360 A | 11/1992 | Creswell et al. |
| 5,185,358 A | 2/1993 | Creswell et al. |
| 5,254,582 A | 10/1993 | Boder et al. |
| 5,256,790 A | 10/1993 | Nelson |
| 5,258,389 A | 11/1993 | Goulet et al. |
| 5,270,458 A | 12/1993 | Lemischka |
| 5,283,354 A | 2/1994 | Lemischka |
| 5,290,795 A | 3/1994 | Hansen |
| 5,312,820 A | 5/1994 | Ashton et al. |
| 5,319,099 A | 6/1994 | Kamata et al. |
| 5,378,725 A | 1/1995 | Bonjouklian et al. |
| 5,399,566 A | 3/1995 | Katano et al. |
| 5,423,905 A | 6/1995 | Fringeli |
| 5,429,918 A | 7/1995 | Seto et al. |
| 5,432,468 A | 7/1995 | Moriyama et al. |
| 5,441,947 A | 8/1995 | Dodge et al. |
| 5,447,957 A | 9/1995 | Adams et al. |
| 5,456,920 A | 10/1995 | Matoba et al. |
| 5,468,773 A | 11/1995 | Dodge et al. |
| 5,470,882 A | 11/1995 | Dixon et al. |
| 5,480,906 A | 1/1996 | Creemer et al. |
| 5,500,424 A | 3/1996 | Nagamine et al. |
| 5,504,103 A | 4/1996 | Bonjouklian et al. |
| 5,508,288 A | 4/1996 | Forbes et al. |
| 5,547,966 A | 8/1996 | Atwal et al. |
| 5,559,137 A | 9/1996 | Adams et al. |
| 5,596,001 A | 1/1997 | Hamanaka |
| 5,597,719 A | 1/1997 | Freed et al. |
| 5,624,937 A | 4/1997 | Reel et al. |
| 5,656,612 A | 8/1997 | Monia |
| 5,658,903 A | 8/1997 | Adams et al. |
| 5,667,226 A | 9/1997 | Mannesmann |
| 5,696,138 A | 12/1997 | Olesen et al. |
| 5,698,581 A | 12/1997 | Kleemann et al. |
| 5,710,094 A | 1/1998 | Minami et al. |
| 5,721,237 A | 2/1998 | Myers et al. |
| 5,726,167 A | 3/1998 | Dodge et al. |
| 5,747,498 A | 5/1998 | Schnur et al. |
| 5,773,459 A | 6/1998 | Tang et al. |
| 5,777,097 A | 7/1998 | Lee et al. |
| 5,780,262 A | 7/1998 | Brent et al. |
| 5,780,483 A | 7/1998 | Widdowson et al. |
| 5,783,664 A | 7/1998 | Lee et al. |
| 5,786,362 A | 7/1998 | Krongrad |
| 5,807,876 A | 9/1998 | Armistead et al. |
| 5,807,891 A | 9/1998 | Bold et al. |
| 5,808,080 A | 9/1998 | Bell et al. |
| 5,814,646 A | 9/1998 | Heinz et al. |
| 5,869,043 A | 2/1999 | McDonnell |
| 5,871,934 A | 2/1999 | Lee et al. |
| 5,886,044 A | 3/1999 | Widdowson et al. |
| 5,891,895 A | 4/1999 | Shiraishi et al. |
| 5,908,865 A | 6/1999 | Doi et al. |
| 5,919,773 A | 7/1999 | Monia et al. |
| 5,929,250 A | 7/1999 | Widdowson et al. |
| 5,955,366 A | 9/1999 | Lee et al. |
| 5,965,573 A | 10/1999 | Petrie et al. |
| 6,004,965 A | 12/1999 | Breu et al. |
| 6,005,008 A | 12/1999 | Widdowson et al. |
| 6,015,908 A | 1/2000 | Widdowson et al. |
| 6,017,692 A | 1/2000 | Brent et al. |
| 6,020,345 A | 2/2000 | Vacher et al. |
| 6,022,884 A | 2/2000 | Mantlo et al. |
| 6,025,151 A | 2/2000 | Peterson |
| 6,033,873 A | 3/2000 | McDonnell et al. |
| 6,040,339 A | 3/2000 | Yoshida et al. |
| 6,043,374 A | 3/2000 | Widdowson et al. |
| 6,080,763 A | 6/2000 | Regan et al. |
| 6,093,742 A | 7/2000 | Salituro et al. |
| 6,103,692 A | 8/2000 | Avruch et al. |
| 6,114,517 A | 9/2000 | Monia et al. |
| 6,130,053 A | 10/2000 | Thompson et al. |
| 6,133,319 A | 10/2000 | Widdowson |
| 6,136,779 A | 10/2000 | Foulkes et al. |
| 6,143,764 A | 11/2000 | Kubo et al. |
| 6,147,107 A | 11/2000 | Dent et al. |
| 6,147,116 A | 11/2000 | Barbachyn et al. |
| 6,150,415 A | 11/2000 | Hammock et al. |
| 6,174,901 B1 | 1/2001 | Mantlo et al. |
| 6,177,401 B1 | 1/2001 | Ullrich et al. |
| 6,178,399 B1 | 1/2001 | Takebayashi et al. |
| 6,180,631 B1 | 1/2001 | McMahon et al. |
| 6,180,675 B1 | 1/2001 | Widdowson et al. |
| 6,187,799 B1 | 2/2001 | Wood et al. |
| 6,193,965 B1 | 2/2001 | Karin et al. |
| 6,204,267 B1 | 3/2001 | Tang et al. |
| 6,211,373 B1 | 4/2001 | Widdowson et al. |
| 6,218,539 B1 | 4/2001 | Widdowson |
| 6,228,881 B1 | 5/2001 | Regan et al. |
| 6,235,764 B1 | 5/2001 | Larson et al. |
| 6,242,601 B1 | 6/2001 | Breu et al. |
| 6,262,113 B1 | 7/2001 | Widdowson et al. |
| 6,271,261 B1 | 8/2001 | Widdowson |
| 6,294,350 B1 | 9/2001 | Peterson |
| 6,297,381 B1 | 10/2001 | Cirillo et al. |
| 6,310,068 B1 | 10/2001 | Böttcher et al. |
| 6,316,462 B1 | 11/2001 | Bishop et al. |
| 6,319,921 B1 | 11/2001 | Cirillo et al. |
| 6,329,415 B1 | 12/2001 | Cirillo et al. |
| 6,333,341 B1 | 12/2001 | Mantlo et al. |
| 6,339,045 B1 | 1/2002 | Kanno et al. |
| 6,344,476 B1 | 2/2002 | Ranges et al. |
| 6,352,977 B1 | 3/2002 | Astles et al. |
| 6,358,525 B1 | 3/2002 | Guo et al. |
| 6,358,945 B1 | 3/2002 | Breitfelder et al. |
| 6,361,773 B1 | 3/2002 | Lee et al. |
| 6,372,773 B1 | 4/2002 | Regan |
| 6,372,933 B1 | 4/2002 | Baine et al. |
| 6,380,218 B1 | 4/2002 | Marfat et al. |
| 6,383,734 B1 | 5/2002 | Marshall et al. |
| 6,387,900 B1 | 5/2002 | Pevarello et al. |
| 6,391,917 B1 | 5/2002 | Petrie et al. |

(56) References Cited

U.S. PATENT DOCUMENTS

| | | |
|---|---|---|
| 6,403,588 B1 | 6/2002 | Hayakawa et al. |
| 6,414,011 B1 | 7/2002 | Hogenkamp et al. |
| 6,444,691 B1 | 9/2002 | Oremus et al. |
| 6,448,079 B1 | 9/2002 | Monia et al. |
| 6,479,519 B1 | 11/2002 | Astles et al. |
| 6,492,393 B1 | 12/2002 | Breitfelder et al. |
| 6,495,331 B1 | 12/2002 | Gelfand et al. |
| 6,500,863 B1 | 12/2002 | Jin et al. |
| 6,511,800 B1 | 1/2003 | Singh |
| 6,511,997 B1 | 1/2003 | Minami et al. |
| 6,521,407 B1 | 2/2003 | Warenius et al. |
| 6,521,592 B2 | 2/2003 | Ko et al. |
| 6,524,832 B1 | 2/2003 | Kufe et al. |
| 6,525,046 B1 | 2/2003 | Cirillo et al. |
| 6,525,065 B1 | 2/2003 | Caldwell et al. |
| 6,525,091 B2 | 2/2003 | Robinson et al. |
| 6,583,282 B1 | 6/2003 | Zhang et al. |
| 6,608,052 B2 | 8/2003 | Breitfelder et al. |
| 6,617,324 B1 | 9/2003 | Naraian et al. |
| 6,635,421 B1 | 10/2003 | Klagsbrun et al. |
| 6,653,320 B2 | 11/2003 | Hayakawa et al. |
| 6,656,963 B2 | 12/2003 | Firestone et al. |
| 6,673,777 B1 | 1/2004 | Tracey et al. |
| 6,689,560 B1 | 2/2004 | Rapp et al. |
| 6,797,823 B1 | 9/2004 | Kazuo et al. |
| 7,070,968 B2 | 7/2006 | Kufe et al. |
| 7,235,576 B1 | 6/2007 | Riedl et al. |
| 7,253,286 B2 | 8/2007 | Funahashi et al. |
| 7,307,071 B2 | 12/2007 | Lyons et al. |
| 7,329,670 B1 | 2/2008 | Dumas et al. |
| 7,351,834 B1 | 4/2008 | Riedl et al. |
| 7,371,736 B2 | 5/2008 | Shaughnessy et al. |
| 7,371,763 B2 | 5/2008 | Dumas |
| 7,517,880 B2 | 4/2009 | Miller et al. |
| 7,528,255 B2 | 5/2009 | Riedl et al. |
| 7,557,129 B2 | 7/2009 | Scott et al. |
| 7,625,915 B2 | 12/2009 | Dumas et al. |
| 7,678,811 B2 | 3/2010 | Dumas et al. |
| 7,838,524 B2 | 11/2010 | Lee et al. |
| 7,838,541 B2 | 11/2010 | Dumas et al. |
| 7,897,623 B2 | 3/2011 | Riedl et al. |
| 7,928,239 B2 | 4/2011 | Dumas et al. |
| 7,928,277 B1 | 4/2011 | Cox, Jr. |
| 8,071,616 B2 | 12/2011 | Dumas et al. |
| 8,076,488 B2 | 12/2011 | Dumas et al. |
| 8,101,773 B2 | 1/2012 | Smith et al. |
| 8,110,887 B2 | 2/2012 | Dumas et al. |
| 8,124,630 B2 | 2/2012 | Riedl et al. |
| 8,124,782 B2 | 2/2012 | Logers et al. |
| 8,207,166 B2 | 6/2012 | Lee et al. |
| 2001/0006975 A1 | 7/2001 | Wood et al. |
| 2001/0011135 A1 | 8/2001 | Riedl et al. |
| 2001/0011136 A1 | 8/2001 | Riedl et al. |
| 2001/0016659 A1 | 8/2001 | Riedl et al. |
| 2001/0027202 A1 | 10/2001 | Riedl et al. |
| 2001/0034447 A1 | 10/2001 | Riedl et al. |
| 2001/0038842 A1 | 11/2001 | Achen et al. |
| 2002/0037276 A1 | 3/2002 | Ptasznik et al. |
| 2002/0042517 A1 | 4/2002 | Uday et al. |
| 2002/0062763 A1 | 5/2002 | Macholdt et al. |
| 2002/0065283 A1 | 5/2002 | McMahon et al. |
| 2002/0065296 A1 | 5/2002 | Dumas et al. |
| 2002/0082255 A1 | 6/2002 | Eastwood |
| 2002/0085857 A1 | 7/2002 | Kim et al. |
| 2002/0085859 A1 | 7/2002 | Hashimoto et al. |
| 2002/0103253 A1 | 8/2002 | Ranges et al. |
| 2002/0128321 A1 | 9/2002 | Widdowson et al. |
| 2002/0137774 A1 | 9/2002 | Riedl et al. |
| 2002/0161014 A1 | 10/2002 | Sadhu et al. |
| 2002/0165275 A1 | 11/2002 | Wu et al. |
| 2002/0165349 A1 | 11/2002 | Kirsch et al. |
| 2002/0165394 A1 | 11/2002 | Dumas et al. |
| 2002/0173507 A1 | 11/2002 | Santora et al. |
| 2002/0188027 A1 | 12/2002 | Robinson et al. |
| 2003/0069284 A1 | 4/2003 | Keegan et al. |
| 2003/0125359 A1 | 7/2003 | Lyons et al. |
| 2003/0130309 A1 | 7/2003 | Moss et al. |
| 2003/0139605 A1 | 7/2003 | Riedl et al. |
| 2003/0144278 A1 | 7/2003 | Riedl et al. |
| 2003/0157104 A1 | 8/2003 | Waksal |
| 2003/0181442 A1 | 9/2003 | Riedl et al. |
| 2003/0207870 A1 | 11/2003 | Dumas et al. |
| 2003/0207872 A1 | 11/2003 | Riedl et al. |
| 2003/0207914 A1 | 11/2003 | Dumas et al. |
| 2003/0216446 A1 | 11/2003 | Dumas et al. |
| 2003/0232400 A1 | 12/2003 | Radka et al. |
| 2003/0232765 A1 | 12/2003 | Carter et al. |
| 2004/0096855 A1 | 5/2004 | Stratton et al. |
| 2004/0147541 A1 | 7/2004 | Lane et al. |
| 2004/0192770 A1 | 9/2004 | Kozikowski et al. |
| 2004/0197256 A1 | 10/2004 | Rogers et al. |
| 2004/0209905 A1 | 10/2004 | Kubo et al. |
| 2004/0229937 A1 | 11/2004 | Dumas et al. |
| 2004/0235829 A1 | 11/2004 | Scott et al. |
| 2005/0004533 A1 | 1/2005 | Smith |
| 2005/0032798 A1 | 2/2005 | Boyer et al. |
| 2005/0038031 A1 | 2/2005 | Dumas et al. |
| 2005/0038080 A1 | 2/2005 | Boyer et al. |
| 2005/0059703 A1* | 3/2005 | Wilhelm et al. .............. 514/338 |
| 2005/0192304 A1 | 9/2005 | Nagarathnam et al. |
| 2005/0209261 A1 | 9/2005 | Nagarathnam et al. |
| 2005/0256174 A1 | 11/2005 | Wood et al. |
| 2005/0288286 A1 | 12/2005 | Flynn et al. |
| 2006/0058358 A1 | 3/2006 | Dumas et al. |
| 2006/0078617 A1 | 4/2006 | Schueckler |
| 2006/0211738 A1 | 9/2006 | Mitchell et al. |
| 2006/0234931 A1 | 10/2006 | Biggs et al. |
| 2006/0247186 A1 | 11/2006 | Carter et al. |
| 2007/0020704 A1 | 1/2007 | Wilhelm et al. |
| 2007/0105142 A1 | 5/2007 | Wilhelm |
| 2007/0173514 A1 | 7/2007 | Moss |
| 2007/0178494 A1 | 8/2007 | Elting et al. |
| 2007/0244120 A1 | 10/2007 | Dumas et al. |
| 2007/0265315 A1 | 11/2007 | Dumas et al. |
| 2008/0009527 A1 | 1/2008 | Dumas et al. |
| 2008/0027061 A1 | 1/2008 | Riedl et al. |
| 2008/0032979 A1 | 2/2008 | Riedl et al. |
| 2008/0045546 A1 | 2/2008 | Bouchon et al. |
| 2008/0045589 A1 | 2/2008 | Kelley |
| 2008/0085902 A1 | 4/2008 | Bold et al. |
| 2008/0108672 A1 | 5/2008 | Riedl et al. |
| 2008/0153823 A1 | 6/2008 | Riedl et al. |
| 2008/0194580 A1 | 8/2008 | Dumas et al. |
| 2008/0214545 A1 | 9/2008 | Lee et al. |
| 2008/0227828 A1 | 9/2008 | Dumas et al. |
| 2008/0242707 A1 | 10/2008 | Schuckler et al. |
| 2008/0262236 A1 | 10/2008 | Logers et al. |
| 2008/0269265 A1 | 10/2008 | Miller et al. |
| 2008/0300281 A1 | 12/2008 | Dumas et al. |
| 2008/0311601 A1 | 12/2008 | Elting et al. |
| 2009/0068146 A1 | 3/2009 | Wilhelm |
| 2009/0093526 A1 | 4/2009 | Miller et al. |
| 2009/0118268 A1 | 5/2009 | Riedl et al. |
| 2009/0176791 A1 | 7/2009 | Sandner et al. |
| 2009/0192127 A1 | 7/2009 | Scheuring et al. |
| 2009/0215833 A1 | 8/2009 | Grunenberg et al. |
| 2009/0215835 A1 | 8/2009 | Wilhelm |
| 2009/0221010 A1 | 9/2009 | Elting et al. |
| 2009/0227637 A1 | 9/2009 | Weber et al. |
| 2009/0306020 A1 | 12/2009 | Scheuring et al. |
| 2010/0035888 A1 | 2/2010 | Sandner et al. |
| 2010/0063088 A1 | 3/2010 | Wood et al. |
| 2010/0063112 A1 | 3/2010 | Grunenberg et al. |
| 2010/0075971 A1 | 3/2010 | Dumas et al. |
| 2010/0081812 A1 | 4/2010 | Smith et al. |
| 2010/0113533 A1 | 5/2010 | Stiehl et al. |
| 2010/0125139 A1 | 5/2010 | Bankston et al. |
| 2010/0129321 A1 | 5/2010 | Weber et al. |
| 2010/0144749 A1 | 6/2010 | Wilhelm |
| 2010/0150863 A1 | 6/2010 | Smith et al. |
| 2010/0160371 A1 | 6/2010 | Ranges et al. |
| 2010/0173953 A1 | 7/2010 | Grunenberg et al. |
| 2010/0173954 A1 | 7/2010 | Wilhelm et al. |
| 2010/0249159 A1 | 9/2010 | Nagarathnam et al. |

(56) References Cited

U.S. PATENT DOCUMENTS

| | | |
|---|---|---|
| 2010/0267777 A1 | 10/2010 | Wilhelm et al. |
| 2011/0015195 A1 | 1/2011 | Dumas et al. |
| 2011/0136809 A1 | 6/2011 | Lee et al. |
| 2011/0158942 A1 | 6/2011 | Weber et al. |
| 2011/0178137 A1 | 7/2011 | Albrecht-Kupper et al. |
| 2011/0195110 A1 | 8/2011 | Smith et al. |
| 2011/0257035 A1 | 10/2011 | Pena et al. |
| 2012/0009150 A1 | 1/2012 | Weber et al. |
| 2012/0040925 A1 | 2/2012 | Carter et al. |
| 2012/0040986 A1 | 2/2012 | Riedl et al. |
| 2012/0046290 A1 | 2/2012 | Miller et al. |
| 2012/0129893 A1 | 5/2012 | Dumas et al. |
| 2012/0142741 A1 | 6/2012 | Schueckler |
| 2012/0142742 A1 | 6/2012 | Riedl et al. |

FOREIGN PATENT DOCUMENTS

| | | |
|---|---|---|
| CL | 0384-2004 | 11/2004 |
| CL | 2744-2003 | 2/2005 |
| CL | 1702-2004 | 5/2005 |
| CL | 1805-2004 | 9/2005 |
| CN | 2 146 707 | 10/1995 |
| DE | 487 014 C1 | 11/1929 |
| DE | 511 468 C1 | 10/1930 |
| DE | 523 437 C1 | 4/1931 |
| DE | 2436179 C2 | 2/1975 |
| DE | 25 01 648 A1 | 7/1975 |
| DE | 2436179 A1 | 10/1981 |
| DE | 3305866 A1 | 8/1984 |
| DE | 35 29 247 A1 | 2/1987 |
| DE | 3529247 A1 | 2/1987 |
| DE | 35 40 377 A1 | 5/1987 |
| DE | 253997 A1 | 2/1988 |
| EP | 0016371 A1 | 10/1980 |
| EP | 0107214 A2 | 9/1983 |
| EP | 0116932 A1 | 8/1984 |
| EP | 0192263 B1 | 8/1986 |
| EP | 0202538 A1 | 11/1986 |
| EP | 0230400 A2 | 7/1987 |
| EP | 0233559 B1 | 8/1987 |
| EP | 0242666 A1 | 10/1987 |
| EP | 0264904 A2 | 4/1988 |
| EP | 0314615 W | 5/1989 |
| EP | 0335156 A1 | 10/1989 |
| EP | 0359148 A2 | 3/1990 |
| EP | 0371876 A1 | 6/1990 |
| EP | 0379915 A1 | 8/1990 |
| EP | 0380048 A2 | 8/1990 |
| EP | 0381987 A1 | 8/1990 |
| EP | 0405233 A1 | 1/1991 |
| EP | 0425443 A1 | 5/1991 |
| EP | 0459887 A1 | 12/1991 |
| EP | 0509795 A2 | 10/1992 |
| EP | 0709225 A1 | 5/1995 |
| EP | 0690344 | 6/1995 |
| EP | 0676395 A2 | 10/1995 |
| EP | 0 690 344 A1 | 1/1996 |
| EP | 0709225 B1 | 5/1996 |
| EP | 0860433 A1 | 8/1998 |
| EP | 1199306 A1 | 4/2002 |
| EP | 903239.2-2103 R | 8/2002 |
| EP | 1256587 A1 | 11/2002 |
| EP | 1 275 386 A1 | 1/2003 |
| EP | 1537075 | 8/2005 |
| EP | 905597.1-2313 R | 7/2008 |
| FR | 1 457 172 A | 9/1966 |
| GB | 828 231 | 10/1956 |
| GB | 771 333 | 3/1957 |
| GB | 828231 | 2/1960 |
| GB | 921 682 | 3/1963 |
| GB | 1110099 | 6/1966 |
| GB | 1 590 870 | 6/1981 |
| GB | 1590870 | 6/1981 |
| HU | P0004437 | 12/1998 |
| IR | 26555 | 1/2000 |
| JP | 44 2569 | 2/1944 |
| JP | 50-76072 | 6/1975 |
| JP | 50-77375 | 6/1975 |
| JP | 50-149668 | 11/1975 |
| JP | 51-063170 A | 6/1976 |
| JP | 51-080862 A | 7/1976 |
| JP | 53-086033 A | 7/1978 |
| JP | 54-032468 | 9/1979 |
| JP | 55-98152 A | 7/1980 |
| JP | 55-124763 A | 9/1980 |
| JP | 55-162772 | 12/1980 |
| JP | 57-109721 | 7/1982 |
| JP | 61020039 A | 7/1984 |
| JP | 02035450 A | 7/1988 |
| JP | 06075172 A | 9/1988 |
| JP | 01009455 A | 1/1989 |
| JP | 01102461 A | 4/1989 |
| JP | 1132580 A | 5/1989 |
| JP | 01200254 | 8/1989 |
| JP | 01259360 | 10/1989 |
| JP | 03198049 A | 12/1989 |
| JP | 2022650 | 1/1990 |
| JP | 2023337 | 1/1990 |
| JP | 2023337 | 1/1990 |
| JP | 2023337 W | 1/1990 |
| JP | 02105016 A | 4/1990 |
| JP | 02108048 A | 4/1990 |
| JP | 02150840 A | 6/1990 |
| JP | 3 532 47 A | 3/1991 |
| JP | 03144634 A | 6/1991 |
| JP | 06120039 A | 10/1992 |
| JP | 08-301841 A | 11/1996 |
| JP | 10-306078 A | 11/1998 |
| JP | 11-158149 | 6/1999 |
| LB | 6124 | 1/2000 |
| LB | 6124 | 5/2000 |
| WO | WO 90/02112 A1 | 3/1990 |
| WO | WO 92/03413 A1 | 3/1992 |
| WO | 92/05179 | 4/1992 |
| WO | 93/04170 A1 | 3/1993 |
| WO | WO 93/18028 A1 | 9/1993 |
| WO | WO 93/24458 A1 | 12/1993 |
| WO | 94/02136 | 2/1994 |
| WO | 94/02485 | 2/1994 |
| WO | 94/04541 | 3/1994 |
| WO | WO 94/14801 A1 | 7/1994 |
| WO | WO 94/18170 A1 | 8/1994 |
| WO | 94/23755 | 10/1994 |
| WO | WO 94/22807 A1 | 10/1994 |
| WO | WO 94/25012 A1 | 11/1994 |
| WO | 95/02136 | 1/1995 |
| WO | WO 95/02591 A1 | 1/1995 |
| WO | WO 95/07922 A1 | 3/1995 |
| WO | 95/14023 | 5/1995 |
| WO | WO 95/13067 A1 | 5/1995 |
| WO | 95/16691 | 6/1995 |
| WO | 95/19169 A2 | 7/1995 |
| WO | WO 95/31451 A1 | 11/1995 |
| WO | WO 95/33458 A1 | 12/1995 |
| WO | WO 96/02112 A1 | 1/1996 |
| WO | WO 96/10559 A1 | 4/1996 |
| WO | WO 96/13632 A1 | 5/1996 |
| WO | WO 96/25157 A1 | 8/1996 |
| WO | 96/41807 | 12/1996 |
| WO | WO 96/40673 A1 | 12/1996 |
| WO | WO 96/40675 A1 | 12/1996 |
| WO | 97/03069 | 1/1997 |
| WO | WO 97/09973 A2 | 3/1997 |
| WO | WO 97/17267 A1 | 5/1997 |
| WO | WO 97/17329 A1 | 5/1997 |
| WO | WO 97/29743 A1 | 8/1997 |
| WO | WO 97/30992 A1 | 8/1997 |
| WO | 97/34146 A1 | 9/1997 |
| WO | WO 97/40028 A1 | 10/1997 |
| WO | 97/40842 A1 | 11/1997 |
| WO | WO 97/45400 A1 | 12/1997 |
| WO | WO 97/49399 A1 | 12/1997 |
| WO | WO 97/49400 A1 | 12/1997 |

(56) References Cited

FOREIGN PATENT DOCUMENTS

| | | |
|---|---|---|
| WO | 98/17207 A1 | 4/1998 |
| WO | WO 98/17267 A1 | 4/1998 |
| WO | WO 98/20868 | 5/1998 |
| WO | WO 98/20868 A1 | 5/1998 |
| WO | WO 98/22103 A1 | 5/1998 |
| WO | WO 98/22432 A1 | 5/1998 |
| WO | WO 98/32439 A1 | 7/1998 |
| WO | WO 98/34929 A1 | 8/1998 |
| WO | WO 98/34947 A1 | 8/1998 |
| WO | 98/45268 A1 | 10/1998 |
| WO | WO 98 45268 A1 | 10/1998 |
| WO | WO 98/45268 A1 | 10/1998 |
| WO | 98/49150 A1 | 11/1998 |
| WO | 98/52937 A2 | 11/1998 |
| WO | 98/52941 A1 | 11/1998 |
| WO | WO 98/52558 A1 | 11/1998 |
| WO | WO 98/52559 A1 | 11/1998 |
| WO | 98/56377 | 12/1998 |
| WO | 98/56377 A1 | 12/1998 |
| WO | WO 99/00357 | 1/1999 |
| WO | WO 99/00370 A1 | 1/1999 |
| WO | 99/20617 A1 | 4/1999 |
| WO | WO 99/20617 A1 | 4/1999 |
| WO | 99/24035 | 5/1999 |
| WO | WO 99/21835 A1 | 5/1999 |
| WO | WO 99/23091 A1 | 5/1999 |
| WO | WO 99/24398 A2 | 5/1999 |
| WO | WO 99/24635 A1 | 5/1999 |
| WO | 99/26657 A1 | 6/1999 |
| WO | WO 99/28305 A1 | 6/1999 |
| WO | 99/32109 | 7/1999 |
| WO | 99/35132 | 7/1999 |
| WO | WO 99/32106 A1 | 7/1999 |
| WO | WO 99/32110 A1 | 7/1999 |
| WO | WO 99/32111 A1 | 7/1999 |
| WO | WO 99/32436 A1 | 7/1999 |
| WO | WO 99/32437 A1 | 7/1999 |
| WO | WO 99/32455 A1 | 7/1999 |
| WO | WO 99/32463 A1 | 7/1999 |
| WO | WO 99/33458 A1 | 7/1999 |
| WO | WO 99/40673 A1 | 8/1999 |
| WO | 99/58502 A1 | 11/1999 |
| WO | WO 99/62890 A1 | 12/1999 |
| WO | 00/12497 | 3/2000 |
| WO | WO 00/17175 A1 | 3/2000 |
| WO | 00/19205 A1 | 4/2000 |
| WO | 00/27414 A2 | 5/2000 |
| WO | PCT/US00/00648 R | 5/2000 |
| WO | PCT/US00/00768 R | 5/2000 |
| WO | WO 00/26203 A1 | 5/2000 |
| WO | 00/31238 A2 | 6/2000 |
| WO | 00/34303 A1 | 6/2000 |
| WO | 00/35455 A1 | 6/2000 |
| WO | 00/39116 | 6/2000 |
| WO | WO 00/35454 A1 | 6/2000 |
| WO | WO-00/42012 * | 6/2000 |
| WO | 00/39101 | 7/2000 |
| WO | WO 00/41698 A1 | 7/2000 |
| WO | WO 00/42012 A1 | 7/2000 |
| WO | WO 00/43366 A1 | 7/2000 |
| WO | WO 00/43384 A1 | 7/2000 |
| WO | WO 02/42012 A1 | 7/2000 |
| WO | WO 00/47577 A1 | 8/2000 |
| WO | WO 00/50425 A1 | 8/2000 |
| WO | WO 00/55139 | 9/2000 |
| WO | WO 00/55152 A1 | 9/2000 |
| WO | WO 00/56331 A1 | 9/2000 |
| WO | 00/71506 A2 | 11/2000 |
| WO | WO 00/71532 A1 | 11/2000 |
| WO | WO 01/04115 A2 | 1/2001 |
| WO | WO 01/07411 A1 | 2/2001 |
| WO | WO 01/09088 A1 | 2/2001 |
| WO | WO 01/12188 | 2/2001 |
| WO | WO 01/36403 A1 | 5/2001 |
| WO | 01/04789 A1 | 7/2001 |
| WO | 01/54723 A1 | 8/2001 |
| WO | 01/54727 A1 | 8/2001 |
| WO | 01/64303 A2 | 8/2001 |
| WO | WO 01/57008 A1 | 8/2001 |
| WO | 01/66099 | 9/2001 |
| WO | 01/66540 A1 | 9/2001 |
| WO | 02/06382 A1 | 1/2002 |
| WO | 02/07008 A1 | 1/2002 |
| WO | 02/07772 A2 | 1/2002 |
| WO | WO 02/07747 A1 | 1/2002 |
| WO | WO 02/07772 | 1/2002 |
| WO | WO 02/10141 A1 | 2/2002 |
| WO | WO 02/14281 A1 | 2/2002 |
| WO | WO 02/14311 A2 | 2/2002 |
| WO | 02/25286 | 3/2002 |
| WO | WO 02/18346 A1 | 3/2002 |
| WO | WO 02/24635 A2 | 3/2002 |
| WO | WO 02/32872 A1 | 4/2002 |
| WO | 02/40445 A1 | 5/2002 |
| WO | 02/50091 A1 | 6/2002 |
| WO | WO 02/44156 A2 | 6/2002 |
| WO | WO 02/44158 A1 | 6/2002 |
| WO | 02/060900 A2 | 8/2002 |
| WO | WO 02/059081 A2 | 8/2002 |
| WO | WO 02/059102 A2 | 8/2002 |
| WO | WO 02/062763 A2 | 8/2002 |
| WO | 02/070008 | 9/2002 |
| WO | 02/076930 A2 | 10/2002 |
| WO | 02/076977 | 10/2002 |
| WO | 02085857 A2 | 10/2002 |
| WO | WO 02/083628 A1 | 10/2002 |
| WO | WO 02/083642 A1 | 10/2002 |
| WO | WO 02/085857 A2 | 10/2002 |
| WO | WO 02/085859 A1 | 10/2002 |
| WO | 02/088090 A2 | 11/2002 |
| WO | WO 02/092576 A1 | 11/2002 |
| WO | 03/004523 | 1/2003 |
| WO | 03005999 A2 | 1/2003 |
| WO | WO 03/043630 A1 | 5/2003 |
| WO | WO 03/099771 A2 | 5/2003 |
| WO | 03/047579 A1 | 6/2003 |
| WO | WO 03/047523 A1 | 6/2003 |
| WO | WO 03/ 047523 A2 | 6/2003 |
| WO | WO 03/047579 A1 | 6/2003 |
| WO | WO 03/050455 A1 | 6/2003 |
| WO | 03/056036 A2 | 7/2003 |
| WO | 03/059373 A2 | 7/2003 |
| WO | 03/060111 A2 | 7/2003 |
| WO | 03/065995 A2 | 8/2003 |
| WO | 03068223 | 8/2003 |
| WO | WO 03/068228 A1 | 8/2003 |
| WO | WO 03/068229 A1 | 8/2003 |
| WO | WO 03/068746 A1 | 8/2003 |
| WO | WO 2003/094626 A | 9/2003 |
| WO | WO 03/082272 A2 | 10/2003 |
| WO | WO 2004/019941 A1 | 3/2004 |
| WO | WO 2004/037789 A2 | 5/2004 |
| WO | WO 2004/037789 A2 | 5/2004 |
| WO | WO 2004/043374 A2 | 5/2004 |
| WO | 2004/045578 | 6/2004 |
| WO | 2004/052880 | 6/2004 |
| WO | 2004/078128 | 9/2004 |
| WO | 2004/078747 A1 | 9/2004 |
| WO | 2004/078748 | 9/2004 |
| WO | WO 2004/078746 A2 | 9/2004 |
| WO | WO 2004/078747 A1 | 9/2004 |
| WO | WO 2004/085399 A1 | 10/2004 |
| WO | WO 2004/085425 A1 | 10/2004 |
| WO | 2004/108713 A1 | 12/2004 |
| WO | 2004/108715 A1 | 12/2004 |
| WO | 2004/113274 | 12/2004 |
| WO | WO 2004/113274 A | 12/2004 |
| WO | 2005/000284 | 1/2005 |
| WO | 2005/005434 A1 | 1/2005 |
| WO | WO 2005/000284 A2 | 1/2005 |
| WO | WO 2005/002673 A1 | 1/2005 |
| WO | WO 2005/004863 A1 | 1/2005 |
| WO | WO 2005/004864 A1 | 1/2005 |
| WO | WO 2005/005389 A2 | 1/2005 |

(56) References Cited

FOREIGN PATENT DOCUMENTS

| WO | WO 2005/006899 A1 | 1/2005 |
|---|---|---|
| WO | WO 2005/007649 A1 | 1/2005 |
| WO | 2005/009961 A2 | 2/2005 |
| WO | 2005/011700 A1 | 2/2005 |
| WO | 2005/016252 A2 | 2/2005 |
| WO | 2005009367 A2 | 2/2005 |
| WO | 2005009961 A2 | 2/2005 |
| WO | WO 2005/009367 A | 2/2005 |
| WO | WO 2005/009961 A | 2/2005 |
| WO | WO 2005/019192 A1 | 3/2005 |
| WO | WO 2005/032548 A1 | 4/2005 |
| WO | WO 2005/037273 A1 | 4/2005 |
| WO | WO 2005/037285 A1 | 4/2005 |
| WO | WO 2005/037829 A1 | 4/2005 |
| WO | WO 2005/042520 A1 | 5/2005 |
| WO | WO 2005/047283 A1 | 5/2005 |
| WO | WO 2005/048948 A2 | 6/2005 |
| WO | WO 2005/049603 A1 | 6/2005 |
| WO | WO 2005/058832 A1 | 6/2005 |
| WO | 95/33460 | 8/2005 |
| WO | 2005075425 A2 | 8/2005 |
| WO | 2005/089443 A2 | 9/2005 |
| WO | WO 2005/089443 A | 9/2005 |
| WO | WO 2005/110994 A2 | 11/2005 |
| WO | 2006/026500 | 3/2006 |
| WO | 2006/027346 A2 | 3/2006 |
| WO | WO 2006/026501 | 3/2006 |
| WO | WO 2006/034797 A | 4/2006 |
| WO | 2006105844 A1 | 10/2006 |
| WO | 2006/125540 A1 | 11/2006 |
| WO | 2007015947 A | 2/2007 |
| WO | WO 2007/015947 A | 2/2007 |
| WO | WO 2007/039404 A1 | 4/2007 |
| WO | 2007/053573 A2 | 5/2007 |
| WO | 2007/054215 A1 | 5/2007 |
| WO | 2007/059094 | 5/2007 |
| WO | 2007/059154 | 5/2007 |
| WO | 2007/059155 | 5/2007 |
| WO | 2007064872 A2 | 6/2007 |
| WO | 2007/087575 | 8/2007 |
| WO | 2007/123722 | 11/2007 |
| WO | 2007/139930 | 12/2007 |
| WO | 2008/055966 A1 | 5/2008 |
| WO | 2008/079968 | 7/2008 |
| WO | 2008/079972 | 7/2008 |
| WO | 2008/089389 | 7/2008 |
| WO | WO2008089388 | 7/2008 |
| WO | WO2008089389 | 7/2008 |
| WO | WO 2010/0048304 | 4/2010 |
| WO | WO 2011/0146725 | 11/2011 |
| WO | WO 2012 012404 | 1/2012 |

OTHER PUBLICATIONS

Audia, James E., et al., "Potent, Selective Tetrahydro-β-carboline
Abstract of DE 3305866 a (EP equivalent 116,932), R.D. Acker et al., Aug. 23, 1984.
Abstract of EP 116,932, Aug. 29, 1984.
Abstract of EP 16,371, Oct. 1, 1980.
Abstract of EP 4931A (Equivalent 4,240,820), Dickore, K. et al.
Abstract of EP 0405233A1, Tetsuo Sekiya et al.
Abstract of EP 0 676 395 (U.S. equivalent 5,698,581), Dec. 16, 1997.
Abstract WO 9822103, Hedge May 28, 1998, Philip et al.
Chemical Abstract, vol. 116, No. 21, May 25, 1992, (pp. 741-742) N 116:214456.
Tarzia, G. et al., "Synthesis and anit-inflammatory properties of some pyrrolo(1H,3H) [3,4-d]pyrimidin-2-ones and pyrrolo(1H,6H)[3,4-d]pyrimidin-2-ones," Chemical Abstracts, vol. 91, 1979, 91:74558.
XP-002918005, White, A. D., et al., "Heterocyclic Ureas: Inhibitors of Acyl-CoA:Cholesterol O-Acyltransferase as Hypochelesterolemic Agents," J. Med. Chem. 1996, 39, pp. 4382-4395. Antagonists of the Serotonin 2B (5HT$_{2B}$) Contractile Receptor in the Rat Stomach Fundus," J. Med. Chem. 1996, 39, pp. 2773-2780.
XP-000941493, Forbes, Ian T., "N-(1-Methyl-5-indolyl)-N-(3-methyl-5-isothiazolyl)urea: A Novel, High-Affinity 5-HT$_{2B}$ Receptor Antagonist," Journal of Medicinal Chem. vol. 38, No. 6, Mar. 17, 1995, pp. 855-857.
XP-000943551, Boulton, A. J., et al., "Heterocyclic Rearrangements. Part X.[1] A Generalised Monocyclic Rearrangements," J. Chem. Soc. (C), 1967, pp. 2005-2007.
W. Kolch, et al., "Raf-1 protein kinase is required for growth of induced NIH/3T3 cells," Letters to Nature, vol. 349, Jan. 31, 1991, pp. 426-428.
M. Fridman, et al., "The Minimal Fragements of c-Raf-1 and NF1 That Can Suppress v-Ha-Ras-Induced Malignant Phenotype," The Journal of Biological Chemistry, vol. 269, No. 48, Dec. 2, 1994, pp. 30105-30108.
G. L. Bolton, et al., Chapter 17. Ras Oncogene Directed Approaches in Cancer Chemotherapy, Annual Reports In Medicinal Chemistry, vol. 29, 1994, pp. 165-174.
J. L. Bos, "ras Oncogenes in Human Cancer: A Review," Cancer Research, vol. 49, Sep. 1, 1989, pp. 4682-4689.
Michaelis, Justus, Liebigs Ann. Chem. (JLACBF) 397, 1913, p. 143.
B. P. Monia, et al., "Antitumor activity of a phosphorothioate antisense oligodeoxynucleotide targeted against C-raf kinase," Nature Medicine, vol. 2, No. 6, Jun. 1996, pp. 668-675.
Lee, et al., "Bicyclic Imidazoles as a Novel Class of Cytokine Biodynthesis Inhiibitors," Annuals N.Y. Academy of Science, 1993, pp. 149-170.
F. Lepage, et al., "New N-aryl isoxazolecarboxamides and N-isoxazolybenzamides as anticonvulsant agents," Eur. J. Med. Chem., vol. 27, 1992, pp. 581-593.
Ridley, et al., "Actions of IL-1 are Selectively Controlled by p38 Mitogen-Activated Protein Kinase," The American Association of Immunologists, 1997, p. 3165-73.
N. S. Magnuson, et al., "The Raf-1 serine/threonine protein kinase," Cancer Biology, vol. 5, 1994, pp. 247-253.
G. Daum, et al., "The ins and outs of Raf Kinases,": TIBS 19, Nov. 1994, pp. 474-480.
XP-000944187, Grant, A.M. et al.: "Some Hypotensive thiadiazoles," J. Med. Chem. (1972), 15(10), p. 1082-4.
XP-000943466, Russo, F. et al. "Synthesis of 2,6-substituted derivatives of 5H-1,3,4-thiadiazolo=3,2-a!-s triazine-5,7-dione" Farmaco, Ed.Sci. (1978), 33(12), 972-83.
Joseph T. Bruder et al., Journal of Virology, Jan. 1997, "Adenovirus Infection Stimulates the Raf/MAPK Signaling Pathway and Induces Interleukin-8 Expression," May 17, 1996, pp. 398-404.
XP-000943598, Foussard-Blanpin, Odette: "Comparative pharmacodynamic study of variously substituted carboxamides of the central nervous ststem" Ann. Pharm. Fr. (1982), 40 (4), pp. 339-350.
XP-000943800, Kubo, Hiroshi et al., vol. 18, No. 1, Jan.-Feb. 1970 "Herbicidal activity of 1,3,4-thiadiazole derivatives" J. Agr. Food Chem. (1970), 18(1), pp. 60-65.
Avruch et al., "Raf meets Ras: completing the framework of a signal transduction pathway," TIBS 19; Jul. 1994; pp. 279-281.
Caplus 113:106314, Abstract of JP 2022650, Silver halide color photographic material containing a cyan coupler of 2-ureido-phenol type to improve dye developability and remove lecuo cyan dye, Noboru Mizukura et al. Jan. 25, 1990.
Caplus 113:142130, Abstract of JP 2023337, Silver halide photographic material containing phenolic cyan coupler a colorless cyan coupler, Toshihiko Yagi et al., Jan. 25, 1990.
Caplus 87:62295, "The metabolism and toxicity of halogenated carbanilides. Biliary metabolites of 3,4,4'-trichlorocarbanilide and 3-trifluoromethyl-4,4'-dichlorocarbanilide in the rat," Chemical Life Science, pp. 157-166, 1977.
Caplus 127:293717, "Optical properties of segmented oligourethane with azomethine terminal fragments," National Academy of Science of Ukraine, M. V. Kurik et al., pp. 2038-2041, 1996.
Caplus 127:273945, "Quantitative structure-biodegradability studies: an investigation of the MITI aromatic compound database," School of Pharmacy and Chemistry, J. C. Dearden, Biodegradability Prediction Edited by Willie J.G.M. Peijnenburg et al., NATO ASI Series, 2. Environment—vol. 23, pp. 93-104, 1996.

(56) References Cited

OTHER PUBLICATIONS

Caplus 126:166148, "Inhibitors of coenzyme A-independent transacylase induce apoptosis in human HL-60 cells," James D. Winkler et al., J. Pharmacol. Exp. Ther. pp. 956-966, 1996.
Caplus 98:78152, Abstract of JP 57185219, "Antitumor benzophenone derivatives," Nov. 15, 1982.
Caplus 72:79046, Abstract of CH 479557, "Tuberculostatic and cancerostatic polybasic ureas," Dr. A. Wander, Oct. 15, 1969.
Caplus 125:245169, "Production of murine monoclonal antibodies against sulcofuron and flucofuron by in vitro immunization," G. A. Bonwick et al., J. Immunol. Methods, pp. 163-173, 1996.
Caplus 127:34137f, "Preparation of quinoline an dquinazoline derivatives inhibiting platelet-derived growth factor receptor autophosphorylation," Kazuo Kubo et al., May 15, 1997.
Caplus 131:58658k, "Inhibition of raf kinase using symmetrical and unsymmetrical substituted diphenyl ureas," Miller, Scott, Jul. 1, 1999.
Caplus 131:87909y, "Inhibition of p38 kinase activity using substituted heterocyclic ureas," Jacques Dumas, Jul. 1, 1999.
Caplus 131:73649b, "Preparation of pyrazolyl aryl ureas and related compounds as p38kinase inhibitor," Jacques Dumas, Jul. 1, 1999.
Joseph V. Simone, "Cecil Textbook of Medicine," 20th Edition, vol. 1, Feb. 3, 1997. pp. 1004-1010.
XP-002205797, Cesar Raposo et al., "Catalysis of Nucleophilic Addition of Pyrrolidine to 2-(5H)-Furanone through Chromenone Cleft-Type Receptors," vol. 37, No. 38, pp. 6947-6950, 1996.
Jacqueline E. van Muijlwijk-Koezen et al., "Isoquinoline and Quinazoline Urea Analogues as Antagonists for the Human Adenosine $A_3$ Receptor," J. Ed. Chem. 2000, 43, pp. 2227-2238, Jan. 3, 2000.
Jacques Dumas et al., "1-Phenyl-5-pyrazoly Ureas: Potent and Selective p38 Kinase Inhibitors," Bioorganic & Medicinal Chemistry Letters, pp. 2051-2054, May 2, 2000.
Robert W. Carling et al., "1-(3-Cyanobenxylpiperidin-4-yl)-5-methyl-4-phenyl-1,3-dihydroimidazol-2-one: A Selective High-Affinity Antagonist for the Human Dopanine $D_4$ Receptor with Excellent Selectivity over Ion Channels," J. Med. Chem., 1999, 42, pp. 2706-2715.
Abstract of WO 9822103, May 28, 1998, John Philip Hedge et al.
Abstract of DE 3305866A1, Aug. 29, 1984, Dr. Acker Rolf-Dieter et al.
Abstract of EP 4931(equivalent 4,240,820), K. Dickore et al. (1980).
Dumas, J.. "CAS Substructure," May 6, 1997, pp. 1-29.
Scott, Bill, "Substructure (Patent Families),"Aug. 11, 1997, pp. 1-19.
Scott, Bill, "Substructure #2," Nov. 25, 1997, pp. 1-3.
"Beilstein number" Collection, 28 pages (1997).
"Beilstein Collection," 4 pages (1997).
Scott, Bill, "Substructure Search," Dec. 2, 1997, pp. 1-51.
Substructure Search, pp. 1-30. (1997).
Derwent World Patents Index Search, pp. 20-26. (1997).
Abstract of EP 116,932 (1984).
Abstract of EP 676,395 (1995).
Abstract of EP 0 202 538 (1986).
Abstract of EP 16,371 (1980).
A "Notice of References Cited" from the USPTO for U.S. Appl. No. 08/995,749, filed Dec. 2, 1998, Inhibition of P38 Kinase Using Symmetrical and Unsymmetrical Diphenyl Ureas.
A "Notice of References Cited" from the USPTO for U.S. Appl. No. 09/083,399, filed Jan. 8, 2001, Inhibition of Raf Kinase Activity Using Aryl Ureas.
A "Notice of References Cited" from the USPTO for U.S. Appl. No. 09/425,228, filed Sep. 10, 2001, Inhibition of Raf Kinase Using Symmetrical and Unsymmetrical Substituted Diphenyl Ureas.
A "Notice of References Cited" from the USPTO for U.S. Appl. No. 09/425,229, filed Mar. 4, 2002, Omega-Carboxyl Aryl Substituted Diphenyl Ureas as P38 Kinase Inhibitors.
A "Notice of References Cited" from the USPTO for U.S. Appl. No. 09/458,015, filed Feb. 1, 2002, Inhibition of P38 Kinase Using Symmetrical and Unsymmetrical Diphenyl Ureas.
A "Notice of References Cited" from the USPTO for U.S. Appl. No. 09/472,232, filed Dec. 27, 1999, Inhibition of Raf Kinase Using Aryl and Heteroaryl Substituted Heterocyclic Ureas.
A "Notice of References Cited" from the USPTO for U.S. Appl. No. 09/773,604, filed Feb. 2, 2001, Publication No. US 2001-0034447-A1, Publication Date Oct. 25, 2001, Omega-carboxyaryl Substituted Diphenyl Ureas as Raf Kinase Inhibitors.
A "Notice of References Cited" from the USPTO for U.S. Appl. No. 09/773,659, filed Feb. 2, 2001, W-carboxyaryl Substituted Dipheny Ureas As Raf Kinase Inhibitors.
A "Notice of References Cited" from the USPTO for U.S. Appl. No. 09/773,672, filed Feb. 2, 2001, Publication No. US 2001-0016659 A1, Publication Date: Aug. 23, 2001, Omega-carboxyaryl substituted Diphenyl Ureas as Raf Kinase Inhibitors.
A "Notice of References Cited" from the USPTO for U.S. Appl. No. 09/773,675, filed Feb. 2, 2001, Publication No. US 2001-0011136-A1 , Publication Date: Aug. 2, 2001, Omega-Carboxyaryl Substituted Diphenyl Ureas as Raf Kinase Inhibitors.
A "Notice of References Cited" from the USPTO for U.S. Appl. No. 09/776,935, filed Dec. 22, 1998, Inhibition Of P38 Kinase Using Aryl and Heteroaryl Substituted Heterocyclic Ureas.
A "Notice of References Cited" from the USPTO for U.S. Appl. No. 09/776,936, filed Dec. 22, 1998, Inhibition of Raf Kinase Using Symmetrical and Unsymmetrical Substituted Diphenyl Ureas.
A "Notice of References Cited" from the USPTO for U.S. Appl. No. 09/777,920, filed Feb. 7, 2002, Omega-Carboxyaryl Substituted Diphenyl Ureas as Raf Kinase Inhibitors.
A "Notice of References Cited" from the USPTO for U.S. Appl. No. 09/948,915, filed Feb. 11, 2002, Omega-Carboxyaryl Substituted Diphenyl Ureas as Raf Kinase Inhibitors.
A "Notice of References Cited" from the USPTO for U.S. Appl. No. 10/042,226, filed Jan. 1, 2002, Omega Carboxyaryl Substituted Diphenyl Ureas as Raf Kinase Inhibitors.
Supplemental search report from the EPO for European application EP 98/963809 dated Mar. 30, 2001, Inhibition of Raf Kinase Using Symmetrical and Unsymmetrical Substituted Diphenyl Ureas, publication No. 1049664, publication date Nov. 8, 2002.
Supplemental search report from the EPO for European application EP 98/963810 dated Dec. 21, 2000, Inhibition of Raf Kinase Using Aryl and Heteroaryl Substituted Heterocyclic Ureas, publication No. 1056725, publication date Dec. 6, 2000.
Supplemental search report from the EPO for European application EP 98/965981 dated Dec. 21, 2000, Inhibition of Raf Kinase Using Substituted Heterocyclic Ureas, publication No. 1047418, publication date Nov. 2, 2000.
Supplemental search report from the EPO for European application EP 00/903239 dated Aug. 7, 2002, Omega-Carboxyaryl Substituted Diphenyl ureas as Raf Kinase Inhibitors.
International search report for International Application No. PCT/US98/52558, publication date Nov. 26, 1998.
International search report for International Application No. PCT/US98/10376 dated Jul. 30, 1998, Raf Kinase Inhibitors, publication No. WO 98/52559, publication date Nov. 26, 1998.
International search report for International Application No. PCT/US98/26078 dated Apr. 2, 1999, Inhibition of Raf Kinase Using Substituted Heterocyclic Ureas, publication No. WO99/32106, publication date Jul. 1, 1999.
International search report for International Application No. PCT/US98/26079 dated Apr. 12,1999, Inhibition of p38 Activity Using Aryl and Heteroaryl Substituted Heterocyclic Ureas, publication No. WO99/32110, publication date Jul. 1, 1999.
International search report for International Application No. PCT/US98/26080 dated Apr. 12, 1999, Inhibition of p38 Kinase Using Substituted Heterocyclic Ureas, publication No. WO99/32111, publication date Jul. 1, 1999.
International search report for International Application No. PCT/US98/26081 dated Apr. 2, 1999, Inhibition of Raf Kinase Using Symmetrical and Unsymmetrical Substituted Diphenyl Ureas, publication No. WO99/32436, publication date Jul. 1, 1999.
International search report for International Application No. PCT/US98/26082 dated May 12, 1999, Inhibition of Raf Kinase Using Aryl and Heteroaryl Substituted Heterocyclic Ureas, publication No. WO99/32455, publication date Jul. 1, 1999.

(56) References Cited

OTHER PUBLICATIONS

International search report for International Application No. PCT/US98/27265.
International search report for International Application No. PCT/US00/00648 dated Jun. 29, 2000, Omega-Carboxyaryl Substituted Diphenyl Ureas as Raf Kinase Inhibitors, publication No. WO00/42012A1, publication date Jul. 20, 2000.
International search report for International Application No. PCT/US00/00768 dated May 16, 2000, Omega-Carboxyl Aryl Substituted Diphenyl Ureas as P38 Kinase Inhibitors, publication No. WO00/41698A1, publication date Jul. 20, 2000.
International search report for International Application No. PCT/US02/12064 dated Sep. 20, 2002, Omega-Carboxypyridyl Substituted Dephenyl Ureas as Raf Kinase Inhibitors, publication No. 02/085859, publication date Oct. 31, 2002.
International search report for International Application No. PCT/US02/12066 dated Sep. 13, 2002, Inhibition of Raf Kinase Quinolyl, Isoquinolyl or Pyridyl Ureas, publication No. 02/085857, publication date Oct. 31, 2002.
International search report for International Application No. PCT/US/26081 dated Apr. 2, 1999, In'Hibition of Raf Kinase Using Symmetrical and Unsymmetrical Substituted Diphenyl Ureas, publication No. WO99/32436, publication date Jul. 1, 1999.
Co-pending U.S. Appl. No. 09/640,780, filed Aug. 18, 2000.
Co-pending U.S. Appl. No. 09/472,232, filed Dec. 27, 1999.
Co-pending U.S. Appl. No. 09/776,935, filed Dec. 22, 1998.
Co-pending U.S. Appl. No. 09/993,647, filed Nov. 27, 2001.
Co-pending U.S. Appl. No. 10/086,417, filed Mar. 4, 2002.
Co-pending U.S. Appl. No. 10/071,248, filed Feb. 11, 2002.
Co-pending U.S. Appl. No. 10/308,187, filed Dec. 3, 2002.
Co-pending U.S. Appl. No. 10/361,859, filed Feb. 11, 2003.
Co-pending U.S. Appl. No. 10/361,844, filed Feb. 11, 2003.
Co-pending U.S. Appl. No. 10/361,850, filed Feb. 11, 2003.
Co-pending U.S. Appl. No. 10/060,396, filed Feb. 1, 2002.
Co-pendng U.S. Appl. No. 10/125,369, filed Apr. 19, 2002.
Co-pending U.S. Appl. No. 09/889,227, filed Jul. 12, 2001.
XP-001145518 # 4956 Potent Raf Kinase Inhibitors from the Diphenylurea Class: Structure Activity Relationships, B. Riedl et al., Bayer Corporation.
XP-001145779 "Antitumor Activity of a C-raf Antisense Oligonucleotide in Combination with Standard Chemotherapeutic Agents against Various Human Tumors Transplanted Subcutaneously into Nude Mice," Thomas Geiger et al., vol. 3, 1179-1185, Jul. 1997.
XP-001145481 #2921 "Phase I and Pharmacokinetic Study of the Raf Kinase Inhibitor Bay 43-9006 in Patients with Locally Advanced or Metastic Cancer," Dirk Strumberg et al., Bayer AG.
XP-002232130, "A Phase I Trail of H-ras Antisense Oligonucleotide ISIS 2503 Administered as a Continuous Intravenous Infusion in Patients with Advanced Carcinoma," C. Casey Cunningham et al., 2001 American Cancer Society, vol. 92, No. 5, pp. 1265-1271.
XP-002233466, Medline/NLM, NLM8336809—[Intra-arterial ACNU, CDDP chemotherapy for brain metastases from lung cancer: comparison of cases with and without intra-arterial mannitol infusion], Iwadate Y et al.
Kurik et al., "Optical Properties of Segmented Oligourethane with Azomethine Terminal Fragments," Institute of Physics, National Academy of Sciences of Ukraine, 1996, pp. 2038-2041.
Nickel et al., "Carboxylic Acid Analogues of Suramin, Potential Filaricides," Indian Journal of Chemistry, Feb. 1991, vol. 30B, pp. 182-187.
Duam et al., "The Ins and Outs of Raf Kinases," TIBS Nov. 19, 1994, pp. 474-480.
Campbell et al., "Increasing Complexity of Ras Signaling," Oncogene, 1998, vol. 17, pp. 1395-1413.
Bolten et al., "Ras Oncogene Directed Approaches in Cancer Chemotherapy," Annual Reports in Medicinal Chemistry, vol. 29, pp. 165-174.
Moelling et al., "Signal Transuction as Target of Gene Therapy," Institute of Medical Virology, University of Zürich, Recent Results in Cancer Research, vol. 142, pp. 63-71.
Stein, Jay H., MD, Internal Medicine, $4^{th}$ Edition, 1994, pp. 699-715.
Bos et al., "Ras Oncogenes in Human Cancer: A Review," Cancer Research, Sep. 1, 1989, vol. 49, pp. 4682-4689.
Kempter et al., "Synthese potentieller Pflanzenschutz- und Schädlingsbekämpfungsmittel aus substituierten Anilinen," Pädagosische Hochschule, Eingegangen am Jan. 7, 1982, 101-120.
Lyons et al., "Discovery of a novel Raf Kinase Inhibitor," Endocrine-Related Cancer, 2001, vol. 8, pp. 219-225.
Lowinger et al., "Design and Discovery of Small Molecules Targeting Raf-1 Kinase," Current Pharmaceutical Design, 2002, vol. 8, pp. 2269-2278.
Dumas et al., "Recent Developments in the Discovery of Protein Kinase Inhibitors from the Urea Class," Current Opinion in Drug Discovery & Development, 2004, vol. 7, No. 5, pp. 600-616.
Dumas et al., "Protein Kinase Inhibitors from the Urea Class," Current Opinion in Drug Discover & Development, 2002, vol. 5, No. 5, pp. 718-727.
Lowinger et al., "Discovery of Novel Class of Potent Raf Kinase Inhibitors: Structure Activity Relationships," Clinical Cancer Research, Nov. 2000, vol. 6, pp. 4533s.
Hotte et al., "BAY 43-9006: Early Clinical Data in Patients with Advanced Solid Malignancies," Current Pharmaceutical Design, 2002, vol. 8, pp. 2249-2253.
Lee et al., "BAY-43-9006: Bayer/Onyx," Current Opinion in Investigational Drugs, 2003, vol. 4, pp. 757-763.
Sorbara et al., "BAY-43-9006," Drugs of the Future, 2002, vol. 27, No. 12, pp. 1141-1147.
Khire et al., "Omega-Carboxypyridyl Substituted Ureas as Raf Kinase Inhibitors: SAR of the Amid Substituent," Bioorg. Med. Chem. Lett., 2004, vol. 14, pp. 783-786.
Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis," Cancer Research., Oct. 1, 2004, vol. 64, pp. 7099-7109.
Smith, et al., "Discovery of Heterocyclis Ureas as a New Class of Raf Kinase Inhibitors: Identification of a Second Generation Lead by a Combinatorial Chemistry Approach." Bioorganic & Medicinal Chemistry Letters, 2001, vol. 11, pp. 2775-2778.
Bankston et al., "A Scaleable Synthesis of BAY 43-9006: a Potent Raf Kinase Inhibitor for the Treatment of Cancer," Organic Process Research & Development, 2002, vol. 6, pp. 777-781.
Strumberg et al., "Results of Phase I Pharmacokinetic and Pharmacodynamic Studies of the Raf Kinase Inhibitor BAY 43-9006 in Patients with Solid Tumors," International Journal of Clinical Pharmacology and Therapeutics, 2002, vol. 40, No. 12, pp. 580-581.
Chang et al., "BAY 43-9006 (Sorafenib) Inhibitors Ectopic (s.c.) and Orthotopic Growth of a Murine Model of Renal Adenocarcinoma (Renca) Predominantly Through Inhibition of Tumor Angiogenesis," $96^{th}$ Annual Meeting, Anaheim/Orange County, CA, Apr. 16-20, 2005.
Panka et al., "BAY 43-9006 Induces Apoptosis in Melanoma Cell Lines," $96^{th}$ Annual Meeting, Anaheim/Orange County, CA, Apr. 16-20, 2005.
Auclair, et al., "BAY 43-9006 (Sorafenib) is a Potent Inhibitor of FLT3 Tyrosine Kinase Signaling and Proliferation in AML cells," $96^{th}$ Annual Meeting, Anaheim/Orange County, CA, Apr. 16-20, 2005.
Murphy et al., "BAY 43-9006 Controls Tumor Growth Through Inhibition of Vascular Development," $96^{th}$ Annual Meeting, Anaheim/Orange County, CA, Apr. 16-20, 2005.
Spronsen et al., "Novel Treatment Strategies in Clear-Cell Metastatic renal Cell Carcinoma," Anti-Cancer Drugs, 2005, vol. 16, pp. 709-717.
Thaimattam et al., "3D-QSAR CoMRFA, CoMSIA Studies on Substituted Ureas as Raf-1 Kinase Inhibitors and Its Confirmation with Structure-Based Studies," Bioorganic & Medicinal Chemistry, 2004, vol. 12, pp. 6415-6425.
Danson et al., "Improving Outcomes in Advanced Malignant Melanoma," Drugs, 2005, vol. 65, No. 6, pp. 733-743.

(56) References Cited

OTHER PUBLICATIONS

Heim et al., "Antitumor Effect and Potentiation or Reduction in Cytotoxic Drug Activity in Human Colon Carcinoma Cells by the Raf Kinase Inhibitor (RKI) BAY 43-9006," International Journal of Clinical Pharmacology and Therapeutics, 2003, vol. 41, No. 12, pp. 616-617.
Richly et al., "Results of a Phase I Trial of BAY 43-9006 in Combination with Doxorubicin in Patients with Primary Hepatic Cancer," International Journal of Clinical Pharmacology and Therapeutics, 2004, vol. 42, No. 11, pp. 650-651.
Mross et al., "Drug-drug Reaction Pharmacokinetic Study with the Raf Kinase Inhibitor (RKI) BAY 43-9006 Administered in Combination with Irinotecan (CPT-11) in Patients with Solid Tumors," International Journal of Clinical Pharmacology and Therapeutics, 2003, vol. 41, No. 12, pp. 618-619.
Richly et al., "A Phase I Clinical and Pharmacokinetic Study of the Raf Kinase Inhibitor (RKI) BAY 43-9006 Administered in Combination with Doxorubicin in Patients with Solid Tumors," International Journal of Clinical Pharmacology and Therapeutics, 2003, vol. 41, No. 12, pp. 620-621.
DeGrendele, "Activity of the Raf Kinase Inhibitor BAY 43-9006 in Patients with Advanced Solid Tumors," Clinical Colorectal Cancer, May 2003, pp. 16-18.
Hubbard, "Oncogenic Mutations in B-Raf: Some Losses Yield Gains," Skirball Institute of Biomolecular Medicine and Department of Pharmacology, New York University School of Medicine, New York, NY.
Thompson et al., "Recent Progress in Targeting the Raf/MEK/ERK Pathway with Inhibitors in Cancer Drug Discovery," Curr. Opin. Pharmacol., Aug. 2005, vol. 5, No. 4, pp. 350-356.
Moore et al., "Phase I Study to Determine the Safety and Pharmacokinetics of the Novel Raf Kinase and VEGFR Inhibitor BAY 43-9006, Administered for 28 days on/7 days off in Patients with Advanced, Refractory Solid Tumors," Annals of Oncology, 2005, vol. 16, pp. 1688-1694.
Ahmad et al., "Kinase Inhibition with BAY 43-9006 in Renal Cell Carcinoma," Clinical Cancer Research, Sep. 15, 2004, vol. 10, pp. 6388s-6392s.
Wan et al., "Mechanism of Activation of the RAF-ERK Signaling Pathway by Oncogenic Mutations of B-RAF," Cell, Mar. 19, 2004, vol. 116, pp. 855-867.
XP-002086152, Hanson et al., "Pulmonary-Allergy, Dermatological, Gastrointestinal & Arthritis, Inhibitors of p38 Kinase," Exp. Opin. Ther. Patents, 1997, vol. 7, No. 7, pp. 729-733.
Strumberg et al., "Phase I Clinical and Pharmacokinetic Study of the Novel Raf Kinase and Vascular Endothelial Growth Factor Receptor Inhibitor BAY 43-9006 in Patients with Advanced Refractory Solid Tumors," Journal of Clinical Oncology, Feb. 10, 2005, vol. 23, No. 5, pp. 965-972.
Regan et al., "Pyrazole Urea-Based Inhibitors of p38 MAP Kinase: from Lead Compound to Clinical Candidate," J. Med. Chem., 2002, vol. 45, pp. 2994-3008.
Clark et al., "Safety and Pharmacokinetics of the Dual Action Raf Kinase and Vascular Endothelial Growth Factor Receptor Inhibitor, BAY 43-9006, in Patients with Advanced, Refractory Solid Tumors," Clinical Cancer Res., Aug. 1, 2005, vol. 11, No. 5, pp. 5472-5480.
XP-002103155, Wilson et al., "The Structural Basis for the Specificity of Pyridinylimidazole Inhibitors of p38 MAP Kinase," Chemistry & Biology, 1997, vol. 4, No. 6, pp. 423-431.
Jeffcoat et al., "The Metabolism and Toxicity of Halogenated Carbanilides," Drug Metabolism and Deposition, vol. 5, No. 2, pp. 157-166.
XP-000973679, Murata et al., "Facile Synthesis of New Pyrrolo[3,4-d]Pyrimidine-2,4-Diones," Chemical and Pharmaceutical Bulletin, 1974, vol. 22, No. 5, pp. 1212-1213.
Hanson, "Inhibitors of p38 Kinase," Expert Opinion on Therapeutic Patents, Jul. 1997, vol. 7, No. 7, pp. 729-733(5).
Garcia-Lopez et al., "New routes for the Synthesis of Pyrrolo[3,2-d]- and [2,3-d]- Pyrimidine Systems Starting from a Common Pyrrole Derivative," Journal of the Chemical Society, Perkin Transactions 1: Organic and Bio-Organic Chemistry (1972-1999), 1978, pp. 483-487.
Wilhelm et al., "BAY 43-9006: Preclinical Data," Curr Pharm Des, 2002, vol. 8, No. 25, pp. 2255-2257.
Wright et al., "Clinical Trials Referral Resource. Current Clinical Trials of BAY 43-9006, Part 1," Oncology, Apr. 19, 2005, vol. 4: pp. 499-502.
02-022650, Patent Abstracts of Japan, Jan. 25, 1990.
02-023337, Patent Abstracts of Japan, Jan. 25, 1990.
XP-000676688, WisSner et al., "Analogues of Platelet Activating Factor. 7. Bis-Aryl Amide and Bis-Aryl Urea Receptor Antagoinist of PAF," J. Med. Chem., 1992, vol. 35, pp. 4779-4789.
Ravi et al., "Activated RAF-1 Causes Growth Arrest in Human Small Cell Lung Cancer Cells," J. Clinical. Investigation, pp. 153-159.
Lemoine, "Overview of ras oncogenes and their clinical potential," Chapter 10, pp. 85-91.
Drug: Facts and Comparisons, 1994 Edition, pp. 2703-2705.
828, Siu et all, "Phase I Study of Oral RAF-1 Kinase Inhibitor BAY 43-9006 with Gemcitabine in Patients with Advanced Solid Tumors," Proc Am Soc Clinic Oncology, 2003, vol. 22, pp. 207.
4510, Escudier et al., "Randomized phase III trial of the raf kinase and VEGFR inhibitor sorafenib (BAY 43-9006) in patients with advanced renal cell carcinoma (RCC)," Meeting: 2005 ASCO Annual Meeting, Category: Genitourinary Cancer, Subcategory: Kidney Cancer.
7508, Eisen et al., "Phase I trial of BAY 43-9006 (Sorafenib) Combined with Dacarbazine (DTIC) in Metastatic Melanoma Patients," Meeting: 2005 ASCO Annual Meeting, Category: Melamona, Subcategory: Melamona.
4510, Adjei et al., "A Phase I Study of BAY 43-9006 and Gefitinib in Patients with Refractory or Recurrent Non-Small-Cell Lung Cancer (NSCLC)," Meeting: 2005 ASCO Annual Meeting, Category: Developmental Therapeutics: Molecular Therapeutics, Subcategory: Antiangiogenic or Antimetastatic agents.
XP-001093697, Carling et al., "1-(3-Cyanobenzylpiperidin-4-yl)-5-Methyl-4-Phenyl-1,3-Dihydroimidazol-2-One: A Selective High-Affinity Antagonist for the Human Dopamine $D_4$ Receptor with Excellent Selectivity over Ion Channels," J. Med. Chem., 1999, vol. 42, pp. 2706-2715.
XP-002147879, Muijlwijk-Koezen et al., "Isoquinoline and Quinazoline Urea Analogues as Antagonists for the Human Adenosine $A_3$ Receptor," J. Med. Chem., 2000, vol. 43, pp. 2227-2238.
XP-001062441, Eisenhauer et al., "Impact of New Non-Cytotoxics in the Treatment in Ovarian Cancer," Inernational J. Gynecol Cancer, 2001, vol. 11, Supplement 1, pp. 68-72.
913, XP-001152608, Kubo et al., "Synthesis and Structure-Activity Relationship of Quinazoline-Urea Derivatives as Novel Orally Active VEGF Receptor Tyrosine Kinase Selective Inhibitors," Proceedings of the American Association of Cancer Res., 2002, vol. 43, p. 182.
4954, XP-001145482, Carter et al., "Anti-tumor Efficacy of the Orally Active RAF Kinase Inhibitor Bay 43-9006 in Human Tumor Xenograft Models," Proceedings of he American Association for Cancer Res., 2001, vol. 42, p. 923
2921, XP-00114481, Strumberg et al., "Phase I and Pharmacokinetic Study of the RAF Kinase Inhibitor Bay 43-9006 in Patients with Locally Advanced or Metastatic Cancer," Bayer AG.
Dumas et al., "1-Phenyl-5-Pyrazolyl Ureas: Potent and Selective p38 Kinase Inhibitors," Bioorganic & Medicinal Chemistry Letters, 2000, vol. 10, pp. 2051-2054.
4956, XP-001145518, Riedl et al., "Potent Raf Kinase Inhibitors from the Diphenylurea Class: Structure Activity Relationships," Bayer Corporation.
Iwadate et al., "Intra-Arterial ACNU, CDDP Chemotherapy for Brain Metastases from Lung Cancer: Comparison of Cases With and Without Intra-Arterial Mannitol Infusion," Department of Neurological Surgery, Chiba Cancer Center Hospital, Clinical Trial, Journal Article Randomized Controlled Trial, No Shinkei Geka, 1993, vol. 21, No. 6, pp. 513-518.
XP-001145779, Geiger et al., "Antitumor Activity of a C-raf Antisense Oligonucleotide in Combination with Standard Chemo-

(56) References Cited

OTHER PUBLICATIONS therapeutic Agents against Various Human Tumors Transplanted Subcutaneously into Nude Mice," Clinical Cancer Research, Jul. 1997, vol. 3, pp. 1179-1185.
XP-002232130, Cunningham et al., "A Phase I Trial of H-ras Antisense Oligonucleotide ISIS 2503 Administered as a Continuous Intravenous Infusion in Patients with Advanced Carcinoma," American Cancer Society, Sep. 2001, vol. 92, No. 5, pp. 1265-1271.
Blanco et al., "p38 MAPK Signaling Cascades: Ancient Roles and New Functions," Bioassays, 2000, vol. 22, pp. 637-645.
Madwed et al., "Pharmacological Evaluation of BIRB 796, a Selective Inhibitor of p38 MAP Kinase (MAPK), IN Animal Models of Endotoxic Shock, Inflammation and Arthritis," Inflammation Res., 2001, vol. 50, p. S184.
Ridley et al., "Actions of IL-1 are Selectively Controlled by p38 Mitogen-Activated Protein Kinase, Regulation of Prostaglandin H Synthase-2, Metalloproteinases, and IL-6 at Different Levels," The Journal of Immunology, 1997, vol. 158, pp. 3165-3173.
Wild, Hanno, "Substructure #1," 1996, pp. 1-107.
Canetta et al., "Carboplatin: current status and future prospects," 1998, p. 17-32.
Ozols, "New Developments With Carboplatin in the Treatment of Ovarian Cancer," Seminars in Oncology, vol. 19, No. 1, Supplement 2, Feb. 1992, pp. 85-89.
Rowinsky et al., "Taxol: The First of the Taxanes, an Important New Class of Anitumor Agents," Seminars in Oncology, vol. 19, No. 6, Dec. 1992, pp. 646-662.
Rowinsky et al., "Sequences of Taxol and Cisplatin: A Phase I and Pharmacologic Study," Journal of Clinical Oncology, vol. 19, No. 9, Sep. 1991, pp. 1692-1703.
Raez et al., "New Developments in chemotherapy for advanced non-small lung cancer," Current Opinion in Oncology, vol. 18, 2006, pp. 156-161.
Cortes et al., "Targeting the Microtubules in Breast Cancer Beyond Taxanes: The Epothilones," The Oncologist, 2007, vol. 12, pp. 271-280.
Bergstralh et al., "Microtubule stabilising agents: Their molecular signaling consequences and the potential for enhancement by drug combination," Cancer Treatment Reviews, 2006, vol. 32, pp. 166-179.
Kempter et al.,"Synthesis of potential plant protective agents and pesticides from . . . ," 1983, vol. 27, Issue 1, pp. 101-120.
"795 Oral Phase II trail of sorafenib (BAY 43-9006) in combination with interferon alpha 2b in patients with metastatic renal cell carcinoma", European Journal of Cancer, 2005, vol. 3, No. 2, pp. 226-227.
"883 Poster Phase I trial of sorafenib (BAY 43-9006) in combination with interferon alpha-2a in patients with unresectable and/or metastatic renal cell carcinoma and malignant melanoma", European Journal of Cancer, 2005, vol. 3, No. 2, p. 254.
Bando et al., "Association between intratumoral free and total VEGF, soluble VEGFR-1, VEGFR-2 and prognosis in breast cancer" British Journal of Cancer, 2005, vol. 92, pp. 553-561.
Carlomagno et al., "BAY 43-9006 Inhibition of Oncogenic RET Mutants", Journal of the National Cancer Institute, 2006, vol. 98, No. 5, pp. 326-334.
Chang et al., "Sorafenib (BAY 43-9006) inhibits tumor growth and vascularization and induces tumor apoptosis and hypoxia in RCC xenograft models" Cancer Chemother Pharmacol, 2007, vol. 50, pp. 561-574.
Foekens et al., "High Tumor Levels of Vascular Endothelial Growth Factor Predict Poor Response to Systemic Therapy in Advanced Breast Cancer," Cander Research, 2001, vol. 61, pp. 5407-5414.
Forbes et al., "N-(1-Methyl-5-indolyl)-N'-(3-methyl-5-isothiazolyl)urea: A Novel, High-Affinity 5-HT$_{2B}$ Receptor Antagonist" Journal of Medicinal Chemistry, 1995, vol. 38, No. 6, pp. 854-857.
Gomez-Esquer et al., "mRNA expression of the angiogenesis markers VEGF and CD105 (endoglin) in human breast cancer," US National Library of Medicine, 2004, vol. 24, No. 3a, pp. 1581-1585, XP002455577.

Gura, "Systems for identifying new drugs are often faulty." Science, 1997, vol. 278 (5340), pp. 1041-1042.
Heim et al., The Raf kinase inhibitor BAY 43-9006 reduces celluar uptake of platinum compounds and cytotoxity in human colorectal carcinoma cell lines', Anti-Cancer Drugs, 2005, vol. 16, pp. 129-136.
Quinglong et al., "Soluble Vascular Endothelial Growth Factor Receptor 1, and Not Receptor 2, Is an Independent Prognostic Factor in Acute Myeloid Leukemia and Myelodysplastic Syndromes," Wiley InterScience, 2004, vol. 100, No. 9, pp. 1884-1891.
Dumas et al., "Synthesis and Pharmacological Characterization of a Potent, Orally Active p38 Kinase Inhibitor," Bioorganic & Medicinal Chemistry Letters, 2002, vol. 12, pp. 1559-1562.
Johnson et al., "Relationships between drug activity in NCI preclinical in vitro and in vivo models and early clinical trials," British Journal of Cancer, 2001, vol. 84, No. 10, pp. 1424-1431.
Kuefer et al., "Translational research in renal cell cancer. Illustrated by the example of the vascular endothelial growth factor pathway," Der Urologe, 2006, vol. 45, No. 3, pp. 328, 330-335.
Leuner et al., "Inmproving drug solubility for oral delivery using solic dispersions," European Journal of Pharmaceutics and Biopharmaceutics.
Luo et al., "Enhancement of radiation effects by pXLG-mENDO in a lung carcinoma model," I.J. Radiation Oncology Biology Physics, 2005, vol. 63, No. 2, pp. 553-564.
Shi et al., "Constitutive and Inducible Interleukin 8 Expression by Hypoxia and Acidosis Renders Human Pancreatic Cancer Cells More Tumorigenic and Metastatic," Clinical Cancer Research, 1999, vol. 5, pp. 3711-3721.
Veronese et al., "Mechanisms of Hypertension Associated with BAY 43-9006," Journal of Clinical Oncology, 2006, vol. 24, No. 9, pp. 1363-1369.
XU et al., "Hypoxia-induced Elevation in Interleukin-8 Expression by Human Ovarian Carcinoma Cells," Cancer Research, 1999, vol. 59, pp. 5822-5829.
Elting et al., "Biomarkers associated with clinical outcomes in Targets, a Phase III single-agent, placebo-controlled study of sorafenib in advanced renal cell carcinoma," Proc Amer Assoc Cancer Res, 2006, vol. 47, Abstract #2909.
Flaherty et al., "Phase I/II trial of BAY 43-9006, carboplatin (C) and paclitaxel (P) demonstrates preliminary antitumor activity in the expansion cohort of patients with metastatic melanoma," *Journal of Clinical Oncology*, 2004, vol. 22, No. 14S, Abstract.
Guido et al., "International Melanoma Research Congress—Foundation for Melanoma Research ," Idrugs, 2003, vol. 6, No. 8, pp. 752-754, ISSN 1369-7056.
Pending claims of U.S. Appl. No. 12/421,690, filed Apr. 10, 2009.
Pending claims of U.S. Appl. No. 12/092,024, filed Apr. 29, 2008.
Pending claims of U.S. Appl. No. 12/093,515, filed May 13, 2008.
Pending claims of U.S. Appl. No. 12/093,719, filed May 15, 2008.
Pending claims of U.S. Appl. No. 12/095,611, filed May 30, 2008.
Pending claims of U.S. Appl. No. 12/520,618, filed Jun. 22, 2009.
Pending claims of U.S. Appl. No. 12/520,609, filed Jun. 22, 2009.
Pending claims of U.S. Appl. No. 12/294,979, filed Sep. 29, 2008.
"Weekly Epidemiological Record." World Health Organization. Apr. 1999; vol. 14,111-112.
A. A. Sinkula et al.: "Rationale for Design of Biologically Reversible Drug Derivatives: Prodrugs," Journal of Pharmaceutical Sciences, vol. 64, No. 2, Feb. 1975, pp. 181-210.
A. Arnone et al.: "Selectivities in the Oxidation of Tertiary Amines and Pyridine Derivatives by Perfluoro Cis-2,3-Dialkyloxaziridines," Tetrahedron, vol. 54, 1998, pp. 7831-7842.
A. Bellacosa et al.; "Molecular Alterations of the Akt2 Oncogene in Ovarian and Brest Carcinomas," Int. J. Cancer, vol. 64, 1995, pp. 280-285.
Balant, L.P. et al.: "Metabolic Considerations in Prodrug Design." Burger's Medicinal Chemistry and Drug Discovery, 5$^{th}$ ed. John Wiley, New York, 1995: vol. 1, 949-982.
Banerjee, Sangeeta, et al. "Murine Coronavirus Replication-induced p 38 Mitogen-Activated Protein Kinase Activation Promotes Interleukin-6 Production and Virus Replication in Cultured Cells." Journal of Virology. American Society for Microbiology, 2002: vol. 76, 5937-5948.

(56) References Cited

OTHER PUBLICATIONS

Berge, Stephen M, Lyle D. Bighley, and Donald C. Monkhouse. "Pharmaceutical Salts." The Journal of Pharmaceutical Science. Jan. 1997:1-19, vol. 66, No. 1.
Bertrand, F. E. et al., "Inhibition of PI3K, mTOR and MEK Signaling Pathways Promotes Rapid Apoptosis in B-Lineage ALL in the Presence of Stromal Cell Support", Leukemia (Basingstoke), vol. 19, No. 1, Jan. 2005; pp. 98-102, XP002402153, ISSN: 0887-6924, Abstract.
Boyd, Derek R., et al. "Arene Oxides of Quinoline: Epoxidation, N-Oxidation and N-Methylation Reactions." Journal of Chemistry Social. Perkin Trans, 1991: vol. 9, 2189-2192.
Bundgaard, Hans. "Design of Prodrugs." Elsevier Science, New York, 1985.
C. J. Vlahos et al.: "A Specific of Phosphatidylinositol 3-Kinase, 2-(-4-Morpholinyl)-8-Phenyl-4H-1-Benzopyran-4-One (LY294002)," The Journal of Biological Chemistry, vol. 269, No. 7, Feb. 18, 1994, pp. 5241-5248.
Carey, Francis A. and Richard J. Sundberg. "Part A: Structure and Mechanisms." Advanced Organic Chemistry, $2^{nd}$ Ed. Plenum Press, New York, 1984.
Chen, Chun-Jung et al. "Suppression of Japanese Encephalitis Virus Infection by Non-Steroidial, Anti-Inflammatory Drugs." Journal of General Virology. 2002. 1897-1905.
Chen, Jiping and Mark F. Stinski. "Role of Regulatory Elements and the MAPK/ERK or P38 MAPK Pathways for Activation of Human Cytomegalovirus Gene Expression." Journal of Virology, 2002: 4873-4885.
Coperet, Christophe, et al. "A Simple and Effcient Method for the Preparation of Pyridine-N-Oxides II." Tetrahedron Letters. Elsevier Science Ltd. Pergamon Press, Oxford, UK 1998: vol. 30, 761-764.
Denny, William A. "Prodrug Strategies in Cancer Therapy." European Journal of Medicinal Chemistry. 2001: vol. 36, 577-595.
E. B. Roche: "Structural Aspects of Selective Distribution," American Pharmaceutical Association, Washington, D.C., 1977, pp. 27-46.
E. J. Meuillet er al.: "In Vivo Molecular Pharmacology and Antitumor Activity of the Targeted Akt Inhibitor PX-316," Oncology Research, vol. 14, 2004, pp. 513-527.
El-Deiry, Wafik S., "Meeting Report: The International Conference on Tumor Progression and Therapeutic Resistance", Cancer Research, Jun. 2005; vol. 65, No. 11, pp. 4475-4484, XP002402154, ISSN: 0008-5472, p. 4476.
F. H. Sarkar et al.: "Indole-3-Carbinol and Prostrate Cancer" The Journal of Nutrition 134, 2004, pp. 3493-3498.
Paquette, Leo A. The Encyclopedia of Reagents for Organic Synthesis, John Wiley, New York, 1994.
G. J. Robke et al: "Conversion of Aminopyridines into N-Oxides by Caro's Acid Anion (Peroxymonosulfate)," J. Chem. Research (S), 1993, pp. 412-413.
G. P. Dasmahapatra et al.: "In Vitro Combination Treatment WI6TH Perifosine and UCN-01 Demonstrates Synergism Against Prostate (PC-2) and Lung (A549) Epithelial Adenocarcinoma Cell Lines," Clinical Cancer Research, vol. 10, Aug. 1, 2004, pp. 5242-5252.
G. Tabellini et al.: "Novel 2'Substituted, 3'-Deoxy-Phosphatidyl-Myo-Inositiol Analogues Reduce Drug Resistance in Human Leukaemia Cell Lines With an Activated Phosphoinositide 3-Kinase/Akt Pathway," British Journal of Haematology, 126, 2004, pp. 574-582.
Gennaro, Alfonso R. "The Science and Practice of Pharmacy, $20^{th}$ Ed." Remington. Lippincott Williams & Wilkins, 1986.
Giambartolomei, S, et al. "Sustained Activation of the RAF/MEK/ERK Pathway in Response to EGF in Stable Cell Lines Expressing the Hepatitis C Virus (HCV) Core Protein." Oncogene. Nature Publishing Group, 2001: vol. 20, 2606-2610.
Greene, T.W. and Peter G.M. Wuts. Protective Groups in Organic Synthesis, $3^{rd}$ Ed., John Wiley, New York, 1999.
Guan Y., et al. "H5N1 Influenza: A Protean Pandemic Threat." Proceedings of the National Academy of Science. May 25, 2004; vol. 101, 8156-8161.

Han, Hyo Kyung and Gordon L. Amidon. "Targeted Prodrug Design to Optimize Drug Delivery." AAPS Pharmsci. 2000: vol. 2, No. 1, Article 6, 1-11.
Hansch, Corwin, Peter Sammes, and John B. Taylor. Comprehensive Medicinal Chemistry. Pregamon Press, Oxford, UK, 1990.
Hegedus, L.S. "Transition Metals in the Synthesis of Complex Organic Molecules." University Science Books, Mill Valley, California, 1994.
Higuchi T. et al., "Prodrugs as Novel Drug Delivery Systems." ACS Symposion Series, American Chemical Society, Washington, DC, 1975.
Hirasawa, Kensuke, et al. "Effect of p38 Mitogen-Activated Protein Kinase on the Replication of Encephalomyocarditis Virus." The Journal of Virology. May 2003: 5649-5656.
I. Vivanco et al.: "The Phosphatidylinositol 3-Kinase-Akt Pathway in Human Cancer," Nature Reviews Cancer, vol. 2, Jul. 2002. pp. 489-501.
J. Downward: "Mechanisms and Consequences of Activation of Protein Kinase B/Akt," Current Opinion in Cell Biology, vol. 10, 1998, pp. 262-267.
J. Gills et al.: "The Development of Phosphatidylinositol Ether Lipid Analogues as Inhibitors of the Serine/Theronine Kinas,Akt," Expert Opinion Investig. Drugs, vol. 13, No. 7, 2004, pp. 787-797.
J. H. Markgraf et al.: "Strained Heterocyclic Systems. 19. 1-Azatriptycene and Derivatives," Tetrahedron, vol. 47, No. 2, 1991, pp. 183-188.
J. Zhu et al.: "From the Cyclooxigenase-2 Inhibitor Celecoxib to a Novel Class of 3-Phosphoinositide-Dependent Protein Kinase-1 Inhibitors," Cancer Research 64, Jun. 15, 2004, pp. 4309-4318.
Johnston, D, et al., "Elevation of the Epidermal Growth Factor Receptor and Dependent Signaling in Human Papillomavirus-infected Laryngeal Papillomas." Cancer Research, 1999: 968-974.
K. M. Nicholson et al.: "The Protein Kinase B/Akt Signaling Pathway in Human Malignancy," Cellular Signalling 14, 2004, pp. 381-395.
Pavlovic-Lazetic, Gordana, Nenad Mitic, and Milos Beljanski. Bioinformatics Analysis of SARS Coronavirus Genome Polymorphism. May 25, 2004: 1-14.
Katritzky, Alan R, Charles W. Rees, and Walter Lwowski. "The Structure, Reactions, Synthesis, and Uses of Heterocyclic Compounds." Comprehensive Heterocyclic Chemistry. Pergamon Press, Oxford, UK, 1984.
Katritzky, Alan R. "Synthesis: Carbon with No Attached Heteroatoms." Comprehensive Organic Functional Group Transformations. Pergamon Press, Oxford, UK, 1995.
Kessler, Nicole, et al. "Use of the DNA Flow-Thru Chip, a Three-Dimensional Biochip, for Typing and Subtyping of Influenza Viruses." Journal of Clinical Microbiology. May 2004: vol. 42, 2173-2185.
Motzer et al., "Survival and Prognostic Stratification of 670 Patients With Advanced Renal Cell Carcinonma", J. Clin. Onc., 17(8): 2530-2540 (1999).
Muthumani, Karuppiah, et al. "Suppression of HIV-1 Viral Replication and Cellular Pathogensis by a Novel p38/JNK Kinase Inhibitor." AIDS. Lippincott Williams & Wilkins, 2004: vol. 18, 739-748.
N.T. Ihle et al.: "Molecular Pharamcology and Antitumor Activity of PX-866, A Novel Inhibior of Phosphoinositide-3-Kinas Signaling," Molecular Cancer Therapy, vol. 3, No. 7, 2004, pp. 763-772.
P. Amornphimolthan et al.: "Persistent Activation of the Akt Pathway in Head and Neck Squamous Cell Carcinoma: A Potential Target for UCN-01," Clinical Cancer Research, vol. 10, Jun. 15, 2004, pp. 4029-4037.
Panteva, Milena, Hasan Korkaya, and Shahid Jameel. "Hepatitis Viruses and the MAPK Pathway: Is This a Survival Strategy?" Virus Research. Elsevier Science Ltd, New York, 2003: 131-140.
S. Barnett et al.: "Identification and Characterization of Pleckstrin-Homology-Domain-Dependent and Isoenzyme-Specific Akt Inhibitors," Biochem J., vol. 385, 2005, pp. 399-408.
S. Dayan et al.: "Tertiary Amine Oxidation Using HOF•CH$_3$CN: A Novel Synthesis of N-Oxides," Synthesis, 1999, No. SI, pp. 1427-1430.
Shelton, John G. et al., "Effects of the RAF/MEK/ERK and PI3K/Akt Signal Transduction Pathways on the Abrogation of Cytokine-De-

(56) References Cited

OTHER PUBLICATIONS pendence and Prevention of Apoptosis in Hematopoietic Cells", Oncogene, vol. 22, No. 16, Apr. 2003; pp. 2478-2492; XP002402152 ISSN: 0950-9232, p. 2489.
Stahl, Jill M., et al; "Deregulated Akt3 Activity Promotes Development of Malignant Melanoma"; Cancer Research, vol. 64, No. 19; Oct. 2004; pp. 7002-7010, XP002402151, ISSN: 0008-5472, p. 7002.
Swart, Guido W.M.; "International Melanoma Research Congress—Foundation for Melanoma Research, Jun. 2003"; IDRUGS: The Investigational Drugs Journal, Aug. 2003; pp. 752-754; XP002402150 ISSN: 1369-7056, p. 754.
T. Lee et al.: "FTY720 Induces Apoptosis of Human Hepatoma Cell Lines Through P13-K-Mediated Akt Dephophorylation," Carcinogenesis, vol. 25, No. 12, 2004, pp. 2397-2405.
V. J. Stella et al.: "Prodrugs and Site-Specific Drug Delivery," Journal of Medicinal Chemistry, vol. 23, No. 12, Dec. 1980, pp. 1275-1282.
V. J. Stella et al: "Prodrugs Do they Have Advantages in Clinical Practice?" Drugs, Vo. 29, 1985, pp. 455-473.
X. Jin et al.: "Inhibition of Akt Survival Pathway by a Small Molecule Inhibitor in Human Endometrial Cancer Cells," British Journal of Cancer, vol. 91, 2004, pp. 1808-1812.
Roche, E.B. "Designs of Biopharmaceutical Properties Through Prodrugs and Analogs." American Pharmaceutical Association, Washington, D.C. 1977: 27-46.
Roman, Ann, and Kenneth H. Fife. "Human Papillomaviruses: Are We Ready to Type?" Clinical Microbiology Reviews. Apr. 1989: vol. 2, 166-190.
Robertson, et al. "Science's Compass." Science—New York then Washington. 2000: vol. 288, 55-57.
Stock, Lars, et al. "Integrity of c-Raf-1/MEK Signal Transduction Cascade is Essential for Hepatitis B Virus Gene Expression." Oncogene. Nature Publishing Group, 2003: vol. 22, 2604-2610.
Sturm-Ramirez, K.M. et al. "Reemerging H5N1 Influenza Viruses in Hong Kong in 2002 Are Highly Pathogenic to Ducks." (Journal of Virology0, May 2004, 4892-4901, 78:9.
Robertson, D. L. et al. "HIV-1 Nomenclature Proposal." (Science), Apr. 7, 2000,55-57, 288.
Yeh, S.H. et al. "Characterization of severe acute respiratory syndrome cornavirus genomes in Taiwan: Molecular epidemiology and genome evolution evolution." (PNAS), Feb. 24, 2004, 2542-2547, 101:8.
Zhao, Z. et al. "Moderate mutation rate in the SARS coronavirus genome and its implications." (BMC Evolutionary Biology), 2004, 4:21.
Katritzky, A.R. and C.W. Rees. "Comprehensive Heterocyclic Chemistry II, A Review of the Literature 1982-1995: The Structure, Reactions, Synthesis, and Uses of Heterocyclic Compounds." Pergamon Press, Oxford, UK, 1996.
Swarbick, J. and J.C. Boylan, "Encyclopedia of Pharmaceutical Technology." $2^{nd}$ Edition, Marcel Dekker, 2002.
Trost, B.M. and I. Fleming. "Comprehensive Organic Systems: Selectivity, Strategy & Efficiency in Modern Organic Chemistry." Pergamon Press, Oxford, UK. 1991.
Wilkinson. Geoffrey. "The Synthesis, Reactions, and Structures of Organometallic Compounds." Comprehensive Organometallic Compounds. Pergamon Press, Oxford, U.K. 1982: vol. 1.
Wright, S.M., A. Mleczko, and K.S. Coats. "Bovine Immunodeficiency Virus Expression in Virtro is Reduced in the Presence of Beta-Chemokines, MIP-1 alpha, MIP-1 beta and Rantes." Veterinary Research Communications. 2002: 239-250.
Yang, Hailin et al. << Antiviral Chemotherapy Facilities Control of Proxvirus Infections Through Inhibition of Cellular Signal Transduction. >> The Journal of Clinical Investigation. 2005: 379-387.
Zachos, George, Barklie Clements, and Joe Conner. "Herpes Simplex Virus Type 1 Infection Stimulates p38/c-Jun N-terminal Mitogen-activated Protein Kinase Pathways and acticates Transcription Factor AP-1." Journal of Biological Chemistry. The American Society for Biochemistry and Molecular Biology, Inc. 1999: vol. 274, 5097-5103.

U.S. Appl. No. 60/605,753, filed Aug. 31, 2004.
U.S. Appl. No. 60/658,827, filed Mar. 17, 2005.
Co-Pending U.S. Appl. No. 09/458,014, filed Dec. 10, 1999.
Co-Pending U.S. Appl. No. 11/932,548, filed Oct. 31, 2007.
Co-Pending U.S. Appl. No. 12/421,690, filed Apr. 10, 2009.
Co-Pending U.S. Appl. No. 12/093,515, filed May 13, 2008.
Co-Pending U.S. Appl. No. 12/523,652, filed Jul. 17, 2009.
Co-Pending U.S. Appl. No. 12/523,697, filed Jul. 17, 2009.
Co-Pending U.S. Appl. No. 12/095,611, filed May 30, 2008.
Co-Pending U.S. Appl. No. 12/520,618, filed Jun. 22, 2009.
Co-Pending U.S. Appl. No. 12/520,609, filed Jun. 22, 2009.
Co-Pending U.S. Appl. No. 12/294,979, filed May 13, 2009.
Co-Pending U.S. Appl. No. 12/444,974, filed Apr. 9, 2008.
Co-Pending U.S. Appl. No. 12/514,129, filed May 8, 2009.
Co-Pending U.S. Appl. No. 12/086,454, filed Jun. 12, 2008.
Co-Pending U.S. Appl. No. 12/084,662, filed May 7, 2008.
Co-Pending U.S. Appl. No. 10/895,985, filed Jul. 22, 2004.
Co-Pending U.S. Appl. No. 12/628,735, filed Dec. 1, 2009.
Co-Pending Application PCT/US/096150 filed Oct. 21, 2009.
Co-Pending U.S. Appl. No. 12/514,715, filed May 13, 2009.
Co-Pending U.S. Appl. No. 12/158,524, filed Jun. 20, 2006.
Vandana et al, "Phase II Trial of Sorafenib in Advanced Thyroid Cancer" Journal of Clinical Oncology vol. 26, No. 29 (Oct. 10, 2008).
Sternberg et al, "Conspiracy Theory: RAS and RAF Do Not Act Alone" Cell, vol. 95, 447-450 (Nov. 13, 1998).
Kolch et al, "The Role of RAF Kinases in malignant transformation" Expert reviews in molecular medicine (Apr. 25, 2002.
Kyriakis et al, "Raf-1 activates MAP kinase-kinase" Nature, 358, 6385 Research Library p. 417 (Jul. 30, 1992).
Board et al, "Platelet-derived growth factor receptor (PDGFR): A target for anticancer therapeutics" Drug Resistance Updates 8 (2005) 75-83.
Bollag et al, "Raf pathway inhibitors in oncology" Current Opinion in Investigational Drugs (2003) 4(12): 1436-1441.
Gupta et al, "Sorafenib targets BRAF and VEGFR in metastatic thyroid carcinoma" Journal of Clinical Oncology, 2007 ASCO Annual Meeting Proceedings (Post-Meeting Edition) vol. 25, No. 18S (Jun. 20 Supplement), 2007: 6019.
Mross et al, "Results from an in vitro and a clinical/pharmacological phase I study with the combination irinotecan and sorafenib" European journal of cancer 43, 55-63 (Nov. 13, 2006).
Tong et al, "Pharmacodynamic Monitoring of BAY 43-9006 (Sorafenib) in Phase I clinical trials involving solid tumor and AML/MDS patients, using flow cytometry to monitor activation of the ERK pathway in peripheral blood cells" Cytometry Part B (Clinical Cytometry) 70B: 107-114 (2006).
Kupsch et al, "Results of a Phase I Trial of Sorafenib (BAY 43-9006) in Combination with Oxaliplatin in Patients with Refractory Solid Tumors, Including Colorectal Cancer." Clinical Colorectal Cancer—Cancer Information Group Journal, vol. 5 Issue 3, (Sep. 2005).
Ghassan et al, "Phase II Study of Sorafenib in Patients with Advanced Hepatocellular Carcinoma." Journal of Clinical Oncology, vol. 24 No. 26 (Sep. 10, 2006).
Ratain et al, "Phase II Placebo-Controlled Randomized Discontinuation Trial of Sorafenib in patients with Metastatic Renal Cell Carcinoma" Journal of Clinical Oncology vol. 24 No. 16, (Jun. 1, 2006).
Awada et al, "Phase I safety and pharmacokinetics of BAY 43-9006 administered for 21 days on/7 days off in patients with advanced, refractory solid tumors" British Journal of Cancer 92, 1855-1861 (2005).
Escudier et al, "Sorafenib in Advanced Clear-Cell Renal-Cell Carcinoma" New England Journal of Medicine vol. 356: 125-134 (Jan. 11, 2007).
"Nexavar Receives FDA Fast Track Designation for Skin Cancer" (Jul. 21, 2006) http://www.medicalnewstoday.com/articles/47793.php (last visited on Jun. 16, 2008).
Wilhelm et al, "Sorafenib (Nexavar; BAY 43-9006): discovery and development of the first oral multi-kinase inhibitor that targets Raf and angiogenesis for the treatment of advanced renal cancer" Sorafenib (Nature Reviews Drug Discovery) Review (Apr. 12, 2006).
Bianchi et al, "Phase II multicenter uncontrolled trial of sorafenib (BAY 43-9006) in patients with metastatic breast cancer" Journal of Clinical Oncology (Presented Mar. 21-26, 2006).

(56) References Cited

OTHER PUBLICATIONS

Jain et al, Randomized Discontinuation Trial of Sorafenib (BAY 43-9006) Cancer Biology & Therapy, vol. 5 Issue 10 (2006).
Siu et al, "Phase I Trial of Sorafenib and Gemcitabine in Advanced Solid Tumors with an Expanded Cohort in Advanced Pancreatic Cancer" Clin Cancer Res 12(1) (2006).
Eisen et al, "Sorafenib in advanced melanoma: a Phase II randomized discontinuation trial analysis" British Journal of Cancer 95, 581-586 (2006).
Marshall, "MAP kinase kinase kinase, MAP kinase kinase, and MAP kinase" Curr Opin Genet Dev. 4: 82-9, 1994.
Doanes et al, "VEGF stimulates MAPK through a pathway that is unique for receptor tyrosine kinases" Biochem Biochem Biophys Res Commun. 255: 545-8 1999.
Hardmann et al., "Goodman & Gilman's The Pharmacological Basis of Therapeutics," 9th ed., 1996, pp. 51 and 57-58.
Smyth R M et al, "Anchimeric assistance in the specific acid-catalysed hydration of bensonitriles", J Chem. Soc. Perkin Trans. 2 1993 pp. 2171-2173. XP-001189455.
Chemical Abstracts vol. 117 No. 25 1992 ab. No. 251318p.
Stavchansky S. et al, "Evaluation of the Bioavailability of a solid dispersion of Phenytoin in Polyethylene glycol 6000 and a commercial phenytoin sodium capsule in the dog", Journal of pharmaceutical sciences/733 vol. 73 No. 6, (Jun. 1984).
Franco M. et al, "Dissolution properties and anticonvulsant activity of phenytoin-polyethylene glycol 6000 and polyvinylpyrrolidone K-30 solid dispersions" International journal of pharmaceutics 225 (2001) 63-73 © 2001 Elsevier Sciences B.V.
Craig D et al, "The mechanisms of drug release from solid dispersions in water-soluble polymers" International journal of pharmaceutics 231 (2002) 131-144 © 2002 Elsevier Sciences B.V.
Serajuddin et al, "Solid dispersions of poorly water-soluble drugs: Early promises subsequent problems, and recent breakthroughs" 1058/Journal of pharmaceutical sciences vol. 88, No. 10, (Oct. 1999).
Yan He et al, "Oral formulation of a Novel Antiviral Agent. PG301029, in a mixture of Gelucine 44/14 amd DMA (2:1, wt/wt)" AAPS PharmSciTech 2005; vol. No. 6 (1) Article 1 (http://www.aapspharmscitech.org) (visited on Nov. 20, 2009) College of Pharmacy, The University of Arizona.
Choi Yun-Jung et al, "Imatinib-Resistant cell lines are sensitive to the RAF inhibitor Bay 43-9006" Blood, W.B. Saunders Company, Orlando, FL, US, vol. 100, No. 11, (Dec. 10, 2002).
Guido et al, "International Melanoma Research Congress—Foundation for Melanoma Research. Jun. 21-24, 2003, Philadelphia, PA USA." IDRUGS: The investigational drugs journal Aug. 2003, vol. 6, No. 8, Aug. 2003 (2003-2008), p. 752-754, XP002402150.
Elting, James et al, "Biomarkers associated with clinical outcomes in targets, a Phase III single-agent, placebo-controlled study of sorafenib in advanced renal cell carcinoma" vol. 47, Apr. 2006 (2006-2004), pp. 683-684, XP001245679 & 97th annual meeting of the American-Association-for-cancer-research (AACR); Washington, DC, USA; Apr. 1-5, 2006. ISSN: 0197-016X.
Anat Norden-Zfoni, "Blood-Based Biomarkers of SU11248 Activity and clinical outcome in patients with metastatic Imatinib-Resistant Gastrointestinal Stromal Tumor" Clin Cancer Res 2007;13(9) May 1, 2007 (www.aacrjournals.org).
John Ebos et al, "Multiple circulation proangiogenic factors induced by sunitinib malate are tumor-independent and correlated with anti-tumor efficacy" PNAS vol. 104, No. 43, 17069-17074 (Oct. 23, 2007).
Sandrine Faivre et al, "Molecular basis for sunitinib efficacy and future clinical development" Nature Publishing Group, 734, vol. 6 (Sep. 2007).
Michael Tamm et al, "Hypoxia induced interleukin-6 and inerleukin-8 production is mediated by platelet activation factor and platelet derived growth factor in primary human lung cells" Am. J. Respir. Cell Mol. Biol. vol. 19, pp. 653-661, (1998).
Bhagwat et al, "The angiogenic regulator CD13/APN is a transcriptional target of Ras signaling pathways in endothelial morphogenesis," Blood 1, vol. 101 No. 5 (Mar. 1, 2003).

Rak et al, "Oncogenes as inducers of tumor angiogenesis" Cancer and Metastasis Reviews 14: 263-277, 1995. © 1995 Kluwer Academic Publishers. Printed in the Netherlands.
Rak et al, "Oncogenes and tumor Angiogenesis: Differential Modes of vascular Endothelial growth factor up Regulation in ras-transformed Epithelial cells and Fibrolast" Cancer Research 60, 490-498, Jan. 15, 2000).
Rak et al, "Oncogenes and Angiogenesis: Signaling Three-Dimensional Tumor Growth" Cancer Biology research division, sunnybrook and women's college hospital health sciences center, Toronto Sunnybrook Regional cancer Centre Department of Medical Biophysics, University of Toronto, Toronto, Ontario, Canada. 1087-0024/00/15.00 © The Society for Investigative Dermatology, Inc.
Flaherty et al "Phase I/II trial of Bay 43-9006 carboplatin (c) and paclitaxel (P) demonstrates preliminary antitumor activity in the expansion cohort of patents with metastiatic melanoma." Journal of Clinical Oncology, 2004 ASCO annual meeting proceedings, vol. 22, No. 145 (Jul. 15, 2004) Supplement: 7507.
Guido et al, "Internation melanoma research congress—Foundation fo melanoma research" Idrugs 2003 6(8): 752-754 © Current Drugs ISSN: 1369-7056.
Stokoe et al, "Activation of c-Raf-1 by Ras and Src through different mechanisms: activation in vivo and in vitro." The EMBO Journal, vol. 16 No. 9 pp. 2384-2396 (1997).
Dorwald, "Side Reactions in Organic Synthesis: A Guide to Successful Synthesis Design." Wiley-VCH Verlag GmbH & Co. KGaA (2005).
Siu et al, "Phase I study of oral raf-1 kinase inhibitor BAY 43-9006 with gemcitabine in patients with advanced solid tumors." Proc Am Soc Oncol 22: p. 207, 2003 (abstr 828).
Redman et al, "p38 Kinase Inhibitors of the Treatment of Arthritis and Osteoporosis: Thieny, Furyl, and Pyrrolyl Ureas." Bioorganic & Medicinal Chemistry Letters 11 (2001) 9-12.
Dumas et al, "Discovery of a New Class of p38 Kinases Inhibitors." Bioorganic & Medicinal Chemistry Letters 10 (2000) 2047-2050.
Wojnowski et al, "Endothelial apoptosis in Braf-deficient mice" Nature Genetics vol. 16 (Jul. 1997).
Chialda et al, "Respiratory Research" 2005, 6:36, pp. 1-19.
Kapoun et al, Molecular Pharmacology, abstract, 2006, www.molpharmaspetjournals.org.
Feldmann, "Nature Immunology" 2001, vol. 2, No. 9, pp. 771-773.
National Cancer Institute, "Sorafenib With or Without Paclitaxel and Carboplatin in Treating Patients With Recurrent Ovarian Cancer, Primary Peritoneal Cancer, or Fallopian Tube Cancer", NCT0096200, www.clinicaltrials.gov.
National Cancer Institute, "Placlitaxel, Carboplatin, and Radiation Therapy in Treating Patients Who Are Undergoing Surgery for Stage III Non-Small Cell Lung Cancer", NCT00096226, www.clinicaltrials.gov.
Bayer Corporation, "Trial of BAY 43-9006 with Relapsed or Refractory Advanced Non-Small Cell Lung Carcinoma", NCT0010413, www.clinicaltrials.gov.
National Cancer Institute, "Carboplatin and Paclitaxel With or Without Sorafenib in Treating Patients With Unresectable Stage III or Stage IV Melanoma", NCT0011019, www.clinicaltrials.gov.
National Institutes of Health Clinical Center, "BAY 43-9006 (Sorafenib) to Treat Relapsed Non-Small Cell Lung Cancer", NCT00098254, www.clinicaltrials.gov.
Gressler, "The Importance of Solvates", Polymorphism in the Pharmaceutical Industry, Chapter 8, p. 211, 2006, Wiley-VCH Verlug GmbH & Co., KGaA, Weinhelm.
Monia, "First- and second-generation antisense oligonucleotide inhibitors targeted against human c-raf kinase" Wiley, Chichester (Ciba Foundation Symposium 209) p. 107-123.
Nemunaitis et al, "Phase I Evaluation of ISIS 3521, an Antisense Oligodeoxynucleotide to Protein Kinase C-Alpha, in Patients with Advanced Cancer" Journal of Clinical Oncology, vol. 17, No. 11, pp. 3586-3595 (Nov. 1999).
Holmlund et al, Phase I Trial of C-raf Antisense Oligonucleotide ISIS 5132 (CGP 69846A) by 21-day Continuous Intravenous Infusion (CIV) in patients with advanced cancer (Meeting abstract).

(56) References Cited

OTHER PUBLICATIONS

Cancer Weekly, "Antisense Technology (Clinical Trial) Phase II Trial of Second Antisense Cancer Drug Begins" Cancer Weekly, p. 4 (Dec. 8, 1997).
Rudin et al, "Phase I Trial of ISIS 5132, an Antisense Oligonucleotide Inhibitor of c-raf 1, Administered by 24-hour weekly Infusion to Patients with Advanced Cancer" Clinical Cancer Research vol. 7, 1214-1220 (May 2001).
National Cancer Institute, Clinical Trials (PDQ), "Phase II Randomized Study of ISIS 5132 or ISIS 3521 in Women with Previously Treated Metastatic Breast Cancer" www.cancer.gov website (1998).
National Cancer Institute, Clinical Trials (PDQ), "Phase II Randomized Study of ISIS 5132 or ISIS 3521 for Locally Advanced or Metastatic Colorectal Cancer" www.cancer.gov website (1998).
National Cancer Institute, Clinical Trials (PDQ), "Phase II Randomized Study of ISIS 5132 or ISIS 3521 in Patients with Hormone Refractory Prostate Cancer" www.cancer.gov website (1998).
National Cancer Institute, Clinical Trials (PDQ), "Phase II Randomized Study of ISIS 5132 in Patients with Advanced Pancreatic Cancer" www.cancer.gov website (Aug. 1999).
Salvatore et al, "BRAF Is a Therapeutic Target in Aggressive Thyroid Carcinoma" Clin Cancer Res 1623;12(5) (Mar. 1, 2006).
Keller et al, "The Role of Raf Kinase inhibitor protein (RKIP) in health and disease" Biochemical Pharmacology 68; 1049-1053 (2004).
Robinson et al, "Enhanced Radiosensitization with Gemcitabine in Mismatch Repair-Deficient HCT116 Cells" Cancer Research 63, 6935-6941 (Oct. 15, 2003).
Devlin et al, "Gatt and Discovery: Signigicant changes in US Patent Law" vol. 3, No. 4 (Dec. 1995).
Hanna et al, "Second-Line treatment of non-small cell lung cancer: Big targets, Small progress; Small Targets, Big progress?" Journal of Thoracic Oncology vol. 1, No. 9, (Nov. 2006).
Valentino et al, "Prodrugs as therapeutics" Expert Opinion of Therapeutic Patents 14(3): 277-280 (2004).
Favaro, J. P. et al., "Targeted therapy in renal cell carcinoma" Expert Opin. Investig. Drugs, 2005, vol. 14, No. 10, pp. 1251-1258.
Gollob, J. A. et al., "Sorafenib: scientific rationales for single-agent and combination therapy in clear-cell renal cell carcinoma," Clin Genitourin Cancer, Dec. 2005, vol. 4, No. 3, pp. 167-174.
Hahn, O. et al., "Sorafenib," Current Opinion Oncol, 2006, vol. 18, pp. 615-621.
Lemoine et al., "Overview of ras oncogenes and their clinical potential," Chapter 10, In: Mutant Oncogenes: Targets for Therapy (eds. Lemoine NR & Epenetos A), Chapman & Hall, London. pp. 85-91; 1992.
Naumann, U. et al., "Raf protein serine/threonine kinases" Chapter 7, 1996, pp. 203-236.
Reddy et al., "Sorafenib: recent update on activity as a single agent and in combination with interferon-alpha2 in patients with advanced-stage renal cell carcinoma." Clin Genitourin Cancer, Mar. 2006, vol. 4, No. 4, pp. 246-248.
Song, H. D. et al., "Cross-host evolution of severe acute respiratory syndrome coronavirus in palm civet and human." Proceedings of the National Academy of Science, Feb. 15, 2005, vol. 102, No. 7., pp. 2430-2435.
Storm et al., "raf Oncogenes in Carcinogenesis" Critical Reviews in Oncogenesis, vol. 2, Issue 1, pp. 1-8, 1990.
Tang et al., "Inhaled nitric oxide attenuates pulmonary hypertension and improves lung growth in infant rats after neonatal treatment with a VEGF receptor inhibitor," Am J Physiol Lung Cell Mol Physiol 287: L344-L351, 2004.
Wermuth, C.G. et al., "Designing Prodrugs and Bioprecursors II: Bioprecursor Prodrugs," The Practice of Medicinal Chemistry, 1996, Academic Press Ltd., pp. 697-715.
Yu et al., The role of Mcl-1 downregulation in the proapoptotic activity of the multikinase inhibitor BAY 43-9006, Oncogene, 2005, vol. 24, pp. 6861-6869.
Smith, R. A. et al., "Recent advances in the research and development of RAF kinase inhibitors," Current Topics in Medicinal Chemistry, 2006, vol. 6, No. 11, pp. 1071-1089.
Public redacted Onyx trail brief, Sep. 8, 2011.
Public Redacted Bayer trial brief, Sep. 8, 2011.
Deposition transcript of S. Bhagwat (Expert for Onyx), Mar. 8, 2001.
Redacted Deposition transcript of J. Lyons (Ex Onyx Employee), Mar. 4, 2011.
Deposition transcript of C. Lipinski (Expert for Bayer), Feb. 18, 2011.
Deposition Transcript of T. Lowinger (Ex Bayer employee), Dec. 13, 2010.
Deposition transcript of S. Wilhelm (Applicant/Bayer employee), Aug. 26, 2010.
Deposition transcript of B. Riedl (Applicant/Bayer employee), Nov. 2010.
Deposition transcript of J. Dumas (Applicant/Ex-Bayer employee), Sep. 20, 2010.
Deposition transcript of L. Adnane (Bayer employee), Jun. 24, 2010.
Med Chem. Plans Slide (1998).
Med. Chem. Plans Slides, BAY00015872 at 879, BAY-A00299697 at 703, BAY-A00484291 at 298, BAY-A00484328 at 335, BAY-A004844359 at 366, BAY-A0551200 at 207, BAY-A00484291 at 298, ONYX00316991 at 992 (Sep. 1998).
Redacted Expert report of Bhagwat, Shripad (Onyx), Jan. 10, 2011.
Supplemental Information for Expert report of Bhagwat, (Onyx), Mar. 7, 2011.
Redacted Ecpert report of Lipinski, Christopher (Bayer), Feb. 7, 2011.
Supplemental Information for Expert report of Lipinski (Bayer), Apr. 1, 2011.
Bayer Deposition Exhibit 318, Memo from Riedl to Lyons w/slides attached (Sep. 17, 1998), John Lyons, pp. 121-126, 140-146, and 199-203.
Onyx Deposition Exhibit 163, Memo from Riedl to Lyons w/slides+notes attached (Sep. 17, 1998), C. Lipinski pp. 156-177; Bernd Riedl, pp. 151-179 and 187.
Bayer Deposition Exhibit 59, ROC presentation (Sep. 18, 1998), Scott Wilhelm pp. 59-68, Bernd Riedl, pp. 173-174, Jacques Dumas, pp. 136-159, 168-173, 244-247 and 350-252.
Onyx Deposition Exhibit 59a; Exhibit 59 ROC presentation with notes (Sep. 18, 1998), Timothy Lowinger, pp. 23-29.
Bayer Deposition Exhibits 14, 319 and 341, Agenda JRDC Meeting w/slides attached (Sep. 28, 1998), Bernd Riedl, pp. 175-178; John Lyons, pp. 156-173; Shripad Bhagwat, pp. 146-153; and 193-201.
Bayer Deposition Exhibit 32, Raf Kinase Project (1998); Bernd Riedl, pp. 186-193.
Bayer Deposition Exhibit 34, Research Report No. MRC-00984 (Oct. 11, 1999); Jacques Dumas, pp. 160-164, Shripad Bhagwat, p. 259.
Redacted Bayer Deposition Exhibit 35, Jennifer Burke Notebook records (2002); Jacques Dumas, pp. 225-228.
Redacted Bayer Deposition Exhibit 39, Strategic Project Plan 2nd Generation Raf Kinase Inhibitor report (Nov. 14, 2002); S. Wilhelm pp. 164-224, B. Riedl, pp. 237-245.
Redacted Bayer Deposition Exhibit 63, Strategic Project Plan 2nd Generation Raf Kinase Inhibitor report (Nov. 25, 2002); S. Wilhelm, pp. 224-227, J. Dumas, pp. 239-253, Bernd Riedl, pp. 247-249, Lila Adnane, pp. 84-91.
Redacted Bayer Deposition Exhibit 67, BRC-2002 Goals vs. Achievements Status slides (Feb. 2003); Scott Wilhelm pp. 244-266.
Bayer Deposition Exhibit 66. Second Generation Raf Kinase Inhibitor Meeting slides (Jul. 22, 2003); Scott Wilhelm pp. 227-244.
Redacted Bayer Deposition Exhibit 49, DPI Document, BAY 73-4506 slides, (Sep. 30, 2003); Scott Wilhelm pp. 227-266, B. Riedl, pp. 245-247, J. Dumas, pp. 196-214.
Redacted Bayer Deposition Exhibit 71, BAY 73-4506 GPT slides, (Jul. 12, 2007); Scott Wilhelm pp. 292-294.
Wilhelm Dep. at 234-237, 254-262 (Aug. 26, 2010).
Development Options meeting Slide, BAY-A01164130 at 134, (Mar. 28, 2008).
Redacted DAST Strategic Imperative Slides, BAY-A00131813, (Dec. 7, 2007).

(56) References Cited

OTHER PUBLICATIONS

Redacted Business and Positioning Strategy 2009 slides, BAY00289234, (Apr. 29, 2010).
Redacted DPI Presentation Slides, BAY-A00565179, (Nov. 18, 2003.
Onyx Exhibit-98, US Patent 7,351,834, Apr. 1, 2008, at pp. 8-11 of opinion.
Onyx Exhibit-99, U.S. Appl. No. 60/115,877, field Jan. 13, 1999; at p. 11 of opinion.
Bayer Deposition Exhibit 334, Chemical Structures Slide, at p. 110 of deposition, (Jun. 1998).
Bayer Deposition Exhibit 336, HIR Assay, (Jun. 19, 1998) at pp. 112-114 of deposition.
Med. Chem. Plans Slides, BAY00015872 at 879, BAY-A00299697 at 703, BAY-A00484291 at 298, BAY-A00484328 at 335, BAY-A004844359 at 366, BAY-A00551200 at 207, BAY-A00484291 at 298, ONYX00316991 at 922 (Sep. 1998).
Med. Chem. Plans Slide, ONYX00020538 at 538, 539, (Sep. 1998).
Kinase Profile Slide BAY-A00230103 at 107, BAY 00177850 at 853, BAY00037799 at 818, BAY-A0013813 at 28, (May 19, 2003, Dec. 17, 2007).
Summary of Sorafenib Evaluation InVitro/InVivo, BAY-A00297658 at 669, after (2004).
Table of Raf Kinase Assay Results, BAY-A00564638 at 731, after (Jun. 2003).
Tables of prepared Compounds, including BAY 734506, and assay results, BAY-A00564638, 649, 670, 671, 836, after (Jun. 2003).
Chemical Synthesis BAY 734506 Slide, BAY00044106 at 132, (Jul. 22, 2003)
RAF Kinase Project Slides, BAY0015744-770, 771, 777, (Oct. 1998).
Slide Summary of RKI-2 Status, BAY-A00230119 at 121, (Feb.-Mar. 2003).
Jennifer Burke Notebook Records, BAY00000036 at 036-038, (Dec. 12, 2002).
Jennifer Burke Notebook Records, BAY 00017043 at 077-078, 080, (Dec. 12, 2002).
Med. Chem. Results Slides, BAY0015872 at 876, BAY-A00484291 at 293; BAY-A00551200 at 202, BAY00205344 at 350, ONYX00155950 at 963, ONYX00534085 at 091, (Sep. 18, 1998).
Screening Cascade Slides, BAY00015915 at 926, BAY-A00568497 at 497, BAY-A00572163, BAY-A00908144 at 150, BAY-01006731 at 731, BAY-A00641601 at 628, ONYX00010785 at 807, ONYX00010847 at 850 and ONYX00207530 at 530, (Jun. 10, 1998).
WHO correspondence re Non-proprietary name, BAY-A00608975, (2007).
WHO Letter re Non-proprietary name, BAY00381873, (2008).
WHO Status Letter re Non-proprietary name, BAY00504872, (2008).
WHO Emails re Non-proprietary name, BAY-A00206034, (2008).
Research Report re Variation of Proximal Phenyl Group. BAY00012572 at 582, 610, (Oct. 11, 1999).
Summary page of SAR of RAF Kinase Inhibitor Lead, BAY-A00908144 at 151, (Jan. 25, 1999).
Slide of SAR of Biphenyl Ureas, BAY00015744 at 765, (Oct. 1998).
pp. 4-5 of Lowinger Publication, BAY-A00722597 at 510 and 511, published (2002).
$2^{nd}$ Generation RKI Strategic Project Plan, pp. 21-22, BAY-A00565114 at 135-136, (Nov. 14, 2002).
RKI2 Actions Points e-mail, BAY-A00230173 (Aug. 1, 2003).
Table of Prepared Compounds and Assay Results, BAY-A00564638, after (Jun. 2003).
Redacted Raf Kinase Project, Effects of Substitution on First Ring, BAY00015798 at 810, date created unknown, cited (Jan. 10, 2011).
Raf Kinase Project Slides, BAY0015744, (Nov. 1998).
Redacted—$2^{nd}$ Generation RAF Kinase Slides, BAY00221648, (Sep.-Oct. 2002).
BAY 73-4506 DAST Inhibitor—Present Slides, BAY00179838, (May 7, 2008).
Redacted—CK2 Strategic Project, BAY-A00230119, (Feb.-Mar. 2003).
Unpublished paper, Riedl et al., Discovery of Nexavar, BAY-A00498289, date created unknown, cited (Jan. 10, 2011).
Patani, George A., et al., "Bioisosterism: A Rational Approach in Drug Design," 96 Chem. Rev. 3147 (1996).
Burger, Alfred, Burger's Medicinal Chemistry and Drug Discovery, vol. 1, Principles and Practice (Manfred E. Wolff., $5^{th}$ ed. 1995).
Patrick, Graham L., An Introduction to Medicinal Chemistry (Oxford University Press, 1995).
Hanahan, Douglas & Weinberg, Robert A., The Hallmark of Cancer, 40 Cell 57 (2000).
Smith, Roger A., et al., "Recent Advances in the Research and Development of RAF Kinase Inhibitors," 6 Current Topics in Medicinal Chemistry 1071 (2006).
Smart, Bruce E., "Organofluorine Chemistry: Principles and Commercial Application," 66-67 (Plenum Press 1994).
Chambers, Richard D., Fluorine in Organic Chemistry (CRC Press 2004).
Bayer's Brief in support of Summary Judgment Motion (SJM) (Mar. 21, 2011).
Joint Statement of Facts (Apr. 13, 2011).
Onyx's Response to Bayer's SJM (Apr. 12, 2011).
Onyx's Objections to Bayer's Evidence in Support of SJM (Apr. 19, 2011).
Onyx's Second Response to SJM (Apr. 13, 2011).
McCormick Declaration in Support of Onyx's Opposition to SJM (Apr. 15, 2011).
Swanson Supplemental Declaration in Support of SJM (Mar. 15, 2011).
Swanson Supplemental Declaration in Support of SJM (Mar. 30, 2011).
Schenker Declaration in Support of Onyx's Opposition to SJM (Mar. 30, 2011).
Bhagwat Declaration in Support of Onyx's Opposition to SJM (Mar. 31, 2011).
Memo and Order re Summary Judgment (May 5, 2011).
Exhibit 13 of Swanson declaration in support of Summary Judgment, Deposition testimony of W. Scott, pp. 1, 18, 19, 24, 67, 68, 110 NS 111, (May 6, 2010).
Exhibit 16 of Swanson declaration in support of Summary Judgment, Deposition testimony of B. Riedl, pp. 1, 18-22 and 227, (Nov. 2010).
Exhibit 20 of Swanson declaration in support of Summary Judgment, Notebook page (Reina Natero), BAY00039916, (1998).
Exhibit 22 of Swanson declaration in support of Summary Judgment, Report RAF Kinase Inhibition, BAY 43-9006 (Jan. 25, 1999).
Exhibit 23 of Swanson declaration in support of Summary Judgment, Deposition testimony of S. Wilhelm, pp. 1, 76 and 77, (Aug. 26, 2010).
Exhibit 25 of Swanson declaration in support of Summary Judgement, Notebook pp. (2) (Jennifer Burke), BAY00017080, (2002).
Exhibit 26 of Swanson declaration in support of Summary Judgment, Notebook page (Gloria Hofilena), BAY0018315, (2002).
Exhibit 27 of Swanson declaration in support of Summary Judgment, Deposition testimony of L. Adnane, pp. 1, 9-11, 73-76, (Jun. 24, 2010).
Exhibit 52 of Swanson declaration in support of Summary Judgment, Deposition testimony of J. Dumas, pp. 1, 199-200, (Sep. 20, 2010).
Exhibit 106 of Schenker declaration in support of opposition, Deposition testimony of J. Dumas, pp. 1, 3, 199, 200, 221, 237 and 238, (Sep. 20, 2010).
Exhibit 111 of Schenker declaration in support of opposition, Deposition testimony of C. Lipinski pp. 1, 5, 214-216 (Feb. 18, 2011).
Exhibit 112 of Schenker declaration in support of opposition, Deposition testimony of T. Lowinger, pp. 1, 3, 4, 26, 27, 32, 53, 71-73 and 79, (Dec. 13, 2010).
Exhibit 113 of Schenker declaration in support of opposition, Deposition testimony of J. Lyons, pp. 1, 5, 142-144, 150, 151, 200, 201 and 205 (Mar. 4, 2011).
Exhibit 117 of Schenker declaration in support of opposition, Deposition testimony of B. Riedl, pp. 1, 5, 13, 14, 18, 21-24, 26, 27, 31, 32, 57-63, 91, 95, 103, 118-120 and 204, (Nov. 2010).

(56) References Cited

OTHER PUBLICATIONS

Corrected Exhibit 121 of Schenker declaration in support of opposition, Deposition testimony of W. Scott, pp. 1, 5, 10, 11, 43, 44, 46, 47 and 112-114, (May 6, 2010).
Exhibit 122 of Schenker declaration in support of opposition, Deposition testimony of S. Wilhelm, pp. 1, 6, 54 and 66-68 (Aug. 26, 2010).
Exhibit 123 of Schenker declaration in support of opposition, Deposition testimony of L. Adnane, pp. 1, 5, 11 and 69-73 (Jun. 24, 2010).
Exhibit 127 of Schenker declaration in support of opposition, Notebook records of Jennifer Burke, pp. 56, 57, 58, 59, 62 and 63. (Dec. 12, 2002).
Exhibit 143 of Schenker declaration in support of opposition, Web page ClinicalTrials.gov, Regorafenib+FolFiri verses Placebo+FolFiri-Colorectal Cancer, 7 pages, (Feb. 16, 2011).
(Cumulative to L17) Exhibit 150 of Schenker declaration in support of opposition, Memo from Riedl to J. Lyons with Slides, (Sep. 17, 1998).
Exhibit 152 of Schenker declaration in support of opposition, Memo to Bollag with Slides, (Oct. 15, 1998).
Exhibit 154 of Schenker declaration in support of opposition, Agenda JRDC meeting with Slides, (Sep. 28, 1998).
Exhibit 155 of Schenker declaration in support of opposition, E-mail with HIR data attached, (Jun. 24, 1998).
Exhibit 156 of Schenker declaration in support of opposition, Minutes for Meeting between Bayer/Miles and Onyx, (Sep. 24, 1993).
(Cumulative to L17 and SJ11-K) Exhibit 157 of Schenker declaration in support of opposition, Memo from B. Riedl to L. Lyons with Slides, (Sep. 17, 1998).
Exhibit 158 of Schenker declaration in support of opposition, Redacted Slide of Analogs of BAY 43-9006, (Sep. 17, 1998).
Exhibit 166 of Schenker declaration in support of opposition, Article, Defauw, et al., J. Med. Chem., (1996), 39, 5215-5227.
Exhibit 168 of Schenker declaration in support of opposition, JRDC Meeting Minutes, (Jun. 5, 1995).
Exhibit 169 of Schenker declaration in support of opposition, JRDC Meeting Minutes, (Mar. 29, 1996).
Exhibit 170 of Schenker declaration in support of opposition, RAF Kinase Project Slides, (Apr. 8, 1997).
Exhibit 171 of Schenker declaration in support of opposition, Memo re Onyx visit, (Apr. 30, 1993).
Exhibit 172 of Schenker declaration in support of opposition, Report No. MRC-00984, Research Report, (Oct. 11, 1999).
Exhibit 173 of Schenker declaration in support of opposition, Article by Lowinger et al., Design and Discovery of Small Molecules Targeting RAF-1, Current Pharmaceutical Design, 2002, 8, 99-110.
Exhibit 175 of Schenker declaration in support of opposition, Agenda JRDC meeting with Slides, (Sep. 23, 1998).
Exhibit 187 of Schenker declaration in support of opposition, Fax to G. Giotta re Collaboration, (Sep. 6, 2001).
Exhibit 186.1 of Schenker declaration in support of opposition, E-mail re DAST RCC ASCO Abstract (Dec. 19, 2003).
Corrected Exhibit 186.2 of Schenker declaration in support of opposition, E-mail re DAST RCC ASCO Abstract (Dec. 19, 2003).
Exhibit 188 of Schenker declaration in support of opposition, E-mail re G. Giotta re patent applications, (Jun. 22, 2003).
Exhibit A of Bhagwat declaration in support of opposition, Compound list, "Key Compounds in the Discovery of DAST," date created unknown, date cited: (Mar. 31, 2022).
Exhibit B of Bhagwat declaration in support of opposition, Table of Assay Results for Bayer Compounds, BAY 00207465, (Apr. 26, 2010).
Exhibit C of Bhagwat declaration in support of opposition, "Highlights" (Curriculum Vitae) of Shripad Bhagwat (Jan. 10, 2011).
Exhibit CC of Bhagwat declaration in support of opposition, Summary of HIR assay, (Jun. 10, 1998).
Exhibit EE of Bhagwat declaration in support of opposition, RAF Kinase Project Slides, (Oct. 1998).
Exhibit F of Bhagwat declaration in support of opposition, JRDC Meeting Minutes, (Jun. 5, 1995).
Exhibit FF of Bhagwat declaration in support of opposition, Agenda JRDC Meeting, (Jun. 10, 1998).
(Cumulative to SJ11-X) Exhibit G of Bhagwat declaration in support of opposition, Article by Lowinger, et al., Design and Discovery of Small Molecules Targeting RAF-1, Current Pharmaceutical Design, 2002, 8, 99-110.
Exhibit H of Bhagwat declaration in support of opposition, Slides, "Lead Structure Check List," BAY0035386 date created unknown (Mar. 31, 2011).
Exhibit I of Bhagwat declaration in support of opposition, RAF Kinase Project Slides, (Oct. 1998).
Exhibit J of Bhagwat declaration in support of opposition, Report No. MRC-00984 Research Report Slides, (Oct. 11, 1999).
(Cumulative to L35) Exhibit K of Bhagwat declaration in support of opposition, US Patent 7351834, (Apr. 1, 2008).
(Cumulative to L36) Exhibit L of Bhagwat declaration in support of opposition, Onyx Exhibit-99, U.S. Appl. No. 60/115,877, filed Jan. 13, 1999.
Exhibit M of Bhagwat declaration in support of opposition, Article, Discovery and Development of Sorafenib: A Multikinase for Treating Cancer, Nature Reviews, Drug Discovery, vol. 5, (Oct. 2006), 835-844.
(Cumulative to L60A-E) Exhibit N of Bhagwat declaration in support of opposition, List of Compounds Synthesized, BAY-A00564638, after (Jun. 2003).
(Cumulative to L16, SJ11-K and SJ11-P) Exhibit O of Bhagwat declaration in support of opposition, Memo from B. Riedl to J. Lyons with Slides, (Sep. 17, 1998).
(Cumulative to SJ8-D) Exhibit P of Bhagwat declaration in support of opposition, Report "RAF Kinase Inhibitor BAY 43-9006", (Jan. 25, 1999).
Exhibit Q of Bhagwat declaration in support of opposition, Tables of Assay Results/solubility for Bayer compounds, BAY A00564731.
(Cumulative to L21) Exhibit R of Bhagwat declaration in support of opposition, Slide, "RAF Kinase Project," (Sep. 1998).
(Cumulative to L17) Exhibit S of Bhagwat declaration in support of opposition, Memo to J. Lyons with Slides, Onyx Deposition Exhibit 163, (Sep. 17, 1998).
(Cumulative to SJ11-L) Exhibit U of Bhagwat declaration in support of opposition, Memo to G. Bollag with Slides, (Oct. 15, 1998).
(Cumulative to L20 and SJ11-M) Exhibit W of Bhagwat declaration in support of opposition, Agenda JRDC Meeting with Slides, (Sep. 28, 1998).
Exhibit X of Bhagwat declaration in support of opposition, Text, Burgers Medicinal Chemsitry and Drug Discovery, Chapter 19, (1995).
(Cumulative to A17) Exhibit Y of Bhagwat declaration in support of opposition, Article, Bioisosterism: A Rational Approach in Drug Design, 96, Chem Rev 3147 (1996).
Trial testimony of John Lyons, pp. 619-687, (Oct. 5, 2011).
Trial testimony of John Lyons and Shripad Bhagwat, 688-894 (Oct. 6, 2011).
(Cumulative with L17, SJ11-K, SJ11-P, SJ15-s) Trial Exhibit 3, Bayer Deposition Exhibit 318, Memo from B. Riedl to J. Lyons with Slides, (Sep. 17, 1998).
(Cumulative with L22, SJ11-W and SJ15-J) Trial Exhibit 5, Bayer Deposition Exhibit 34, Report No. MRC-00984, Research Report, Oct. 11, 1999).
(Cumulative with SJ8-D and SJ15-P) Trial Exhibit 6, Deposition Exhibit 60, Report RAF Kinase Inhibitor BAY 43-9006, (Jan. 25, 1999).
Redacted Trial Exhibit 61, Bayer Deposition Exhibit 273, Report, "Cancer Exploratory Research, Inhibition of the RAS Pathway, First Quarter 1995," (May 26, 1995).
Trial Exhibit 65, Bayer Deposition Exhibit 95, JRDC Agenda, (Dec. 4, 1995).
(Cumulative with SJ11-T) Trial Exhibit 66, JRDC Minutes (Mar. 29, 1996).
(Cumulative with SJ11-U) Trial Exhibit 71, RAF Kinase Project Slides, (Apr. 8, 1997).
(Cumulative with SJ15-F) Trial Exhibit 84, JRDC Agenda Minutes, Slides, (Jun. 10, 1998).
Trial Exhibit 90, RAF Kinase Project Slides, (Sep. 1998).

(56) References Cited

OTHER PUBLICATIONS

Redacted Trial Exhibit 100, JRDC Meeting Minutes, (Sep. 28, 1998).
Redacted Trial Exhibit 104, RAF Kinase Project Slides, Rheuma Strategic TRAC Meeting, (Oct. 1998).
(Cumulative to SJ15-U and SJ11-L) Trial Exhibit 106, Onyx Deposition Exhibit 169 Memo to Bollag with Slides, (Oct. 15, 1998).
(Cumulative to L24) Redacted Trial Exhibit 129, Deposition Exhibit 39, Strategic Project Plan $2^{nd}$ Generation RAF Kinase Inhibitor (Nov. 14, 2002).
(Cumulative to L23) Redacted Trial Exhibit 130, Deposition Exhibit 35, Laboratory Notebook Jennifer Burke, pp. 1-100, (Nov. 15, 2002).
Trial Exhibit 131, Deposition Exhibit 63, Redacted Strategic Project Plan $2^{nd}$ Generation RAF Kinase Inhibitor, (Nov. 25, 2002).
(Cumulative to L46 and L47) Trial Exhibit 132, Deposition Exhibit 35A, Jennifer Burke Notebook Records, pp. 56-59, 62 and 63. (Dec. 2, 2002).
Trial Exhibit 211, RAF Kinase Project Slides. (Jul. 1998).
(Cumulative to L50) Trial Exhibit 277, Correspondence with WHO re: International Non-proprietary Name (INN), (Mar. 7, 2008).
Trial Exhibit 300, Correspondence with WHO re: International Non-proprietary Name (INN), (Apr. 11, 2008).
(Cumulative to L34) Redacted Trial Exhibit 551, DPI Presentation, (Nov. 18, 2003).
Trial Exhibit 795, "Highlights" Curriculum Vitae of Shripad Bhagwat, Expert for Onyx, (Jan. 10, 2011).
Redacted Trial Exhibit 1009, JRDC Meeting Minutes, (Mar. 11, 1998).
(Cumulative to SJ11-M) Trial Exhibit 1014, JRDC Meeting Agenda with Slides, (Sep. 28, 1998).
Trial Exhibit 1108, Onyx Web Page (2011).
Redacted Trial Exhibit 1237, Bayer Deposition Exhibit 237, CRC-JDC Meeting Slide, (Oct. 21, 2010).
Trial Exhibit 1375, Meeting Minutes FDA-Bayer/Onyx re: Sorafenib, (Sep. 10, 2010).
(Cumulative to L23 and L137) Trial Exhibit 1435B, Lab Notebook of Jennifer Burke, pp. 1-100 (Microfiche), (Nov. 15, 2002-Jan. 16, 2003).
Trial Exhibit 1446, Lab Notebook of Gloria Hofilena, pp. 1-100, (Oct. 2002-Feb. 2003).
Trial Exhibit 1916, Article, 4-Amino-5-Aryl-6-arylethynyl pyrimidine Structure Activity Relationship of Non-Nucleoside kinase Inhibitors, Matulenko, et al., Biorganic & Med. Chem., 15 (2007), 1586-1605.
Trial Exhibit 140, Onyx Press Release, (Jun. 11, 2003).
Redacted Trial Exhibit 1, Collaboration agreement, Section 1.9, (Apr. 24, 1994).
Redacted Trial Exhibit 2, Amendment to proposed Collaboration agreement, Exhibit D (Apr. 24, 1994).
L156 Trial Exhibit 948, Slide Presentation, Key Message Platform for Bay 43-9006, date created unknown, prior to (Nov. 7, 2003).
L157 Trial Exhibit 950, Slide presentation, Targeting Cancer with Therapeutic Innovation at Bayer Schering Pharma, date created unknown (Oct. 5, 2011).
Co-pending U.S. Appl. No. 09/776,936, filed Dec. 22, 1998.
Co-pending U.S. Appl. No. 13/401,272, filed Feb. 21, 2012.
Abandoned U.S. Appl. No. 09/458,014, filed Dec. 10, 1999.
Abandoned U.S. Appl. No. 12/421,690, filed Apr. 10, 2009.
Abandoned U.S. Appl. No. 10/659,639, filed Sep. 11, 2003.
Abandoned U.S. Appl. No. 12/294,979, filed Sep. 29, 2008.
Abandoned U.S. Appl. No. 12/091,889, filed Aug. 1, 2008.
Expired U.S. Appl. No. 60/536,734, filed Jan. 16, 2004.
Expired U.S. Appl. No. 60/115,877, filed Jan. 13, 1999.
U.S. Appl. No. 09/083,399; Claims, May 22, 1998.
U.S. Appl. No. 12/619,878; Claims and Office Action, Nov. 17, 2009.
U.S. Appl. No. 12/619,913; Claims and Office Action, Nov. 17, 2009.
U.S. Appl. No. 09/083,396; Claims, May 22, 1996.
U.S. Appl. No. 09/776,936; Claims and Office Action, Dec. 22, 1996.
U.S. Appl. No. 12/145,679; Claims and Office Action, Jun. 25, 2008.
U.S. Appl. No. 11/768,112; Claims and Office Action, Jun. 25, 2007.
U.S. Appl. No. 13/349,199; Claims, Jan. 12, 2012.
Application No. 13/3401272; Claims, Feb. 21, 2012.
U.S. Appl. No. 09/472,232; Claims and Office Action, Dec. 27, 1999.
U.S. Appl. No. 11/758,533; Claims and Office Action, Jun. 26, 2007.
U.S. Appl. No. 10/060,396; Claims and Office Action, Feb. 1, 2002.
U.S. Appl. No. 11/932,397; Claims and Office Action, Oct. 31, 2007.
U.S. Appl. No. 09/458,014; Claims and Office Action, Dec. 10, 1999.
U.S. Appl. No. 11/932,548; Claims and Office Action, Oct. 31, 2007.
U.S. Appl. No. 12/181,032; Claims and Office Action, Jul. 28, 2008.
U.S. Appl. No. 11/158,048; Claims and Office Action, Jun. 22, 2005.
U.S. Appl. No. 11/932,269; Claims and Office Action, Oct. 31, 2007.
U.S. Appl. No. 12/421,690; Claims, Apr. 10, 2009.
U.S. Appl. No. 09/889,227; Claims and Office Action, Jul. 13, 2001.
U.S. Appl. No. 11/956,111; Claims and Office Action, Dec. 13, 2007.
U.S. Appl. No. 09/948,915; Claims and Office Action, Sep. 10, 2011.
U.S. Appl. No. 11/845,595; Claims and Office Action, Aug. 27, 2007.
U.S. Appl. No. 13/368,812; Claims, Feb. 8, 2012.
U.S. Appl. No. 09/777,920; Claims and Office Action, Feb. 7, 2001.
U.S. Appl. No. 10/071,248; Claims and Office Action, Feb. 11, 2001.
U.S. Appl. No. 11/845,597; Claims and Office Action, Aug. 27, 2007.
U.S. Appl. No. 12/249,386; Claims and Office Action, Oct. 10, 2008.
U.S. Appl. No. 10/361,858; Claims and Office Action, Feb. 11, 2003.
U.S. Appl. No. 09/993,647; Claims and Office Action, Nov. 27, 2001.
U.S. Appl. No. 10/042,203; Claims and Office Action, Jan. 11, 2002.
U.S. Appl. No. 11/768,104; Claims and Office Action, Jun. 25, 2007.
U.S. Appl. No. 13/208,010; Claims, Aug. 11, 2011.
U.S. Appl. No. 11/480,360; Claims and Office Action, Jul. 5, 2006.
U.S. Appl. No. 13/189,945; Claims, Jul. 25, 2011.
U.S. Appl. No. 10/361,859; Claims and Office Action, Feb. 11, 2003.
U.S. Appl. No. 11/775,457; Claims and Office Action, Jul. 10, 2007.
U.S. Appl. No. 12/692,845; Claims and Office Action, Jul. 25, 2010.
U.S. Appl. No. 10/788,405; Claims and Office Action, Mar. 1, 2004.
U.S. Appl. No. 10/789,446; Claims and Office Action, Mar. 1, 2004.
U.S. Appl. No. 12/628,735; Claims, Dec. 1, 2009.
U.S. Appl. No. 10/788,426; Claims and Office Action, Mar. 1, 2004.
U.S. Appl. No. 10/659,639; Claims and Office Action, Sep. 11, 2003.
U.S. Appl. No. 10/571,100; Claims and Office Action, Jul. 28, 2006.
U.S. Appl. No. 10/848,567; Claims and Office Action, May 19, 2004.
U.S. Appl. No. 10/788,029; Claims and Office Action, Feb. 27, 2004.
U.S. Appl. No. 11/212,109; Claims and Office Action, Aug. 26, 2005.
U.S. Appl. No. 11/212,907; Claims and Office Action, Aug. 29, 2005.
U.S. Appl. No. 13/303,565; Claims, Nov. 23, 2011.
U.S. Appl. No. 12/092,024; Claims and Office Action, Oct. 17, 2008.
U.S. Appl. No. 12/093,515; Claims and Office Action, May 13, 2008.
U.S. Appl. No. 11/754,082; Claims and Office Action, May 25, 2007.
U.S. Appl. No. 12/091,983; Claims and Office Action, Nov. 13, 2008.
U.S. Appl. No. 11/589,295; Claims and Office Action, Oct. 30, 2006.
U.S. Appl. No. 12/093,719; Claims, May 15, 2008.
U.S. Appl. No. 11/598,824; Claims and Office Action, Nov. 14, 2006.
U.S. Appl. No. 12/523,652; Claims and Office Action, Jul. 17, 2009.
U.S. Appl. No. 12/523,667; Claims and Office Action, Jul. 17, 2009.
U.S. Appl. No. 10/575,027; Claims and Office Action, Jul. 30, 2007.
U.S. Appl. No. 12/090,408; Claims and Office Action, Jul. 14, 2008.
U.S. Appl. No. 11/579,093; Claims and Office Action, Jan. 15, 2008.
U.S. Appl. No. 12/941,841; Claims and Office Action, Nov. 8, 2010.
U.S. Appl. No. 12/095,611; Claims, May 30, 2008.
U.S. Appl. No. 12/520,618; Claims, Jun. 22, 2009.
U.S. Appl. No. 12/520,609; Claims and Office Action, Jun. 22, 2009.
U.S. Appl. No. 12/294,979; Claims, Sep. 29, 2009.
U.S. Appl. No. 12/514,715; Claims and Office Action, May 13, 2009.
U.S. Appl. No. 12/444,974; Claims and Office Action, Apr. 9, 2009.
U.S. Appl. No. 12/514,129; Claims and Office Action, May 8, 2009.
U.S. Appl. No. 11/920,952; Claims and Office Action, Apr. 22, 2009.
U.S. Appl. No. 12/086,454; Claims and Office Action, Jun. 12, 2008.
U.S. Appl. No. 12/084,662; Claims and Office Action, May 7, 2008.
U.S. Appl. No. 11/920,956; Claims and Office Action, Feb. 17, 2009.
U.S. Appl. No. 11/932,620; Claims and Office Action, Oct. 31, 2007.
U.S. Appl. No. 11/885,930; Claims and Office Action, Jun. 9, 2008.
U.S. Appl. No. 11/664,332; Claims and Office Action, May 21, 2008.
U.S. Appl. No. 12/084,659; Claims and Office Action, Feb. 6, 2009.
U.S. Appl. No. 11/664,363; Claims and Office Action, Jun. 20, 2008.
U.S. Appl. No. 12/097,350; Claims and Office Action, Nov. 3, 2008.
U.S. Appl. No. 13/044,124; Claims and Office Action, Mar. 9, 2011.
U.S. Appl. No. 13/236,865; Claims, Sep. 20, 2011.

(56) References Cited

OTHER PUBLICATIONS

U.S. Appl. No. 12/158,524; Claims and Office Action, Jun. 20, 2006.
Application No. PCT/WO09/061506; Claims, Oct. 21, 2009.
U.S. Appl. No. 12/091,889; Claims and Office Action, Aug. 1, 2008.
Application No. PCT/US11/037166; Claims May 19, 2011.
U.S. Appl. No. 12/888,887; Claims and Office Action, Sep. 23, 2010.
U.S. Appl. No. 13/125,212; Claims, Jul. 12, 2011.
U.S. Appl. No. 13/001,193; Claims, Dec. 23, 2010.
Application No. PCT/US11/044506; Claims, Jul. 19, 2011.
U.S. Appl. No. 60/536,734; Claims, Jan. 16, 2004.
U.S. Appl. No. 60/115,877; full text, Jan. 13, 1999.
Alfaro-Lopez, Josue et al., "Discovery of a Novel Series of Potent and Selective Substrate-Based Inhibitors of P60c-src Protein Kinase: Conformational and Topographical Constraints in Peptide Design." 41 J. Med. Chem. 2252 (1998).
Blair, Joseph B., et al., "Effect of Ring Fluorination on the Pharmacology of Hallucinogenic Tryptamines," 43, J. Med. Chem. 4701 (2000), -pub Web Oct. 19, 2000.
Bohm, Hans-Joachim, et al., "Fluorine in Medical Chemistry," 5 ChemBioChem 637 (2004).
Boschelli, Diane H., et al., "Synthesis and Tyrosine Kinase Inhibitory Activity of a Series of 2-Amino-8H-pyrido[2,3-d]pyrimidines: Identification of Potent, Selective Platelet-Derived Growth Factor Receptor Tyrocine Kinase Inhibitors," 41 J. Med. Chem. 4365 (1998).
Burger, Alfred, "The Conceptual Background and Development of Medicinal Chemistry," Burger's Medical Chemistry and Drug Discovery 3: Principles and Practice, Manfred E. Wolff Ed., John Wiley & Sons, 5$^{th}$ Ed. 1995.
Cannon, Joseph, "Analog Design," Burger's Medical Chemistry and Drug Discovery, 783, Manfred E. Wolff Ed., John Wiley & Sons, 5$^{th}$ Ed. 1995.
Dow, Robert L. et al., "Identification of Tricyclic Analogs Related to Ellagic Acid as Potent/Selective Tyrosine Protein Kinase Inhibitors," 37 J. Med. Chem. 2224 (1994).
Doweyko, Arthur, M., "3D-QSAR Illusions," 18 J. Comp. Mol. Des. 567 (2004).
Duran I., et al., "Phase I Targeted Combination Trial of Sorafenib and Erlotinib in Patients with Advanced Solid Tumors," 13 Clinical Cancer Research 4849 (2007).
Dumas, J., "Growth Factor Receptor Kinase Inhibitors Recent Progress and Clinical Impact," 4 Current Opinion in Drug Discovery & Development 378 (2001).
Dumas, J., "Protein Kinase Inhibitors: Emerging Pharmacophores 1997-2000," 11 Expert Opinion on Theapeutic Patients 405 (2001).
Dumas J., Recent Developments in the Discovery of Protein Kinase Inhibitors From the Urea Class. 7 Current Opinion in Drug Discovery & Development 600 (2004).
Goldman, Peter, "The Carbon-Fluorine Bond Compounds of Biological Interest Studies with Fluorinated Molecules Can be Helpful in Understanding Biological Phenomena," 164 Science 3884 (1969).
Guidelines for Authors, J. Med. Chem. (Rev'd Jan. 2011).
Hanahan, Douglas & Weinberg, Robert A., "The Hallmarks of Cancer," 40 Cell 57 (2009).
Hansch, Corwin & Unger, Stefan, "Strategy in Drug Design. Cluster Analysis as an Aid in the Selection of Substituents," 16 J. Med. Chem. 1217 (1973).
Hodgetts, Kevin, et al., "The Role of Fluroine in the Discovery & Optimization of CNS Agents: Modulation of Drug-Like Properties," 45 Ann. Reports in Med. Chem. 429 (2010).
Isanbor, C., "Fluorine in Med. Chem: A Review of Anti-Cancer Agents," 127 J. of Fluorine Chem. 303 (2006).
Johnson, Stephen R., The Trouble with QSAR (or How I Learned To Stop Worrying and Embrace Fallacy), 48 J. Chem. Mod. 25 (2008).
Khire, U.R., et al., "Omega-carboxypyridyl Substituted Ureas as Raf Kinase Inhibitors: SAR to the Amide substituent," 14 Bioorganic & Medicinal Chemistry Letters 783 (2004).
Kirk, Kenneth, et al., "Synthesis and Biological Properties of 2-, 5-, and 6-Fluoronorepinephrines," 22 J. Med. Chem. 1493 (1979).
Lowinger, Tim, et al., "Design and Discovery of Small Molecules Targeting Raf-1 Kinase," 8 Curr. Pharm. Design 2269 (2002).

Maggiora, Gerald, on Outliers and Activity Cliffs, Why QSAR often Disappoints, 46 J. Chem. Int. Model (2006).
McLay, Iain, M., et al., "The Discovery of RPR 200765A, a p38 MAP Kinase Inhibitor displaying a Good Oral Anti-Arthritic Efficacy," 9 Bioorganic & Med. Chem. 537 (2001).
Muller, Klaus, et al., "Fluorine in Pharmaceuticals; Looking Beyond Intuition," 317 Science 1881 (2007).
Nair, Shirkumar, A., et al., "Identification of Efficient Pentapeptide Substrates for the Tyrosine Kinase pp60c-src," 38 J. Med. Chem. 4276 (1995).
O'Hagan, D., "Some Influences of Fluorine in Bioorganic Chemistry," 645 Chem. Commun. (1997).
Patani, George, A., et al., "Biosiosterism: A Rational Approach in Drug Design," 96 Chem. Rev. 3147 (1996).
Patel, Yogenra, "Assessment of Additive/Nonadditive Effects in Structure Activity Relationships: Implications for Iterative Drug Designs," 51 J. Med. Chem. 7552 (2008).
Patrick, Graham, L., "An Introduction to Medicinal Chemistry," Oxford Univ. Press, 1995, pp. xi-xxi.
Pleiss, U., et al., Synthesis of [2H3, 15N], [14C] Nexavar and its Labeled Metabolites, 49 Journal of Labelled Compounds and Radiopharmaceuticals 603 (2006).
Sisay, Mihiret, et al., "Structural Interpretation of Activity Cliffs Revealed by Systematic Analysis of Structure-Activity Relationships in Analog Series," 49 J. Chem. Inf. Model. 2179 (2009).
Smart, Bruce, E., "Characteristics of C-F Systems," Organofluorine Chemistry 57 (2004), Chapter 3.
Smith, R., et al., "Discovery of Heterocyclic Ureas as a New Class of Raf Kinase Inhibitors: Identification of a Second Generation Lead by a Combinatorial Chemistry Approach," 11 Bioorganic & Med. Chem. Letters 2775 (2001).
Stahl, Martin & Bajorath, Jurgen, "Computational Medicinal Chemistry," 54 J. Med. Chem. 1 (2011).
Swain, C. Gardner & Lupton, Jr., Elmer C., "Field and Resonance Components of Substituent Effects," 90 J. Am. Chem. Soc. 4328 (1968).
Thomas, Gareth, "Medicinal Chemistry An Introduction," 2 Ed., Wiley & Sons. 2007 pp. x-xiii.
Thornber, C.W., "Isosterism and Molecule Modification in Drug Design," 8 Chem. Soc. Rev. 563 (1979).
Triggle, David, J., "The Chemist as Astronaut: Searching for Biologically Useful Space in the Chemical Universe," 78 Biochem. Pharm 217 (2009).
Wan, P.T., "Mechanism of Activation of the Raf-Erk Signaling Pathway by Oncogenic Mutations of B-Raf," 116 Cell 855 (2004).
Welch, John, "The Effects of Selective Fluorination on Reactivity in Organic and Bioorganic Chemistry," Selective Fluorination in Organic and Bioorganic Chemistry 1 (Welch Ed., 1991).
Wermuth, Camille Georges, "The Practice of Medicinal Chemistry," 432 (3$^{rd}$ Ed. 2008), pp. xiii, 431-433 and 448-452.
Williams, Michael, "Productivity Shortfalls in Drug Discovery: Contributions from the Preclinical Sciences," 336 J. Pharma. Exp. Therapeutics 3 (2011).
University of California School of Pharmacy: http://pharmacy.ucsf.edu/flossary/d/—2010-2011.
http://www.fiercebiotech.com/story/fda-approvals-2010/2011-01-11.
EP 0161019 B1—Published Nov. 13, 1985.
Biophysical Chemistry 73 (1998) 7-11.
J. Phys. Chem. 1996, 100, 6524-6530.
Meanwell, Nicolas, A., "Synopsis of Some Recent Tactical Applicaion of Bioisosteres in Drug Design," J. Med. Chem. Articles ASAP (Publication Date [Web]: Mar. 17, 2011 [Perspective]).
Szasz, Gyorgy, et al., Pharmaceutical Chemistry of Antihypertensive Agents, vol. 1—1991 by CRC Press, Inc.
Onyx Pharmaceuticals, Inc.'s First Set of Interrogatories, dated Aug. 10, 2009.
Bayer Corporation, Bayer Healthcare LLC, Bayer AG, and Bayer Schering Pharma AG's Response to Onyx Pharmaceuticals, Inc.'s First Set of Interrogatories and Exhibits AD, dated Sep. 14, 2009.
Bayer Corporation, Bayer Healthcare LLC, Bayer AG, and Bayer Schering Pharma AG's Supplemental Responses to Onyx Pharmaceutical Inc.'s First Set of Interrogatories—Apr. 23, 2010.

(56) References Cited

OTHER PUBLICATIONS

Bayer Corporation, Bayer Healthcare LLC., Bayer AG, and Bayer Schering Pharma AG's Responses to Onyx Pharmaceuticals Inc.'s Second Set of Interrogatories—Apr. 12, 2010.
3-Fluoro-4-nitro or Aminophenol STN Search Transcript.pdf—performed Jan. 7, 2011.
Bayer AG, Annual Report 2005.
Bayer AG, Annual Report 2007.
Dumas, Jacques, "Protein Kinase Inhibitors from the Urea Class," Current Opinion in Drug Discovery and Development 718 (2002).
STN International Search (Performed Jan. 7, 2011).
Smart, Bruce, E., "Organofluorine Chemistry: Principles and Commercial Application," 57-88 (Plenum Press 1994).
Chambers, Richard D., "Fluorine in Organic Chemistry," CRC Press 2004.
Bioorganic and Medicinal Chemistry of Fluorine, Chapter 8—Copyright 2008.
Science 2007, 37 1881-1886.
Current Topics in Med. Chem. 2002, 2(9) 1021-35.
J. Med. Chem. 2002 45(2), 1300-12.
Bioorg. Med. Chem. Letters 2001 11, 1911-14.
J. Med. Chem. 1999 42, 5369-89.
J. Med. Chem. 1998 41, 4607-14.
J. Med. Chem. 1990 33, 21-31.
J. Med. Chem. 1998 41, 4995-5001.
J. Med. Chem. 1998 41, 5410-12.
J. Med. Chem. 1998 41, 3821-30.
J. Med. Chem. 1998 41, 291-301.
Biorg. Med. Chem. Letters. 1997, 7 (23) 2959-2962.
Smith R., "Recent Advances in the Research and Development of RAF Kinase Inhibitors," 6 Current Topics in Medinical Chemistry, 1071 (2006).
King, Frank, Medicinal Chemistry, Principles and Practice (2$^{nd}$ Ed. 2002) pp. ix-xx.
Foye's Principles of Medicinal Chemistry, (6$^{th}$ Ed. 2008), pp. xiii-xix.
Bayer's Final Mediation Brief—Apr. 28, 2010.
Goldsmith, Elizabeth J., et al., Current Opinion in Structural Biology, 4, 1994, pp. 833-840.
Gray, N.S., et al., "Exploiting chemical libraries, structure, and genomics in the search for kinase inhibitors," Science, 281, 1998, pp. 533-538.
Wang, Z., et al., "Structural basis of inhibitor selectivity in MAP kinases," Structure, 6, 1998. pp. 1117-1128.
Wilson, K.P., et al., "The structural basis for the specificity of pyridinylimidazole inhibitors of p38 MAP kinase," Chem. Biol., 4, 1997, pp. 423-431.
Tong, et al., "A highly specific inhibitor of human P38 MAP kinase binds in the ATP pocket," Nature Struct. Biol., 4, 1997, pp. 311-316.
Pawson, T., et al., "Association of the Shc and Grb2/Sem5 SH2-containing proteins is implicated in activation of the Ras pathway by tyrosine kinases," Nature, 360, 1992, pp. 689-692.
Fabian, J.R., et al., "Critical tyrosine residues regulate the enzymatic and biological activity of Raf-1 kinase," Mol. Cell. Biol., 13, Nov. 1993, pp. 7170-7179.
Jelinek, T., et al., "Ras-induced activation of Raf-1 is dependent on tyrosine phosphorylation," Mol. Cell. Biol., 16, Mar. 1996, pp. 1027-1034.
Avruch, J., et al., Trends Boichem. Sci., 19, 1994, pp. 279-283.
Marshall, M.S., FASEB J., 9, 1995, pp. 1311-1318.
Leevers, S.J., et al., Nature, 369, 1994, pp. 411-414.
Stokoe, D., et al al., Science, 264, 1994, pp. 1463-1467.
Carroll, M.P., et al., J. Biol. Chem., 269, 1994, pp. 1249-1256.
Fabian, J.R., et al., Mol. Cell. Biol., 13, 1993, pp. 7170-7179.
Marais, R., et al., EMBO J., 14, 1995, pp. 3136-3145.
Ueda, Y., et al., J. Biol. Chem., 271, 1996, pp. 23512-23519.
Schonwasser, D.C., et al., Mol. Cell. Biol., 18, 1998, pp. 790-798.
Fanti, W.J., et al., Nature, 371, 1994, pp. 612-614.
Freed, E., et al., Science, 265, 1994, pp. 1713-1716.
Fu, H., et al., Science, 266, 1994, pp. 126-129.
Li, S., et al., EMBO J., 14, 1995, pp. 685-696.
Roy, S., et al., Mol. Cell. Biol., 18, 1998, pp. 3947-3955.
Alessi, D.R. et al., EMBO J., 13, 1994, pp. 1610-1619.
Yan, M., et al., J. Biol. Chem., 269, 1994, pp. 19067-19073.
Seger, R., et al., J. Biol. Chem., 267, 1992, pp. 14373-14381.
Payne, D.M., et al., EMBO J., 10, 1991, pp. 885-892.
Treisman, R., Curr. Opin. Cell Biol., 8, 1996, pp. 205-215.
Kelly, T.R., et al., "Relative Binding Affinity of Carboxylate and Its Isosteres: Nitro, Phosphate, Phosphonate, Sulfonate, and δ-Lactone," J. Am. Chem. Soc., 116, 1994, pp. 7072-7080.
Hanks, S.K., et al., "The Protein Kinase Family: Conserved Features and Deduced Phylogeny of the Catalytic Domains," Science, 241, 1988, pp. 45-52.
Sternberg, M.J.E., et al., "Modelling the ATP-binding site of oncogene products, the epidermal growth factor receptor and related proteins," FEBS 1821, 175, 2, Oct. 1984, pp. 387-392.
Zhang, F., et al., "Atomic structure of the MAP kinase ERK2 at 2.3 Å resolution," Nature, 367, Feb. 24, 1994, pp. 704-711.
DeBondt, H.L., et al., "Crystal structure of cyclin-dependent kinase 2," Nature, 363, Jun. 17, 1993, pp. 595-602.
Hansch, C., et al., "Comparative QSAR: Toward a Deeper Understanding of Chemicobiological Interactions," Chem. Rev., 96, 1996, pp. 1045-1075.
Patani, G.A., et al., "Bioisosterism: A Rational Approach in Drug Design," Chem. Rev., 96, 1996, pp. 3147-3176.
Hammett Equation, Wikipedia, pp. 1-10, http://en.wikipedia.org/wiki/Hammett_equation, page updated Jul. 3, 2012.
Shams El Din, A.M., et al., "A Thermometric Study on the Stability of Di-Butyl Thiourea in Acid Solutions," Thermochimica Acta, 105, 1986, pp. 91-100.
Il Finar, Organic Chemistry, vol. 1, Sixth Ed., 1972, 7 pages—Cover page, Table of Contents (5 pages), p. 464.
Borisenko, V.E., et al., "Hydrogen Bond and Electro-Optical Parameters of Chlorosubstituted Aniline," Journal of Molecular Structure, 239, 1990, pp. 13-21.
Strauss, M.J., "The Nitroaromatic Group in Drug Design. Pharmacology and Toxicology (for Nonpharmacologists)," Ind. Eng. Chem. Prod. Res. Dev., 18, 3, 1979, pp. 158-165.
Mann, J., "Modern Methods for the Introduction of Fluorine into Organic Molecules: An Approach to Compounds with Altered Chemical and Biological Activities," Chem. Soc. Rev., 16, 1987, pp. 381-436.
McClinton, M.A., et al., "Triflroromethylations and Related Reactions in Organic Chemistry," Tetrahedron, 48, 32, 1992, pp. 6555-6666.
Prabhumirashi, L.S., et al., "Excited state dipole moments in chloroanilines and chlorophenols from solvatochromic shifts in electronic absorption spectra: support for the concept of excited state group moments," Spectrochimica Acta, 40A, 10, 1984, pp. 953-958.
Hepworth, J.D., et al., "A Dipole Moment Study of the Electrical Effect of the Trifluoromethyl Group," J. Chem. Soc. Perkin II, 1972, pp. 1905-1908.
Holtz, D., "A Critical Examination of Fluorine Hyperconjugation in Aromatic Systems," Chem. Rev., 71, 1971, pp. 139-145.
Grandberg, I.I., et al., "Comparative Basicities of Substituted Pyridines and Electronegativity Series for Substituents in the Pyridine Series," Khimiya Geterotsiklicheskikh Soedinenil, 2, 4, 1966, pp. 561-566.
Baguley, B.C., et al., "Synthesis, Antitumor Activity, and DNA Binding Properties of a New Derivative of Amsacrine N-5-Dimethyl-9-[(2-methoxy-4-methylsulfonylamino)phenylamino]-4-acridinecaboxamide," Cancer Research, 44, Aug. 1984, pp. 3245-3251.
Kestell, P., et al., "Disposition of Amsacrine and Its Analogue 9-({Methoxy-4-[(methylsulfonyl)-amino]phenyl]amino)-N,5-dimethyl-4-acridinecarboxamide (CI-921) in Plasma, Liver, and Lewis Lung Tumors in Mice," Cancer Research, 50, Feb. 1, 1989, pp. 503-508.
Atwell, G.J., "Potential Antitumor Agents. 50. In Vivo Solid-Tumor Activity of Derivatives of N-[2-(Dimethylamino)ethyl]acridine-4-carboxamide," J. Med. Chem., 30, 1987, pp. 664-669.

(56) References Cited

OTHER PUBLICATIONS

Moreira, R., et al., "A New Direct Synthesis of Tertiary N-Acyloxymethylamide Prodrugs of Carboxylic Acid Drugs," Tetrahedron Letters, 35, 38, 1994, pp. 7107-7110.
Filler, R., et al., Organo-fluorine Compounds in Medicinal and Biomedical Applications, Eds., Elsevier; Amsterdam, 1993. Cover and Table of Contents (2 pages).
Kumar, S., et al., "Synthesis and Evaluation of Amide Prodrugs of Diclofenac," J. Pharma. Sci. & Res., 2, 6, 2010, pp. 369-375.
Wilhelm, S., et al., "Discovery and development of sorafenib: a multikinase inhibitor for treating cancer," Nature Reviews Drug Discovery, 5, Oct. 2006, pp. 835-844.
Garcia, J.G.N., et al., "Genomic assessment of a multikinase inhibitor, sorafenib, in a rodent model of pulmonary hypertension," Physiol. Genomics, 33, 3, 2008, pp. 278-291.
Wilhelm, S.M., et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis," Cancer Research, 64, 19, 2004, pp. 7099-7109.
Torino, F., et al., "Hypothyroidism related to tyrosine kinase inhibitors: an emerging toxic effect of targeted therapy," Nature Reviews Clinical Oncology, 6, 4, Apr. 2009, pp. 219-228.
Fabian, M.A., et al., "A small molecule-kinase interaction map for clinical kinase inhibitors," Nature Biotechnology, 23, 3, Mar. 2005, pp. 329-336.
Bain, J., et al., "The selectivity of protein kinase inhibitors: a further update," Biochem J., 408, 2007, pp. 297-315.
Web Publication—"Reactions of Carboxylic Acids, 1. Salt Formation," Carboxylic Acid Reactions, Abstract, downloaded from http://www.cem.msu.edu/~reusch/VirtualText/crbacid1.htm, May 26, 2005, 2 pages.
International Search Report issued in International Application No. PCT/US2004/023500, mailed Feb. 11, 2005, 2 pages.
Examination Report issued in EP 04 786 091.1, dated Jul. 20, 2006, 2 pages.
Web Publication—"International Nonproprietary Names for Pharmaceutical Substances (INN)" WHO Drug Information, 17, 4, 2003, proplist88.pdf (2003), pp. 267-286, downloaded from www.who.int.
Bolton, G.L., et al., "Chapter 17. Ras Oncogene Directed Approaches in Cancer Chemotherapy," Annual Reports in Medicinal Chemistry, 29, Section III—Chemotherapeutic Agents, Plattner Ed., Copyright 1994 by Academic Press, Inc., pp. 165-174.
Hubbard, Stevan R., "Oncogenic Mutations in B-Raf: Some Losses Yield Gains," Cell, 116, 6, Mar. 19, 2004, pp. 764-766.
Jeffcoat, A. R. et al., "The Metabolism and Toxicity of Halogenated Carbanilides . . . ," Drug Metabolism and Disposition, 5, 2, Aug. 19, 1976, pp. 157-166.
Leuner, C., et al., "Improving drug solubility for oral delivery using solid dispersions," European Journal of Pharmaceuticals and Biopharmaceuticals, 50, 2000, pp. 47-60.
Moelling, K, et al., "Signal Transduction as Target of Gene Therapy," Cancer Research, 142, 1996, pp. 63-71.
Ravi, R.K., et al., "Advanced Raf-1 Causes Growth Arrest in Human Small Cell Lung Cancer Cells," J. Clin. Invest., 101, 1, Jan. 1998, pp. 153-159.
Strumberg, D., et al., "Phase 1 Clinical, Pharmacokinetic and Pharmacodynamic Study of the Raf Kinase Inhibitor BAY 43-9006 in Patients with Locally Advanced or Metastatic Cancer," Presented at the 2001 ASCO Annual Meeting, America Society of Clinical Oncology, Abstract No. 330, downloaded from http://www.asco.org/portal/site/ASCO/template.RAW/menuitem.
34d60f5624ba07fd506fe3 . . . , Dec. 17, 2008, 2 pages.
Iwadate, Y., et al., "Chemotherapy for brain metastases from lung cancer: comparison of cases with and without intra-arterial mannitol infusion," Neurological Surgery, 21, 6, Jun. 1993, pp. 513-518, Abstract Medline/NLM Abstract No. NLM8336809, XP-002233466.
Riedl, B., et al., "Potent Raf Kinase Inhibitors from the Diphenylurea Class: Structure Activity Relationships," PD, 3, 2001, p. 923, Abstract # 4956.
Dickore, K., et al., "Plant Growth Regulating Compositions—Containing 2-Amino-Furan or 2-Amino-Thiopene Derivatives," Bayer AG, Abstract: EP 4931 A, Dec. 23, 1980.
Mitsubishi Kasei Corporation, EP 405233 A1, published Jan. 2, 1991, Abstract—1991 Derwent Publications Ltd., No. 91-008629/02-B05, MITU 15/06.89, 2 pages.
Mitsubishi Kasei Corporation, EP 405233 A1, published Jan. 2, 1991, Abstract—1991 1 page, Cite No. IXb.
Vippagunta, S.R., et al., "Crystalline Solids," Advanced Drug Delivery Reviews 48, 2001, pp. 3-26.
Dorwald F.A. Side Reactions in Organic Synthesis, 2005, Wiley VCH Weinheim, p. IX of Preface.
Silverman, Richard B.; The Organic Chemistry of Drug Design and Drug Action, Elsevier Academic Press, 2d Ed., 2004, pp. 29-32.
Favaro et al, "Targeted thereapy in renal cell carcinoma" Pub Med. PMID: 16185167.
Gollob et al, "Sorafenib: scientific rationales for single-agent and combination therapy in clear-cell renal cell carcinoma" Pub Med PMID: 16425993.
Reddy et al, "Sorafeninb: recent update on activity as a single agent and in combination with interferon-alpha2 in patients with advanced-stage renal cell carcinoma." Pub Med PMID: 16729906.
Takimoto et al, "Safety and anti-tumor activity of sorafenib (Nexavar®) in combination with other anti-cancer agents: a review of clinical trials." Cancer Chemotherapy and Pharmacology © Springer-Verlag 2007. 10.1007/s00280-007-0639-9.
Lago et al, "Selected combination therapy with Sorafenib: A Review of clinical data and perspectives in advanced solid tumors" The Oncologist, vol. 13, No. 8, 845-858 (Aug. 11, 2008) doi: 10.1634/theoncologist. 2007-0233 © 2008 AlphaMed Press.
Kolch et al, "The role of Raf kinases in malignant transformation" (Apr. 25, 2002) ISSN: 1462-3994 © Cambridge University Press.
Nicholas et al, "Overview of ras oncogenes and their clinical potential".
Wald et al, "Involvement of the CXCL12/CXCR4 pathway in the advanced liver disease that is associated with hepatitis C virus or hepatitis B virus." Eur. J. Immunol, vol. 34, p. 1164-1174 (2004).
Thelen et al, "VEGF-D promotes tumor growth and lymphatic spread in a mouse model of hepatocellular carcinoma" Int. J. Cancer 122, 2471-2481 (2008) © 2008 Wiley-Liss, Inc.
Hilger et al, "Inhibition of ERK phosphorylation and clinical outcome in patients treated with the Raf kinase inhibitor Bay 43-9006" Proc Am Soc Clin Oncol 21: 2002 (abstr 1916).
Oka et al, "Constitutive Activation of Mitogen-activated Protein (MAP) kinases in human renal cell carcinoma" Cancer Research 55, 4182-4187, (Sep. 15, 1995).
Chow et al, "Measurement of Map kinase activation by flow cytometry using phospho-specific antibodies to MEK and ERK: potential for pharmacodynamic monitoring of signal transduction inhibitors" Cytometry (Communications in Clinical Cytometry) 46:72-78 (2001).
Kumar et al, "Drugs targeted against protein kinases" 2001 © Ashley publications ltd. ISSN: 1462-2416.
Carter et al, "Chemotherapy of Cancer (second edition)" Wiley Medical (Prior to Aug. 13, 1981).
Wood et al, "Novel RAF Kinase Inhibitor Bay 43-9006 Shows Early Signs of Tolerability and Activity in Phase 1B Combination Trials Reported at ASCO." (Press Release: Jun. 2, 2003).
Heim Martina et al, "The Raf kinase inhibitor Bay 43-9006 reduces cellular uptake of platinum compounds and cytotoxicity in human colorectal carcinoma cell lines." Anti-Cancer Drugs Feb. 2005, vol. 16, No. 2 Feb. 2005 pp. 129-136.
Tang et al, "Inhaled nitric oxide attenuates pulmonary hypertension and improves lung growth in infant rats after neonatal treatment with a VEGF receptor inhibitor." Am J Physiol Lung Cell Mol. Physiol 287: L344-L351.
Cras et al, "Treatment of newborn rats with a VEGF receptor inhibitor causes pulmonary hypertension and abnormal lung structure." Am J Physiol Lung Cell Mol Physiol vol. 283, Issue 3, L555-L562, 2002.
O'Dwyer et al, "c-raf-1 Depletion and tumor responses in patients treated with the c-raf-1 Antisense Olgodeoxynucleotide ISIS 5132 (CGP 69846A)." Clinical Cancer Research vol. 5 pp. 3977-3982 (Dec. 1999).

(56) References Cited

OTHER PUBLICATIONS

Mita et al, "The molecular target of rapamycin (mTOR) as a therapeutic target against cancer." Cancer Biology & Therapy 2:4 Suppl. 1, S169-S177 (Jul./Aug. 2003).
Herlaar et al, "p38 MAPK signaling cascades in inflammatory disease." Molecular Medicine Today, vol. 5 pp. 139-147 (Oct. 1999).
Pending claims of U.S. Appl. No. 09/776,936, filed Dec. 22, 1998.
Pending claims of U.S. Appl. No. 09/458,014, filed Dec. 10, 1999.
Pending claims of U.S. Appl. No. 11/932,548, filed Oct. 31, 2007.
Yu et al, "The role of Mcl-1 downregulation in the proapoptotic activity of the multikinase inhibitor BAY 43-9006." PMID: 16007148.
Rahmani et al, "Apoptosis induced by the kinase inhibitor BAY 43/9006 in human leukemia cells involves downregulation of MCL-1 through inhibition of translation." JBC Papers in Press Manuscript M506551200 (Aug. 18, 2005).
Milano et al, "New molecular targeted therapies in thyroid cancer" Anti-Cancer Drugs (2006) © Lippincott Williams & Wilkins.
Chustecka et al, "Bortezomib and Sorafenib Show Activity in Thyroid Cancer" Medscape (Nov. 2, 2006).
Tanaka et al, "Current status and perspective of antiangiogenic therapy for cancer: hepatocellular carcinoma" Int J Clin Oncol (2006) 11:82-89 (Jan. 31, 2006).
Strumberg et al, "Phase I Clinical, Pharmacokinetic and Pharmacodynamic Study of the Raf Kinase Inhibitor BAY 43-9006 in Patients with Locally Advanced or Metastatic Cancer" Proc Am Soc Clin Oncol 20: 2001 (abstr 330).
Lorigan et al, "Phase II trial of sorafenib combined with dacarbazine in metastatic melanoma patients" ASCO DTIC abstract (Jan. 11, 2006).
Naumann et al, "Raf protein serine/threonine kinases" Chapter 7.
Storm et al, "raf Oncogenes in Carcinogenesis" Critical Reviews in Oncogenesis, vol. 2, Issue 1.
Naumann et al, "The Role of Raf Kinases in Development and Growth of Tumors" Recent Results in Cancer Research, vol. 143 (1997).
European Medicines Agency, "Chimp Assessment Report for Nexavar" Doc Ref: EMEA/CHMP/140610/2006.
Gatzemeier et al, "Phase II trial of single-agent sorafenib in patients with advanced non-cell lung carcinoma." Journal of Clinical Oncology, 2006 ASCO Annual Meeting Proceedings Part I vol. 24, No. 18S (Jun. 20 Supplement) 2006.
Gridelli et al, "Sorafenib and Sunitinib in the treatment of advanced non-small cell lung cancer" The Oncologist Lung Cancer (2007) 12:191-200.
Hilger et al, "ERK1/2 phosphorylation: a biomarker analysis within a phase I study with the new Raf kinase inhibitor Bay 43-9006" International journal of clinical pharmacology and therapeutics, vol. 40, No. 12 567-568 (2002).
Hilger et al, "Correlation of ERK-phosphorylation and toxicities in patients treated with the Raf kinase inhibitor BAY 43-9006" International journal of clinical pharmacology and therapeutics, vol. 42, No. 11, 648-649 (2004).
Flaherty et al, "A Phase I Trial of the Oral, Multikinase Inhibitor Sorafenib in Combination with Carboplatin and Paclitaxel" Clin Cancer Res 41(15) (Aug. 1, 2008).

* cited by examiner

FLUORO SUBSTITUTED OMEGA-CARBOXYARYL DIPHENYL UREA FOR THE TREATMENT AND PREVENTION OF DISEASES AND CONDITIONS

This application claims the benefit of the filing date of U.S. Provisional Application Ser. No. 60/489,102 filed Jul. 23, 2003 and U.S. Provisional Application Ser. No. 60/540,326 filed Feb. 2, 2004.

FIELD OF THE INVENTION

This invention relates to novel compounds, pharmaceutical compositions containing such compounds and the use of those compounds or compositions for treating diseases and conditions mediated by abnormal VEGFR, PDGFR, raf, p38, and/or flt-3 kinase signaling, either alone or in combination with anti-cancer agents.

BACKGROUND OF THE INVENTION

Activation of the ras signal transduction pathway indicates a cascade of events that have a profound impact on cellular proliferation, differentiation, and transformation. Raf kinase, a downstream effector of ras, is recognized as a key mediator of these signals from cell surface receptors to the cell nucleus (Lowy, D. R.; Willumsen, B. M. *Ann. Rev. Biochem.* 1993, 62, 851; Bos, J. L. *Cancer Res.* 1989, 49, 4682). It has been shown that inhibiting the effect of active ras by inhibiting the raf kinase signaling pathway by administration of deactivating antibodies to raf kinase or by co-expression of dominant negative raf kinase or dominant negative MEK, the substrate of raf kinase, leads to the reversion of transformed cells to the normal growth phenotype (see: Daum et al. *Trends Biochem. Sci.* 1994, 19, 474-80; Fridman et al. *J. Biol. Chem.* 1994, 269, 30105-8. Kolch et al. (*Nature* 1991, 349, 426-28) have further indicated that inhibition of raf expression by antisense RNA blocks cell proliferation in membrane-associated oncogenes. Similarly, inhibition of raf kinase (by antisense oligodeoxynucleotides) has been correlated in vitro and in vivo with inhibition of the growth of a variety of human tumor types (Monia et al., *Nat. Med.* 1996, 2, 668-75).

To support progressive tumor growth beyond the size of 1-2 mm$^3$, it is recognized that tumor cells require a functional stroma, a support structure consisting of fibroblast, smooth muscle cells, endothelial cells, extracellular matrix proteins, and soluble factors (Folkman, J., *Semin. Oncol.* 2002. 29(6 Suppl 16), 15-8). Tumors induce the formation of stromal tissues through the secretion of soluble growth factors such as PDGF and transforming growth factor-beta (TGF-beta), which in turn stimulate the secretion of complimentary factors by host cells such as fibroblast growth factor (FGF), epidermal growth factor (EGF), and vascular endothelial growth factor (VEGF). These stimulatory factors induce the formation of new blood vessels, or angiogenesis, which brings oxygen and nutrients to the tumor and allows it to grow and provides a route for metastasis. It is believed some therapies directed at inhibiting stroma formation will inhibit the growth of epithelial tumors from a wide variety of histological types. (George, D. *Semin. Oncol.* 2001. 28(5 Suppl 17), 27-33; Shaheen, R. M., et al., *Cancer Res.* 2001, 61(4), 1464-8; Shaheen, R. M., et al. *Cancer Res.* 1999, 59(21), 5412-6). However, because of the complex nature and the multiple growth factors involved in angiogenesis process and tumor progression, an agent targeting a single pathway may have limited efficacy. It is desirable to provide treatment against a number of key signaling pathways utilized by tumors to induce angiogenesis in the host stroma. These include PDGF, a potent stimulator of stroma formation (Ostman, A. and C. H. Heldin, *Adv. Cancer Res.* 2001, 80, 1-38), FGF, a chemoattractant and mitogen for fibroblasts and endothelial cells, and VEGF, a potent regulator of vascularization.

PDGF is a key regulator of stromal formation, which is secreted by many tumors in a paracrine fashion and is believed to promote the growth of fibroblasts, smooth muscle and endothelial cells, promoting stroma formation and angiogenesis. PDGF was originally identified as the v-sis oncogene product of the simian sarcoma virus (Heldin, C. H., et al., *J. Cell. Sci. Suppl.* 1985, 3, 65-76). The growth factor is made up of two peptide chains, referred to as A or B chains which share 60% homology in their primary amino acid sequence. The chains are disulfide cross linked to form the 30 kDa mature protein composed of either AA, BB or AB homo- or heterodimmers. PDGF is found at high levels in platelets, and is expressed by endothelial cells and vascular smooth muscle cells. In addition, the production of PDGF is up regulated under low oxygen conditions such as those found in poorly vascularized tumor tissue (Kourembanas, S., et al., *Kidney Int.* 1997, 51(2), 438-43). PDGF binds with high affinity to the PDGF receptor, a 1106 amino acid 124 kDa transmembrane tyrosine kinase receptor (Heldin, C. H., A. Ostman, and L. Ronnstrand, *Biochim. Biophys. Acta* 1998, 1378(1), 79-113). PDGFR is found as homo- or heterodimer chains which have 30% homology overall in their amino acid sequence and 64% homology between their kinase domains (Heldin, C. H., et al., *Embo J.* 1988, 7(5), 1387-93). PDGFR is a member of a family of tyrosine kinase receptors with split kinase domains that includes VEGFR-2 (KDR), VEGFR-3 (flt-4), c-kit, and flt-3. The PDGF receptor is expressed primarily on fibroblasts, smooth muscle cells, and pericytes and to a lesser extent on neurons, kidney mesangial, Leydig, and Schwann cells of the central nervous system. Upon binding to the receptor, PDGF induces receptor dimerization and undergoes auto- and trans-phosphorylation of tyrosine residues which increase the receptors' kinase activity and promotes the recruitment of downstream effectors through the activation of SH2 protein binding domains. A number of signaling molecules form complexes with activated PDGFR including PI-3-kinase, phospholipase C-gamma, src and GAP (GTPase activating protein for p21-ras) (Soskic, V., et al. *Biochemistry* 1999, 38(6), 1757-64). Through the activation of PI-3-kinase, PDGF activates the Rho signaling pathway inducing cell motility and migration, and through the activation of GAP, induces mitogenesis through the activation of p21-ras and the MAPK signaling pathway.

In adults, it is believed the major function of PDGF is to facilitate and increase the rate of wound healing and to maintain blood vessel homeostasis (Baker, E. A. and D. J. Leaper, *Wound Repair Regen.* 2000, 8(5), 392-8, and Yu, J., A. Moon, and H. R. Kim, *Biochem. Biophys. Res. Commun.* 2001, 282 (3), 697-700). PDGF is found at high concentrations in platelets and is a potent chemoattractant for fibroblast, smooth muscle cells, neutrophils and macrophages. In addition to its role in wound healing PDGF is known to help maintain vascular homeostasis. During the development of new blood vessels, PDGF recruits pericytes and smooth muscle cells that are needed for the structural integrity of the vessels. PDGF is thought to play a similar role during tumor neovascularization. As part of its role in angiogenesis PDGF controls interstitial fluid pressure, regulating the permeability of vessels through its regulation of the interaction between connective tissue cells and the extracellular matrix. Inhibiting PDGFR activity can lower interstitial pressure and facilitate the influx of cytotoxics into tumors improving the anti-tumor efficacy of these agents (Pietras, K., et al. *Cancer Res*. 2002, 62(19), 5476-84; Pietras, K., et al. *Cancer Res*. 2001, 61(7), 2929-34).

PDGF can promote tumor growth through either the paracrine or autocrine stimulation of PDGFR receptors on stromal cells or tumor cells directly, or through the amplification of the receptor or activation of the receptor by recombination. Over expressed PDGF can transform human melanoma cells and keratinocytes (Forsberg, K., et al. *Proc. Natl. Acad Sci. U S A*. 1993, 90(2), 393-7; Skobe, M. and N. E. Fusenig, *Proc. Natl. Acad. Sci. U S A*. 1998, 95(3), 1050-5), two cell types that do not express PDGF receptors, presumably by the direct effect of PDGF on stroma formation and induction of angiogenesis. This paracrine stimulation of tumor stroma is also observed in carcinomas of the colon, lung, breast, and prostate (Bhardwaj, B., et al. *Clin. Cancer Res*. 1996, 2(4), 773-82; Nakanishi, K., et al. *Mod. Pathol*. 1997, 10(4), 341-7; Sundberg, C., et al. *Am. J. Pathol*. 1997, 151(2), 479-92; Lindmark, G., et al. *Lab. Invest*. 1993, 69(6), 682-9; Vignaud, J. M., et al, *Cancer Res*. 1994, 54(20), 5455-63) where the tumors express PDGF, but not the receptor. The autocrine stimulation of tumor cell growth, where a large faction of tumors analyzed express both the ligand PDGF and the receptor, has been reported in glioblastomas (Fleming, T. P., et al. *Cancer Res*. 1992, 52(16), 4550-3), soft tissue sarcomas (Wang, J., M. D. Coltrera, and A. M. Gown, *Cancer Res*. 1994, 54(2), 560-4) and cancers of the ovary (Henriksen, R., et al. *Cancer Res*. 1993, 53(19), 4550-4), prostate (Fudge, K., C. Y. Wang, and M. E. Stearns, *Mod. Pathol*. 1994, 7(5), 549-54), pancreas (Funa, K., et al. *Cancer Res*. 1990, 50(3), 748-53) and lung (Antoniades, H. N., et al., *Proc. Natl. Acad. Sci. U S A* 1992, 89(9), 3942-6). Ligand independent activation of the receptor is found to a lesser extent but has been reported in chronic myelomonocytic leukemia (CMML) where the a chromosomal translocation event forms a fusion protein between the Ets-like transcription factor TEL and the PDGF receptor. In addition, activating mutations in PDGFR have been found in gastrointestinal stromal tumors in which c-kit activation is not involved (Heinrich, M. C., et al., *Science* 2003, 9, 9).

Another major regulator of angiogenesis and vasculogenesis in both embryonic development and some angiogenic-dependent diseases is vascular endothelial growth factor (VEGF; also called vascular permeability factor, VPF). VEGF represents a family of isoforms of mitogens existing in homodimeric forms due to alternative RNA splicing. The VEGF isoforms are highly specific for vascular endothelial cells (for reviews, see: Farrara et al. *Endocr. Rev*. 1992, 13, 18; Neufield et al. *FASEB J*. 1999, 13, 9).

VEGF expression is induced by hypoxia (Shweiki et al. *Nature* 1992, 359, 843), as well as by a variety of cytokines and growth factors, such as interleukin-1, interleukin-6, epidermal growth factor and transforming growth factor. To date, VEGF and the VEGF family members have been reported to bind to one or more of three transmembrane receptor tyrosine kinases (Mustonen et al. *J. Cell Biol*. 1995, 129, 895), VEGF receptor-1 (also known as flt-1 (fms-like tyrosine kinase-1)), VEGFR-2 (also known as kinase insert domain containing receptor (KDR); the murine analogue of VEGFR-2 is known as fetal liver kinase-1 (flk-1)), and VEGFR-3 (also known as flt-4). VEGFR-2 and flt-1 have been shown to have different signal transduction properties (Waltenberger et al. *J. Biol. Chem*. 1994, 269, 26988); Park et al. *Oncogene* 1995, 10, 135). Thus, VEGFR-2 undergoes strong ligand-dependant tyrosine phosphorylation in intact cells, whereas flt-1 displays a weak response. Thus, binding to VEGFR-2 is believed to be a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. It is believed that regulation of the VEGF-mediated signal transduction cascade by some agents can provide a useful control of abnormal angiogenesis and/or hyperpermeability processes. Tumorigenic cells within hypoxic regions of tumors respond by stimulation of VEGF production, which triggers activation of quiescent endothelial cells to stimulate new blood vessel formation. (Shweiki et al. *Proc. Nat'l. Acad Sci*. 1995, 92, 768). In addition, VEGF production in tumor regions where there is no angiogenesis may proceed through the ras signal transduction pathway (Grugel et al. *J. Biol. Chem*. 1995, 270, 25915; Rak et al. *Cancer Res*. 1995, 55, 4575). In situ hybridization studies have demonstrated VEGF mRNA is strongly upregulated in a wide variety of human tumors, including lung (Mattern et al. *Br. J. Cancer* 1996, 73, 931), thyroid (Viglietto et al. *Oncogene* 1995, 11, 1569), breast (Brown et al. *Human Pathol*. 1995, 26, 86), gastrointestinal tract (Brown et al. *Cancer Res*. 1993, 53, 4727; Suzuki et al. *Cancer Res*. 1996, 56, 3004), kidney and bladder (Brown et al. *Am. J. Pathol*. 1993, 143I, 1255), ovary (Olson et al. *Cancer Res*. 1994, 54, 1255), and cervical (Guidi et al. *J. Nat'l Cancer Inst*. 1995, 87, 12137) carcinomas, as well as angiosarcoma (Hashimoto et al. *Lab. Invest*. 1995, 73, 859) and several intracranial tumors (Plate et al. *Nature* 1992, 359, 845; Phillips et al. *Int. J. Oncol*. 1993, 2, 913; Berkman et al. *J. Clin. Invest*. 1993, 91, 153). Neutralizing monoclonal antibodies to VEGFR-2 have been shown to be efficacious in blocking tumor angiogenesis (Kim et al. *Nature* 1993, 362, 841; Rockwell et al. *Mol. Cell. Differ*. 1995, 3, 315).

Overexpression of VEGF, for example under conditions of extreme hypoxia, can lead to intraocular angiogenesis, resulting in hyperproliferation of blood vessels, leading eventually to blindness. Such a cascade of events has been observed for a number of retinopathies, including diabetic retinopathy, ischemic retinal-vein occlusion, and retinopathy of prematurity (Aiello et al. *New Engl. J. Med*. 1994, 331, 1480; Peer et al. *Lab. Invest*. 1995, 72, 638), and age-related macular degeneration (AMD; see, Lopez et al. *Invest. Opththalmol. Vis. Sci*. 1996, 37, 855).

In rheumatoid arthritis (RA), the in-growth of vascular pannus may be mediated by production of angiogenic factors. Levels of immunoreactive VEGF are high in the synovial fluid of RA patients, while VEGF levels were low in the synovial fluid of patients with other forms of arthritis of with degenerative joint disease (Koch et al. *J. Immunol*. 1994, 152, 4149). The angiogenesis inhibitor AGM-170 has been shown to prevent neovascularization of the joint in the rat collagen arthritis model (Peacock et al. *J. Exper. Med*. 1992, 175, 1135).

Increased VEGF expression has also been shown in psoriatic skin, as well as bullous disorders associated with subepidermal blister formation, such as bullous pemphigoid, erythema multiforme, and dermatitis herpetiformis (Brown et al. *J. Invest. Dermatol*. 1995, 104, 744).

The vascular endothelial growth factors (VEGF, VEGF-C, VEGF-D) and their receptors (VEGFR-2, VEGFR-3) are not only key regulators of tumor angiogenesis, but also lymphangiogenesis. VEGF, VEGF-C and VEGF-D are expressed in most tumors, primarily during periods of tumor growth and, often at substantially increased levels. VEGF expression is stimulated by hypoxia, cytokines, oncogenes such as ras, or by inactivation of tumor suppressor genes (McMahon, G. *Oncologist* 2000, 5(Suppl. 1), 3-10; McDonald, N. Q.; Hendrickson, W. A. *Cell* 1993, 73, 421-424)

The biological activities of the VEGFs are mediated through binding to their receptors. VEGFR-3 (also called flt-4) is predominantly expressed on lymphatic endothelium in normal adult tissues. VEGFR-3 function is needed for new lymphatic vessel formation, but not for maintenance of the pre-existing lymphatics. VEGFR-3 is also upregulated on blood vessel endothelium in tumors. Recently VEGF-C and VEGF-D, ligands for VEGFR-3, have been identified as regulators of lymphangiogenesis in mammals. Lymphangiogenesis induced by tumor-associated lymphangiogenic factors could promote the growth of new vessels into the tumor, providing tumor cells access to systemic circulation. Cells that invade the lymphatics could find their way into the bloodstream via the thoracic duct. Tumor expression studies have allowed a direct comparison of VEGF-C, VEGF-D and VEGFR-3 expression with clinicopathological factors that relate directly to the ability of primary tumors to spread (e.g., lymph node involvement, lymphatic invasion, secondary metastases, and disease-free survival). In many instances, these studies demonstrate a statistical correlation between the expression of lymphangiogenic factors and the ability of a primary solid tumor to metastasize (Skobe, M. et al. *Nature Med.* 2001, 7(2), 192-198; Stacker, S. A. et al., *Nature Med.* 2001, 7(2), 186-191; Makinen, T. et al. *Nature Med.* 2001, 7(2), 199-205; Mandriota, S. J. et al. *EMBO J.* 2001, 20(4), 672-82; Karpanen, T. et al. *Cancer Res.* 2001, 61(5), 1786-90; Kubo, H. et al. *Blood* 2000, 96(2), 546-53).

Hypoxia appears to be an important stimulus for VEGF production in malignant cells. Activation of p38 MAP kinase is required for VEGF induction by tumor cells in response to hypoxia (Blaschke, F. et al. *Biochem. Biophys. Res. Commun.* 2002, 296, 890-896; Shemirani, B. et al. *Oral Oncology* 2002, 38, 251-257). In addition to its involvement in angiogenesis through regulation of VEGF secretion, p38 MAP kinase promotes malignant cell invasion, and migration of different tumor types through regulation of collagenase activity and urokinase plasminogen activator expression (Laferriere, J. et al. *J. Biol. Chem.* 2001, 276, 33762-33772; Westermarck, J. et al. *Cancer Res.* 2000, 60, 7156-7162; Huang, S. et al. *J. Biol. Chem.* 2000, 275, 12266-12272; Simon, C. et al. *Exp. Cell Res.* 2001, 271, 344-355).

Inhibition of the mitogen-activated protein kinase (MAPK) p38 has been shown to inhibit both cytokine production (e.g., TNF, IL-1, IL-6, IL-8) and proteolytic enzyme production (e.g., MMP-1, MMP-3) in vitro and/or in vivo. The mitogen activated protein (MAP) kinase p38 is involved in IL-1 and TNF signaling pathways (Lee, J. C.; Laydon, J. T.; McDonnell, P. C.; Gallagher, T. F.; Kumar, S.; Green, D.; McNulty, D.; Blumenthal, M. J.; Heys, J. R.; Landvatter, S. W.; Stricker, J. E.; McLaughlin, M. M.; Siemens, I. R.; Fisher, S. M.; Livi, G. P.; White, J. R.; Adams, J. L.; Yound, P. R. *Nature* 1994, 372, 739).

Clinical studies have linked tumor necrosis factor (TNF) production and/or signaling to a number of diseases including rheumatoid arthritis (Maini. *J. Royal Coll. Physicians London* 1996, 30, 344). In addition, excessive levels of TNF have been implicated in a wide variety of inflammatory and/or immunomodulatory diseases, including acute rheumatic fever (Yegin et al. *Lancet* 1997, 349, 170), bone resorption (Pacifici et al. *J. Clin. Endocrinol. Metabol.* 1997, 82, 29), postmenopausal osteoporosis (Pacifici et al. *J. Bone Mineral Res.* 1996, 11, 1043), sepsis (Blackwell et al. *Br. J. Anaesth.* 1996, 77, 110), gram negative sepsis (Debets et al. *Prog. Clin. Biol. Res.* 1989, 308, 463), septic shock (Tracey et al. *Nature* 1987, 330, 662; Girardin et al. *New England J. Med* 1988, 319, 397), endotoxic shock (Beutler et al. *Science* 1985, 229, 869; Ashkenasi et al. *Proc. Nat'l. Acad. Sci. USA* 1991, 88, 10535), toxic shock syndrome, (Saha et al. *J. Immunol.* 1996, 157, 3869; Lina et al. *FEMS Immunol. Med. Microbiol.* 1996, 13, 81), systemic inflammatory response syndrome (Anon. *Crit. Care Med.* 1992, 20, 864), inflammatory bowel diseases (Stokkers et al. *J. Inflamm.* 1995-6, 47, 97) including Crohn's disease (van Deventer et al. *Aliment. Pharmacol. Therapeu.* 1996, 10 (Suppl. 2), 107; van Dullemen et al. *Gastroenterology* 1995, 109, 129) and ulcerative colitis (Masuda et al. *J. Clin. Lab. Immunol.* 1995, 46, 111), Jarisch-Herxheimer reactions (Fekade et al. *New England J. Med.* 1996, 335, 311), asthma (Amrani et al. *Rev. Malad Respir.* 1996, 13, 539), adult respiratory distress syndrome (Roten et al. *Am. Rev. Respir. Dis.* 1991, 143, 590; Suter et al. *Am. Rev. Respir. Dis.* 1992, 145, 1016), acute pulmonary fibrotic diseases (Pan et al. *Pathol. Int.* 1996, 46, 91), pulmonary sarcoidosis (Ishioka et al. *Sarcoidosis Vasculitis Diffuse Lung Dis.* 1996, 13, 139), allergic respiratory diseases (Casale et al. *Am. J. Respir. Cell Mol. Biol.* 1996, 15, 35), silicosis (Gossart et al. *J. Immunol.* 1996, 156, 1540; Vanhee et al. *Eur. Respir. J.* 1995, 8, 834), coal worker's pneumoconiosis (Borm et al. *Am. Rev. Respir. Dis.* 1988, 138, 1589), alveolar injury (Horinouchi et al. *Am. J. Respir. Cell Mol. Biol.* 1996, 14, 1044), hepatic failure (Gantner et al. *J. Pharmacol. Exp. Therap.* 1997, 280, 53), liver disease during acute inflammation (Kim et al. *J. Biol. Chem.* 1997, 272, 1402), severe alcoholic hepatitis (Bird et al. *Ann. Intern. Med.* 1990, 112, 917), malaria (Grau et al. *Immunol. Rev.* 1989, 112, 49; Taverne et al. *Parasitol. Today* 1996, 12, 290) including Plasmodium falciparum malaria (Perlmann et al. *Infect. Immunit.* 1997, 65, 116) and cerebral malaria (Rudin et al. *Am. J. Pathol.* 1997, 150, 257), non-insulin-dependent diabetes mellitus (NIDDM; Stephens et al. *J. Biol. Chem.* 1997, 272, 971; Ofei et al. *Diabetes* 1996, 45, 881), congestive heart failure (Doyama et al. *Int. J. Cardiol.* 1996, 54, 217; McMurray et al. *Br. Heart J.* 1991, 66, 356), damage following heart disease (Malkiel et al. *Mol. Med. Today* 1996, 2, 336), atherosclerosis (Parums et al. *J. Pathol.* 1996, 179, A46), Alzheimer's disease (Fagarasan et al. *Brain Res.* 1996, 723, 231; Aisen et al. *Gerontology* 1997, 43, 143), acute encephalitis (Ichiyama et al. *J Neurol.* 1996, 243, 457), brain injury (Cannon et al. *Crit. Care Med.* 1992, 20, 1414; Hansbrough et al. *Surg. Clin. N. Am.* 1987, 67, 69; Marano et al. *Surg. Gynecol. Obstetr.* 1990, 170, 32), multiple sclerosis (M. S.; Coyle. *Adv. Neuroimmunol.* 1996, 6, 143; Matusevicius et al. *J. Neuroimmunol.* 1996, 66, 115) including demyelation and oligiodendrocyte loss in multiple sclerosis (Brosnan et al. *Brain Pathol.* 1996, 6, 243), advanced cancer (MucWierzgon et al. *J. Biol. Regulators Homeostatic Agents* 1996, 10, 25), lymphoid malignancies (Levy et al. *Crit. Rev. Immunol.* 1996, 16, 31), pancreatitis (Exley et al. *Gut* 1992, 33, 1126) including systemic complications in acute pancreatitis (McKay et al. *Br. J. Surg.* 1996, 83, 919), impaired wound healing in infection inflammation and cancer (Buck et al. *Am. J. Pathol.* 1996, 149, 195), myelodysplastic syndromes (Raza et al. *Int. J. Hematol.* 1996, 63, 265), systemic lupus erythematosus (Maury et al. *Arthritis Rheum.* 1989, 32, 146), biliary cirrhosis (Miller et al. *Am. J. Gasteroenterolog.* 1992, 87, 465), bowel necrosis (Sun et al. *J. Clin. Invest.* 1988, 81, 1328), psoriasis (Christophers. *Austr. J. Dermatol.* 1996, 37, S4), radiation injury (Redlich et al. *J. Immunol.* 1996, 157, 1705), and toxicity following administration of monoclonal antibodies such as OKT3 (Brod et al. *Neurology* 1996, 46, 1633). TNF levels have also been related to host-versus-graft reactions (Piguet et al. *Immunol. Ser.* 1992, 56, 409) including ischemia reperfusion injury (Colletti et al. *J Clin. Invest.*

1989, 85, 1333) and allograft rejections including those of the kidney (Maury et al. *J. Exp. Med.* 1987, 166, 1132), liver (Imagawa et al. *Transplantation* 1990, 50, 219), heart (Bolling et al. *Transplantation* 1992, 53, 283), and skin (Stevens et al. *Transplant. Proc.* 1990, 22, 1924), lung allograft rejection (Grossman et al. *Immunol. Allergy Clin. N. Am.* 1989, 9, 153) including chronic lung allograft rejection (obliterative bronchitis; LoCicero et al. *J. Thorac. Cardiovasc. Surg.* 1990, 99, 1059), as well as complications due to total hip replacement (Cirino et al. *Life Sci.* 1996, 59, 86). TNF has also been linked to infectious diseases (review: Beutler et al. *Crit. Care Med.* 1993, 21, 5423; Degre. *Biotherapy* 1996, 8, 219) including tuberculosis (Rook et al. *Med. Malad. Infect.* 1996, 26, 904), *Helicobacter pylori* infection during peptic ulcer disease (Beales et al. *Gastroenterology* 1997, 112, 136), Chaga's disease resulting from *Trypanosoma cruzi* infection (Chandrasekar et al. *Biochem. Biophys. Res. Commun.* 1996, 223, 365), effects of Shiga-like toxin resulting from *E. coli* infection (Harel et al. *J. Clin. Invest.* 1992, 56, 40), the effects of enterotoxin A resulting from *Staphylococcus* infection (Fischer et al. *J. Immunol.* 1990, 144, 4663), meningococcal infection (Waage et al. *Lancet* 1987, 355; Ossege et al. *J. Neurolog. Sci.* 1996, 144, 1), and infections from *Borrelia burgdorferi* (Brandt et al. *Infect. ImmunoL.* 1990, 58, 983), *Treponema pallidum* (Chamberlin et al. *Infect. Immunol.* 1989, 57, 2872), cytomegalovirus (CMV; Geist et al. *Am. J. Respir. Cell Mol. Biol.* 1997, 16, 31), influenza virus (Beutler et al. *Clin. Res.* 1986, 34, 491a), Sendai virus (Goldfield et al. *Proc. Nat'l. Acad. Sci. USA* 1989, 87, 1490), Theiler's encephalomyelitis virus (Sierra et al. *Immunology* 1993, 78, 399), and the human immunodeficiency virus (HIV; Poli. *Proc. Nat'l. Acad. Sci. USA* 1990, 87, 782; Vyakaram et al. *AIDS* 1990, 4, 21; Badley et al. *J. Exp. Med.* 1997, 185, 55).

A number of diseases are thought to be mediated by excess or undesired matrix-destroying metalloprotease (MMP) activity or by an imbalance in the ratio of the MMPs to the tissue inhibitors of metalloproteinases (TIMPs). These include osteoarthritis (Woessner et al. *J. Biol. Chem.* 1984, 259, 3633), rheumatoid arthritis (Mullins et al. *Biochim. Biophys. Acta* 1983, 695, 117; Woolley et al. *Arthritis Rheum.* 1977, 20, 1231; Gravallese et al. *Arthritis Rheum.* 1991, 34, 1076), septic arthritis (Williams et al. *Arthritis Rheum.* 1990, 33, 533), tumor metastasis (Reich et al. *Cancer Res.* 1988, 48, 3307; Matrisian et al. *Proc. Nat'l. Acad. Sci., USA* 1986, 83, 9413), periodontal diseases (Overall et al. *J. Periodontal Res.* 1987, 22, 81), corneal ulceration (Burns et al. *Invest. Opthalmol. Vis. Sci.* 1989, 30, 1569), proteinuria (Baricos et al. *Biochem. J.* 1988, 254, 609), coronary thrombosis from atherosclerotic plaque rupture (Henney et al. *Proc. Nat'l. Acad. Sci., USA* 1991, 88, 8154), aneurysmal aortic disease (Vine et al. *Clin. Sci.* 1991, 81, 233), birth control (Woessner et al. *Steroids* 1989, 54, 491), dystrophobic epidermolysis bullosa (Kronberger et al. *J. Invest. Dermatol.* 1982, 79, 208), degenerative cartilage loss following traumatic joint injury, osteopenias mediated by MMP activity, tempero mandibular joint disease, and demyelating diseases of the nervous system (Chantry et al. *J. Neurochem.* 1988, 50, 688).

Because inhibition of p38 leads to inhibition of TNF production and MMP production, it is believed inhibition of mitogen activated protein (MAP) kinase p38 enzyme can provide an approach to the treatment of the above listed diseases including osteoporosis and inflammatory disorders such as rheumatoid arthritis and COPD (Badger, A. M.; Bradbeer, J. N.; Votta, B.; Lee, J. C.; Adams, J. L.; Griswold, D. E. *J. Pharm. Exper. Ther.* 1996, 279, 1453).

Hypoxia appears to be an important stimulus for VEGF production in malignant cells. Activation of p38 kinase is required for VEGF induction by tumor cells in response to hypoxia (Blaschke, F. et al. *Biochem. Biophys. Res. Commun.* 2002, 296, 890-896; Shemirani, B. et al. *Oral Oncology* 2002, 38, 251-257). In addition to its involvement in angiogenesis through regulation of VEGF secretion, p38 kinase promotes malignant cell invasion, and migration of different tumor types through regulation of collagenase activity and urokinase plasminogen activator expression (Laferriere, J. et al. *J. Biol. Chem.* 2001, 276, 33762-33772; Westermarck, J. et al. *Cancer Res.* 2000, 60, 7156-7162; Huang, S. et al. *J. Biol. Chem.* 2000, 275, 12266-12272; Simon, C. et al. *Exp. Cell Res.* 2001, 271, 344-355). Therefore, inhibition of p38 kinase is also expected to impact tumor growth by interfering with signaling cascades associated with both angiogenesis and malignant cell invasion.

Certain ureas have been described as having activity as serine-threonine kinase and/or as tyrosine kinase inhibitors. In particular, the utility of certain ureas as an active ingredient in pharmaceutical compositions for the treatment of cancer, angiogenesis disorders, inflammatory disorders, has been demonstrated.

For cancer and angiogenesis, see:
Smith et al., *Bioorg. Med Chem. Lett.* 2001, 11, 2775-2778.
Lowinger et al., *Clin. Cancer Res.* 2000, 6(suppl.), 335.
Lyons et al., *Endocr.-Relat. Cancer* 2001, 8, 219-225.
Riedl et al., Book of Abstracts, 92$^{nd}$ AACR Meeting, New Orleans, La., USA, abstract 4956.
Khire et al., Book of Abstracts, 93$^{rd}$ AACR Meeting, San Francisco, Calif., USA, abstract 4211.
Lowinger et al., *Curr. Pharm. Design* 2002, 8, 99-110.
Carter et al., Book of Abstracts, 92$^{nd}$ AACR Meeting, New Orleans, La., USA, abstract 4954.
Vincent et al., Book of Abstracts, 38$^{th}$ ASCO Meeting, Orlando, Fla. USA, abstract 1900.
Hilger et al., Book of Abstracts, 38$^{th}$ ASCO Meeting, Orlando, Fla., USA, abstract 1916.
Moore et al., Book of Abstracts, 38$^{th}$ ASCO Meeting, Orlando, Fla., USA, abstract 1816.
Strumberg et al., Book of Abstracts, 38$^{th}$ ASCO Meeting, Orlando, Fla., USA, abstract 121.

For p38 mediated diseases, including inflammatory disorders, see:
Redman et al., *Bioorg Med. Chem. Lett.* 2001, 11, 9-12.
Dumas et al., *Bioorg Med. Chem. Lett.* 2000, 10, 2047-2050.
Dumas et al., *Bioorg. Med. Chem. Lett.* 2000, 10, 2051-2054.
Ranges et al., Book of Abstracts, 220th ACS National Meeting, Washington, D.C., USA, MEDI 149.
Dumas et al., *Bioorg. Med. Chem. Lett.* 2002, 12, 1559-1562.
Regan et al., *J. Med. Chem.* 2002, 45, 2994-3008.
Pargellis et al., *Nature Struct. Biol.* 2002, 9(4), 268-272.
Madwed J. B., Book of Abstracts, Protein Kinases: Novel Target Identification and
Validation for Therapeutic Development, San Diego, Calif., USA, March 2002.
Pargellis C. et al., *Curr. Opin. Invest. Drugs* 2003, 4, 566-571.
Branger J. et al., *J. Immunol.* 2002, 168, 4070-4077.
Branger J. et al., *Blood* 2003, 101, 4446-4448.

Omega-Carboxyaryl diphenyl ureas are disclosed in WO00/42012, published: Jul. 20, 2000, WO00/41698, published: Jul. 20, 2000, the following published U.S. applications:
US2002-0165394-A1, published Nov. 7, 2002,
US2001-003447-A1, published Oct. 25, 2001,
US2001-0016659-A1, published Aug. 23, 2001,
US2002-013774-A1, published Sep. 26, 2002, and copending U.S. applications:
Ser. No. 09/758,547, filed Jan. 12, 2001,
Ser. No. 09/889,227, filed Jul. 12, 2001,
Ser. No. 09/993,647, filed Nov. 27, 2001,
Ser. No. 10/042,203, filed Jan. 11, 2002 and
Ser. No. 10/071,248, filed Feb. 11, 2002,

DESCRIPTION OF THE INVENTION

It has been discovered that the omega-carboxyaryl diphenyl urea of Formula I below, which has a 2-fluoro-4-(2-(N-methylcarbamoyl)-4-pyridyloxy)phenylene group bound to urea is a potent inhibitor raf kinase, VEGFR kinase, p38 kinase, and PDGFR kinase, which are all molecular targets of interest for the treatment and prevention of osteoporosis, inflammatory disorders, hyper-proliferatrive disorders, and angiogenesis disorders, including cancer.

The present invention provides, e.g.,
(i) a novel compound of Formula (I), salts, prodrugs, and metabolites thereof,
(ii) pharmaceutical compositions containing such compound, and
(iii) use of this compound or compositions for treating diseases and conditions mediated by raf, VEGFR, PDGFR, flt-3, and p38, either as a sole agent or in combination with cytotoxic therapies.

The compound of the Formula I below, salts, prodrugs and metabolites thereof is collectively referred to as the "compounds of the invention". Formula I is as follows:

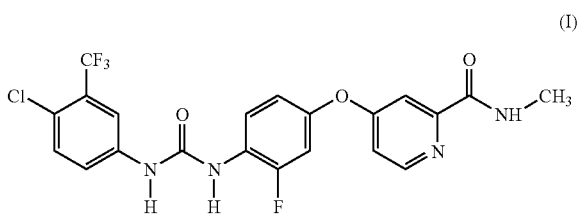 [SMILES: CNC(=O)c1cc(Oc2ccc(NC(=O)Nc3ccc(Cl)c(C(F)(F)F)c3)c(F)c2)ccn1]

(I)

The metabolites of the compound of this invention include oxidized derivatives of Formula I wherein one or more of the urea nitrogens are substituted with a hydroxy group. The metabolites of the compound of this invention also include analogs where the methylamide group of the compound of Formula I is hydroxylated then de-methylated by metabolic degradation. The metabolites of the compound of this invention further include oxidized derivatives where the pyridine nitrogen atom is in the N-oxide form (e.g. carries a hydroxy substituent) leading to those structures referred to in the art as 1-oxo-pyridine and 1-hydroxy-pyridine.

Where the plural form of the word compounds, salts, and the like, is used herein, this is taken to mean also a single compound, salt, or the like.

The use of pharmaceutically acceptable salts of the compounds of Formula I is also within the scope of this invention. The term "pharmaceutically acceptable salt" refers to a relatively non-toxic, inorganic or organic acid addition salt of a compound of the present invention. For example, see S. M. Berge, et al. "Pharmaceutical Salts," *J. Pharm. Sci.* 1977, 66, 1-19.

Representative salts of the compound of this invention include the conventional non-toxic salts, for example, from inorganic or organic acids by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

The salts or prodrugs of the compounds of Formula I may contain one or more asymmetric centers. Asymmetric carbon atoms may be present in the (R) or (S) configuration or (R,S) configuration. Substituents on a ring may also be present in either cis or trans form. It is intended that all such configurations (including enantiomers and diastereomers), are included within the scope of the present invention. Preferred isomers are those with the configuration which produces the more desirable biological activity. Separated, pure or partially purified isomers or racemic mixtures of the compounds of this invention are also included within the scope of the present invention. The purification of said isomers and the separation of said isomeric mixtures can be accomplished by standard techniques known in the art.

The particular process to be utilized in the preparation of the compound used in this embodiment of the invention is described in Example 1. Salt forms of the compound of Formula (I) are described in Examples 2, 3, and 4.

Methods of Use

The present invention provides compounds which are capable of modulating one or more signal transduction pathways involving raf, VEGFR, PDGFR, p38, and/or flt-3 kinases. Raf is an important signaling molecule involved in the regulation of a number of key cellular processes, including cell growth, cell survival and invasion. It is a member of the Ras/raf/MEK/ERK pathway. This pathway is present in most tumor cells. VEGFR, PDGFR, and flt-3 are transmembrane receptor molecules which, when stimulated by an appropriate ligand, trigger the Ras/raf/MEK/ERK cell signaling pathway, leading to a cascade of cellular events. Each of these receptor molecules have tyrosine kinase activity.

The VEGFR receptors are stimulated by vascular endothelial growth factors (VEGF), and are important control points in the regulation of endothelial cell development and function. The PDGF-beta receptor regulates cell proliferation and survival in a number of cell types, including mesenchymal cells. Flt-3 is a receptor for the FL ligand. It is structurally similar to c-kit, and modulates the growth of pluripotent haemopoietic cells, influencing the development of T-cells, B-cells, and dendritic cells.

Any gene or isoform of raf, VEGFR, PDGFR, p38, and/or flt-3 can be modulated in accordance with present invention, including both wild-type and mutant forms. Raf or raf-1 kinase is a family of serine/threonine kinases which comprise at least three family members, a-raf, b-raf, and c-raf or raf-1. See, e.g., Dhillon and Kolch, Arch. *Biochem. Biophys.* 2002, 404, 3-9. C-raf and b-raf are preferred targets for compounds of the present invention. Activating b-raf mutations (e.g., V599E mutant) have been identified in various cancers, including melanoma, and the compounds described herein can be utilized to inhibit their activity.

By the term "modulate", it is meant that the functional activity of the pathway (or a component of it) is changed in comparison to its normal activity in the absence of the compound. This effect includes any quality or degree of modulation, including, increasing, agonizing, augmenting, enhancing, facilitating, stimulating, decreasing, blocking, inhibiting, reducing, diminishing, antagonizing, etc.

The compounds of the present invention can also modulate one or more of the following processes, including, but not limited to, e.g., cell growth (including, e.g., differentiation, cell survival, and/or proliferation), tumor cell growth (including, e.g., differentiation, cell survival, and/or proliferation), tumor regression, endothelial cell growth (including, e.g., differentiation, cell survival, and/or proliferation), angiogenesis (blood vessel growth), lymphangiogenesis (lymphatic vessel growth), and/or hematopoiesis (e.g., T- and B-cell development, dendritic cell development, etc.).

While not wishing to be bound by any theory or mechanism of action, it has been found that compounds of the present invention possess the ability to modulate kinase activity. The methods of the present invention, however, are not limited to any particular mechanism or how the compounds achieve their therapeutic effect. By the term "kinase activity", it is meant a catalytic activity in which a gamma-phosphate from adenosine triphosphate (ATP) is transferred to an amino acid residue (e.g., serine, threonine, or tyrosine) in a protein substrate. A compound can modulate kinase activity, e.g., inhibiting it by directly competing with ATP for the ATP-binding pocket of the kinase, by producing a conformational change in the enzyme's structure that affects its activity (e.g., by disrupting the biologically-active three-dimensional structure), etc.

Kinase activity can be determined routinely using conventional assay methods. Kinase assays typically comprise the kinase enzyme, substrates, buffers, and components of a detection system. A typical kinase assay involves the reaction of a protein kinase with a peptide substrate and an ATP, such as $^{32}$P-ATP, to produce a phosphorylated end-product (for instance, a phosphoprotein when a peptide substrate is used). The resulting end-product can be detected using any suitable method. When radioactive ATP is utilized, a radioactively labeled phosphoprotein can be separated from the unreacted gamma-$^{32}$P-ATP using an affinity membrane or gel electrophoresis, and then visualized on the gel using autoradiography or detected with a scintillation counter. Non-radioactive methods can also be used. Methods can utilize an antibody which recognizes the phosphorylated substrate, e.g., an anti-phosphotyrosine antibody. For instance, kinase enzyme can incubated with a substrate in the presence of ATP and kinase buffer under conditions which are effective for the enzyme to phosphorylate the substrate. The reaction mixture can be separated, e.g., electrophoretically, and then phosphorylation of the substrate can be measured, e.g., by Western blotting using an anti-phosphotyrosine antibody. The antibody can be labeled with a detectable label, e.g., an enzyme, such as HRP, avidin or biotin, chemiluminescent reagents, etc. Other methods can utilize ELISA formats, affinity membrane separation, fluorescence polarization assays, luminescent assays, etc.

An alternative to a radioactive format is time-resolved fluorescence resonance energy transfer (TR-FRET). This method follows the standard kinase reaction, where a substrate, e.g., biotinylated poly(GluTyr), is phosphorylated by a protein kinase in the presence of ATP. The end-product can then detected with a europium chelate phosphospecific antibody (anti-phosphotyrosine or phosphoserine/threonine), and streptavidin-APC, which binds the biotinylated substrate. These two components are brought together spatially upon binding, and energy transfer from the phosphospecific antibody to the acceptor (SA-APC) produces fluorescent readout in the homogeneous format.

The compounds of the present invention can be used to treat and/or prevent any disease or condition mediated by one or more cellular signal transduction pathways involving raf, VEGFR, PDGFR, p38, and/or flt-3 kinases. The term "treating" is used conventionally, e.g., the management or care of a subject for the purpose of combating, alleviating, reducing, relieving, improving the condition of, etc., of a disease or disorder. The compounds can also be described as being used to prevent and/or treat diseases and/or condition mediated by the signaling molecules. The term "mediated" indicates, e.g., that the signaling molecule is part of the pathway which is aberrant or disturbed in the disease and/or condition.

Diseases and conditions that can be treated include any of those mentioned above and below, as well as:

Raf associated diseases include, e.g., cell-proliferation disorders, cancer, tumors, etc.;

VEGFR-2 associated diseases include, e.g., cancer, tumor growth, inflammatory disease, rheumatoid arthritis, retinopathy, psoriasis, glomerulonephritis, asthma, chronic bronchitis, atherosclerosis, transplant rejection, conditions involving angiogenesis, etc.;

VEGFR-3 associated diseases include, e.g., cancer, corneal disease, inflamed cornea (e.g., Hamrah, *Am. J. Path.* 2003, 163, 57-68), corneal transplantation (Cursiefen et al., *Cornea* 2003, 22, 273-81), lymphatic hyperplasia, conditions involving lymphangiogenesis, etc.;

PDGFR-beta associated diseases include, e.g., diseases or conditions characterized by cell proliferation, cell matrix production, cell movement, and/or extracellular matrix production. Specific examples, include, e.g., tumors, malignancies, cancer, metastasis, chronic myeloid leukemia, inflammation, renal disease, diabetic nephropathy, mesangial proliferative glomerulonephritis, fibrotic conditions, atherosclerosis, restenosis, hypertension-related arteriosclerosis, venous bypass graft arteriosclerosis, scleroderma, interstitial pulmonary diseases, synovial disorders, arthritis, leukemias, lymphomas, etc;

Flt-3 associated diseases include, e.g., immune-related disorders, blood cell disorders, conditions involving hematopoietic cell development (e.g., T-cells, B-cells, dendritic cells, cancer, anemia, HIV, acquired immune deficiency syndrome, etc.

p38 associated diseases include inflammatory disorders, immunomodulatory disorders, and other disorders that have been linked to abnormal cytokine production, especially TNF-alpha, or abnormal MMP activity. These disorders include, but are not limited to, rheumatoid arthritis, COPD, osteoporosis, Crohn's disease and psoriasis.

In addition, compounds of the present invention can be used to treat conditions and disorders disclosed in U.S. Pat. No. 6,316,479, e.g., glomerular sclerosis, interstitial nephritis, interstitial pulmonary fibrosis, atherosclerosis, wound scarring and scleroderma.

The compounds of this invention also have a broad therapeutic activity to treat or prevent the progression of a broad array of diseases, such as inflammatory conditions, coronary restenosis, tumor-associated angiogenesis, atherosclerosis, autoimmune diseases, inflammation, certain kidney diseases associated with proliferation of glomerular or mesangial cells, and ocular diseases associated with retinal vessel proliferation. psoriasis, hepatic cirrhosis, diabetes, atherosclerosis, restenosis, vascular graft restenosis, in-stent stenosis, angiogenesis, ocurlar diseases, pulmonary fibrosis, obliterative bronchiolitis, glomerular nephritis, rheumatoid arthritis.

The present invention also provides for treating, preventing, modulating, etc., one or more of the following conditions in humans and/or other mammals: retinopathy, including diabetic retinopathy, ischemic retinal-vein occlusion, retinopathy of prematurity and age related macular degeneration; rheumatoid arthritis, psoriasis, or bullous disorder associated with subepidermal blister formation, including bullous pemphigoid, erythema multiforme, or dermatitis herpetiformis, rheumatic fever, bone resorption, postmenopausal osteoporosis, sepsis, gram negative sepsis, septic shock, endotoxic shock, toxic shock syndrome, systemic inflammatory response syndrome, inflammatory bowel disease (Crohn's disease and ulcerative colitis), Jarisch-Herxheimer reaction, asthma, adult respiratory distress syndrome, acute pulmonary fibrotic disease, pulmonary sarcoidosis, allergic respiratory disease, silicosis, coal worker's pneumoconiosis, alveolar injury, hepatic failure, liver disease during acute inflammation, severe alcoholic hepatitis, malaria (Plasmodium falciparum malaria and cerebral malaria), non-insulin-dependent diabetes mellitus (NIDDM), congestive heart failure, damage following heart disease, atherosclerosis, Alzheimer's disease, acute encephalitis, brain injury, multiple sclerosis (demyelation and oligiodendrocyte loss in multiple sclerosis), advanced cancer, lymphoid malignancy, pancreatitis, impaired wound healing in infection, inflammation and cancer, myelodysplastic syndromes, systemic lupus erythematosus, biliary cirrhosis, bowel necrosis, radiation injury/toxicity following administration of monoclonal antibodies, host-versus-graft reaction (ischemia reperfusion injury and allograft rejections of kidney, liver, heart, and skin), lung allograft rejection (obliterative bronchitis), or complications due to total hip replacement, ad an infectious disease selected from tuberculosis, *Helicobacter pylori* infection during peptic ulcer disease, Chaga's disease resulting from *Trypanosoma cruzi* infection, effects of Shiga-like toxin resulting from *E. coli* infection, effects of enterotoxin A resulting from *Staphylococcus* infection, meningococcal infection, and infections from *Borrelia Burgdorferi, Treponema pallidum*, cytomegalovirus, influenza virus, Theiler's encephalomyelitis virus, and the human immunodeficiency virus (HIV), papilloma, blastoglioma, Kaposi's sarcoma, melanoma, lung cancer, ovarian cancer, prostate cancer, squamous cell carcinoma, astrocytoma, head cancer, neck cancer, bladder cancer, breast cancer, colorectal cancer, thyroid cancer, pancreatic cancer, gastric cancer, hepatocellular carcinoma, leukemia, lymphoma, Hodgkin's disease, Burkitt's disease, arthritis, rheumatoid arthritis, diabetic retinopathy, angiogenesis, restenosis, in-stent restenosis, vascular graft restenosis, pulmonary fibrosis, hepatic cirrhosis, atherosclerosis, glomerulonophritis, diabetic nephropathy, thrombic micoangiopathy syndromes, transplant rejection, psoriasis, diabetes, wound healing, inflammation, and neurodegenerative diseases. hyperimmune disorders, hemangioma, myocardial angiogenesis, coronary and cerebral collateral vascularization, ischemia, corneal disease, rubeosis, neovascular glaucoma, macular degeneration retinopathy of prematurity, wound healing, ulcer Helicobacter related diseases, fractures, endometriosis, a diabetic condition, cat scratch fever, thyroid hyperplasia, asthma or edema following burns, trauma, chronic lung disease, stroke, polyps, cysts, synovitis, chronic and allergic inflammation, ovarian hyperstimulation syndrome, pulmonary and cerebral edema, keloid, fibrosis, cirrhosis, carpal tunnel syndrome, adult respiratory distress syndrome, ascites, an ocular condition, a cardiovascular condition, Crow-Fukase (POEMS) disease, Crohn's disease, glomerulonophritis, osteoarthritis, multiple sclerosis, graft rejection, Lyme disease, sepsis, von Hippel Lindau disease, pemphigoid, Paget's disease, polycystic kidney disease, sarcoidosis, throiditis, hyperviscosity syndrome, Osler-Weber-Rendu disease, chronic occlusive pulmonary disease, radiation, hypoxia, preeclampsia, menometrorrhagia, endometriosis, infection by Herpes simplex, ischemic retinopathy, corneal angiogenesis, Herpes Zoster, human immunodeficiency virus, parapoxvirus, protozoa, toxoplasmosis, and tumor-associated effusions and edema.

The compounds of this invention can possess more than one of the mentioned activities, and therefore can target a plurality of signal transduction pathways. Thus, these compounds can achieve therapeutic and prophylactic effects which normally are only obtained when using a combination of different compounds. For instance, the ability to inhibit both new vessel formation (e.g., associated with VEGFR-2 and VEGFR-3 function) (e.g., blood and/or lymph) and cell-proliferation (e.g., associated with raf and PDGFR-beta function) using a single compound is especially beneficial in the treatment of cancer, and other cell-proliferation disorders that are facilitated by neo-vascularization. Thus, the present invention relates specifically to compounds which possess at least anti-cell proliferation and anti-angiogenic (i.e., inhibits angiogenesis) activity. Any disorder or condition that would benefit from inhibiting vessel growth and cell proliferation can be treated in accordance with the present invention. Using a single compound is also advantageous because its range of activities can be more precisely defined.

As indicated above, the present invention relates to methods of treating and/or preventing diseases and conditions; and/or modulating one or more of the pathways, polypeptides, genes, diseases, conditions, etc., associated with raf, VEGFR, PDGFR, p38, and/or flt-3. These methods generally involve administering effective amounts of compounds of the present invention, where an effective amount is the quantity of the compound which is useful to achieve the desired result. Compounds can be administered in any effective form by any effective route, as discussed in more detail below.

Methods include modulating tumor cell proliferation, including inhibiting cell proliferation. The latter indicates that the growth and/or differentiation of tumor cells is reduced, decreased, diminished, slowed, etc. The term "proliferation" includes any process which relates to cell growth and division, and includes differentiation and apoptosis. As discussed above, raf kinases play a key role in the activation of the cytoplasmic signaling cascade involved in cell proliferation, differentiation, and apoptosis. For example, studies have found that inhibiting c-raf by anti-sense oligonucleotides can block cell proliferation (see above). Any amount of inhibition is considered therapeutic.

Included in the methods of the present invention is a method for using the compound described above (Compound of Formula I), including salts, prodrugs, metabolites (oxidized derivatives) and compositions thereof, to treat mammalian hyper-proliferative disorders comprising administering to a mammal, including a human in need thereof, an amount of a compound of this invention, pharmaceutically acceptable salt, prodrug, metabolite (oxidized derivative), and composition thereof, which is effective to treat the disorder. Hyperproliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Any tumor or cancer can be treated, including, but not limited to, cancers having one or more mutations in raf, ras, and/or flt-3, as well as any upstream or downstream member of the signaling pathways of which they are a part. As discussed earlier, a cancer can be treated with a compound of the present invention irrespective of the mechanism which is responsible for it. Cancers of any organ can be treated, including cancers of, but are not limited to, e.g., colon, pancreas, breast, prostate, bone, liver, kidney, lung, testes, skin, pancreas, stomach, colorectal cancer, renal cell carcinoma, hepatocellular carcinoma, melanoma, etc.

Examples of breast cancer include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumor.

Tumors of the male reproductive organs include, but are not limited to, prostate and testicular cancer. Tumors of the female reproductive organs include, but are not limited to, endometrial, cervical, ovarian, vaginal, and vulvar cancer, as well as sarcoma of the uterus.

Tumors of the digestive tract include, but are not limited to, anal, colon, colorectal, esophageal, gallbladder, gastric, pancreatic, rectal, small-intestine, and salivary gland cancers.

Tumors of the urinary tract include, but are not limited to, bladder, penile, kidney, renal pelvis, ureter, and urethral cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, and/or oropharyngeal cancers, and lip and oral cavity cancer.

Lymphomas include, but are not limited to, AIDS-related lymphoma, non-Hodgkin's lymphoma, cutaneous T-cell lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

In addition to inhibiting the proliferation of tumor cells, compounds of the present invention can also cause tumor regression, e.g., a decrease in the size of a tumor, or in the extent of cancer in the body.

The present invention also relates to methods of modulating angiogenesis and/or lymphangiogenesis in a system comprising cells, comprising administering to the system an effective amount of a compound described herein. A system comprising cells can be an in vivo system, such as a tumor in a patient, isolated organs, tissues, or cells, in vitro assays systems (CAM, BCE, etc), animal models (e.g., in vivo, subcutaneous, cancer models), hosts in need of treatment (e.g., hosts suffering from diseases having angiogenic and/or lymphangiogenic component, such as cancer), etc.

Inappropriate and ectopic expression of angiogenesis can be deleterious to an organism. A number of pathological conditions are associated with the growth of extraneous blood vessels. These include, e.g., diabetic retinopathy, neovascular glaucoma, psoriasis, retrolental fibroplasias, angiofibroma, inflammation, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer.

Useful systems for measuring angiogenesis and/or lymphangiogenesis, and inhibition thereof, include, e.g., neovascularization of tumor explants (e.g., U.S. Pat. Nos. 5,192,744; 6,024,688), chicken chorioallantoic membrane (CAM) assay (e.g., Taylor and Folkman, Nature 1982, 297, 307-312; Eliceiri et al., J. Cell Biol. 1998, 140, 1255-1263), bovine capillary endothelial (BCE) cell assay (e.g., U.S. Pat. No. 6,024,688; Polverini, P. J. et al., Methods Enzymol. 1991, 198, 440-450), migration assays, and HUVEC (human umbilical cord vascular endothelial cell) growth inhibition assay (e.g., U.S. Pat. No. 6,060,449), and use of the rabbit ear model (e.g., Szuba et al., FASEB J. 2002, 16(14), 1985-7).

Modulation of angiogenesis can be determined by any other method. For example, the degree of tissue vascularity is typically determined by assessing the number and density of vessels present in a given sample. For example, microvessel density (MVD) can be estimated by counting the number of endothelial clusters in a high-power microscopic field, or detecting a marker specific for microvascular endothelium or other markers of growing or established blood vessels, such as CD31 (also known as platelet-endothelial cell adhesion molecule or PECAM). A CD31 antibody can be employed in conventional immunohistological methods to immunostain tissue sections as described by, e.g., U.S. Pat. No. 6,017,949; Dellas et al., Gyn. Oncol. 1997, 67, 27-33; and others. Other markers for angiogenesis, include, e.g., Vezf1 (e.g., Xiang et al., Dev. Bio. 1999, 206, 123-141), angiopoietin, Tie-1, and Tie-2 (e.g., Sato et al., Nature 1995, 376, 70-74).

Additionally, the present invention relates to methods of screening patients to determine their sensitivity to compounds of the present invention. For example, the invention relates to methods of determining whether a condition can be modulated by a compound disclosed herein, comprising measuring the expression or activity of raf, VEGFR-2, VEGFR-3, PDGFR-beta, p38, and/or flt-3 in a sample comprising cells or a cell extract, wherein said sample has been obtained from a cell or subject having said condition. When the results of the determination indicate that one or more of the mentioned genes (and/or polypeptides which they encode) differ from the normal state, this identifies the condition as being treatable with a compound of the present invention, i.e., whereby said disorder or condition can be modulated by the compound when said expression or activity is increased in said condition as compared to a normal control. The method can further comprise a step of comparing the expression in a sample with a normal control, or expression in a sample obtained from normal or unaffected tissue. Comparing can be done manually, against a standard, in an electronic form (e.g., against a database), etc. The normal control can be a standard sample that is provided with the assay; it can be obtained from adjacent, but unaffected, tissue from the same patient; or, it can be pre-determined values, etc. Gene expression, protein expression (e.g., abundance in a cell), protein activity (e.g., kinase activity), etc., can be determined.

For instance, a biopsy from a cancer patient can be assayed for the presence, quantity, and/or activity of raf, VEGFR-2, VEGFR-3, PDGFR-beta, p38, and/or flt-3. Increased expression or activity of one or more of these can indicate that the cancer can be targeted for treatment by a compound of the present invention. For example, as described in the examples below, raf activity can be monitored by its ability to initiate the cascade leading to ERK phosphorylation (i.e., raf/MEK/ERK), resulting in phospho-ERK. Increased phospho-ERK levels in a cancer specimen shows that its raf activity is elevated, suggesting the use of compounds of the present invention to treat it.

Measuring expression includes determining or detecting the amount of the polypeptide present in a cell or shed by it, as well as measuring the underlying mRNA, where the quantity of mRNA present is considered to reflect the quantity of polypeptide manufactured by the cell. Furthermore, the genes for raf, VEGFR-2, VEGFR-3, PDGFR-beta, p38, and/or Flt-3 can be analyzed to determine whether there is a gene defect responsible for aberrant expression or polypeptide activity.

Polypeptide detection can be carried out by any available method, e.g., by Western blots, ELISA, dot blot, immunoprecipitation, RIA, immunohistochemistry, etc. For instance, a tissue section can be prepared and labeled with a specific antibody (indirect or direct and visualized with a microscope. Amount of a polypeptide can be quantitated without visualization, e.g., by preparing a lysate of a sample of interest, and then determining by ELISA or Western the amount of polypeptide per quantity of tissue. Antibodies and other specific binding agents can be used. There is no limitation on how detection is performed.

Assays can be utilized which permit quantification and/or presence/absence detection of a target nucleic acid (e.g., genes, mRNA, etc., for raf, VEGFR, PDGFR, p38, and/or flt-3) in a sample. Assays can be performed at the single-cell level, or in a sample comprising many cells, where the assay is "averaging" expression over the entire collection of cells and tissue present in the sample. Any suitable assay format can be used, including, but not limited to, e.g., Southern blot analysis, Northern blot analysis, polymerase chain reaction ("PCR") (e.g., Saiki et al., *Science* 1988, 241, 53; U.S. Pat. Nos. 4,683,195, 4,683,202, and 6,040,166; PCR Protocols: A Guide to Methods and Applications, Innis et al., eds., Academic Press, New York, 1990), reverse transcriptase polymerase chain reaction ("RT-PCR"), anchored PCR, rapid amplification of cDNA ends ("RACE") (e.g., Schaefer in Gene Cloning and Analysis: Current Innovations, Pages 99-115, 1997), ligase chain reaction ("LCR") (EP 320 308), one-sided PCR (Ohara et al., *Proc. Natl. Acad Sci.* 1989, 86, 5673-5677), indexing methods (e.g., U.S. Pat. No. 5,508, 169), in situ hybridization, differential display (e.g., Liang et al., *Nucl. Acid. Res.* 1993, 21, 3269 3275; U.S. Pat. Nos. 5,262,311, 5,599,672 and 5,965,409; WO97/18454; Prashar and Weissman, Proc. Natl. Acad. Sci., 93:659-663, and U.S. Pat. Nos. 6,010,850 and 5,712,126; Welsh et al., Nucleic Acid Res., 20:4965-4970, 1992, and U.S. Pat. No. 5,487,985) and other RNA fingerprinting techniques, nucleic acid sequence based amplification ("NASBA") and other transcription based amplification systems (e.g., U.S. Pat. Nos. 5,409,818 and 5,554,527; WO 88/10315), polynucleotide arrays (e.g., U.S. Pat. Nos. 5,143,854, 5,424,186; 5,700,637, 5,874,219, and 6,054,270; PCT WO 92/10092; PCT WO 90/15070), Qbeta Replicase (PCT/US87/00880), Strand Displacement Amplification ("SDA"), Repair Chain Reaction ("RCR"), nuclease protection assays, subtraction-based methods, Rapid-Scan, etc. Additional useful methods include, but are not limited to, e.g., template-based amplification methods, competitive PCR (e.g., U.S. Pat. No. 5,747,251), redox-based assays (e.g., U.S. Pat. No. 5,871,918), Taqman-based assays (e.g., Holland et al., *Proc. Natl. Acad, Sci.* 1991, 88, 7276-7280; U.S. Pat. Nos. 5,210,015 and 5,994,063), real-time fluorescence-based monitoring (e.g., U.S. Pat. No. 5,928, 907), molecular energy transfer labels (e.g., U.S. Pat. Nos. 5,348,853, 5,532,129, 5,565,322, 6,030,787, and 6,117,635; Tyagi and Kramer, Nature Biotech., 14:303-309, 1996). Any method suitable for single cell analysis of gene or protein expression can be used, including in situ hybridization, immunocytochemistry, MACS, FACS, flow cytometry, etc. For single cell assays, expression products can be measured using antibodies, PCR, or other types of nucleic acid amplification (e.g., Brady et al., *Methods Mol. & Cell. Biol.* 1990, 2, 17-25; Eberwine et al., *Proc. Natl. Acad. Sci.* 1992, 89, 3010-3014; U.S. Pat. No. 5,723,290). These and other methods can be carried out conventionally, e.g., as described in the mentioned publications.

Activity of raf, VEGFR-2, VEGFR-3, PDGFR-beta, p38, and/or flt-3 can be assessed routinely, e.g., as described in the examples below, or using standard assays for kinase activity.

The present invention also provides methods of assessing the efficacy of a compound of the present invention in treating a disorder, comprising one or more of the following steps in any effective order, e.g., administering an amount of a compound, measuring the expression or activity of raf, VEGFR-2, VEGFR-3, PDGFR-beta, p38, and/or flt-3 (see above), determining the effect of said compound on said expression or activity. For instance, biopsy samples can be removed from patients who have been treated with a compound of the present invention, and then assayed for the presence and/or activity of the mentioned signaling molecules. Similarly, as discussed above, decreases in the levels of phospho-ERK in the cancer tissue (e.g., compared to normal tissue or before treatment) indicate that the compound is exerting in vivo efficacy and a therapeutic effect. The method can be used to determine appropriate dosages and dosing regimens, e.g., how much compound to administer and at what frequency to administer it. By monitoring its effect on the signaling molecules in the tissue, the clinician can determine the appropriate treatment protocol and whether it is achieving the desired effect, e.g., on modulating or inhibiting the signal transduction pathway.

Compounds of the present invention also can be used as markers to determine the presence and quantity of raf, VEGFR-2, VEGFR-3, PDGFR-beta, p38, and/or flt-3, in a sample comprising a biological material. This comprises one or more of the following steps in any effective order: (i) contacting said sample comprising a biological material with a compound of the present invention, and (ii) determining whether said compound binds to said material. The compound can be labeled, or it can be used as a competitor to a labeled compound, such as labeled-ATP.

The invention also provides methods for treating, preventing, modulating, etc., diseases and conditions in mammals comprising administering a compound of this invention with another modulator of the signal transduction pathway comprising, but not limited to raf, VEGFR, PDGFR, p38, and/or flt-3. These can be present in the same composition or in separate formulations or dosage units. Administration can be the same or different routes, and can be simultaneous or sequential.

The following publications relate to VEGFR-3 modulation and are incorporated herein for their description of disease states mediated by VEGFR-3 and assays to determine such activity.

| WO95/33772 | Alitalo, et. al. |
|---|---|
| WO95/33050 | Charnock-Jones, et. al.. |
| WO96/39421 | Hu, et. al. |
| WO98/33917 | Alitalo, et. al. |
| WO02/057299 | Alitalo, et. al. |

-continued

| | |
|---|---|
| WO02/060950 | Alitalo, et. al. |
| WO02/081520 | Boesen, et. al. |

The following publications relate to VEGFR-2 modulation and are incorporated herein for their description of disease states mediated by VEGFR-2 and assays to determine such activity.

| | |
|---|---|
| EP0882799 | Hanai, et. al. |
| EP1167384 | Ferraram, et, al. |
| EP1086705 | Sato, et. al. |
| EP11300032 | Tesar, et. al. |
| EP1166798 | Haberey, et. al. |
| EP1166799 | Haberey, et. al. |
| EP1170017 | Maini, et. al. |
| EP1203827 | Smith |
| WO02/083850 | Rosen, et. al. |

The following publications relate to flt-3 modulation and are incorporated herein for their description of disease states mediated by flt-3 and assays to determine such activity.

| | |
|---|---|
| 2002/0034517 | Brasel, et. al. |
| 2002/0107365 | Lyman, et. al. |
| 2002/0111475 | Graddis, et. al. |
| EP0627487 | Beckermann, et. al. |
| WO9846750 | Bauer, et. al. |
| WO9818923 | McWherter, et. al. |
| WO9428391 | Beckermann, et al. |
| WO9426891 | Birnbaum, et. al. |

The following patents and publication relate to PDGF/PDGFR modulation and are incorporated herein for their description of the disease states mediated by PDGFR-beta and assays to determine such activity.

| | |
|---|---|
| 5,094,941 | Hart, et. al. |
| 5,371,205 | Kelly, et. al. |
| 5,418,135 | Pang |
| 5,444,151 | Vassbotn, et. al. |
| 5,468,468 | LaRochelle, et. al. |
| 5,567,584 | Sledziewski, et. al. |
| 5,618,678 | Kelly, et. al. |
| 5,620,687 | Hart, et. al. |
| 5,648,076 | Ross, et. al. |
| 5,668,264 | Janjic, et. al. |
| 5,686,572 | Wolf, et. al. |
| 5,817,310 | Ramakrishnan, et. al. |
| 5,833,986 | LaRochelle, et. al. |
| 5,863,739 | LaRochelle, et. al. |
| 5,872,218 | Wolf, et. al. |
| 5,882,644 | Chang, et. al. |
| 5,891,652 | Wolf, et. al. |
| 5,976,534 | Hart, et. al. |
| 5,990,141 | Hirth, et. al. |
| 6,022,854 | Shuman |
| 6,043,211 | Williams, et. al. |
| 6,110,737 | Escobedo, et. al. |
| 6,207,816B1 | Gold, et. al. |
| 6,228,600B1 | Matsui, et. al. |
| 6,229,002B1 | Janjic, et. al. |
| 6,316,603B1 | McTigue, et. al. |
| 6,372,438B1 | Williams, et. al. |
| 6,403,769B1 | La Rochelle, et. al. |
| 6,440,445B1 | Nowak, et. al. |
| 6,475,782B1 | Escobedo, et. al. |
| WO02/083849 | Rosen, et. al. |

-continued

| | |
|---|---|
| WO02/083704 | Rosen, et. al. |
| WO02/081520 | Boesen, et. al. |
| WO02/079498 | Thomas, et. al. |
| WO02/070008 | Rockwell, et. al. |
| WO09959636 | Sato, et. al. |
| WO09946364 | Cao, et. al. |
| WO09940118 | Hanai, et. al. |
| WO9931238 | Yabana, et. al. |
| WO9929861 | Klagsbrun, et. al. |
| WO9858053 | Kendall, et. al. |
| WO9851344 | Maini, et. al. |
| WO9833917 | Alitalo, et. al. |
| WO9831794 | Matsumoto, et. al. |
| WO9816551 | Ferrara, et. al. |
| WO9813071 | Kendall, et al. |
| WO9811223 | Martiny-Baron, et. al. |
| WO9744453 | Chen, et. al. |
| WO9723510 | Plouet, et. al. |
| WO9715662 | Stinchcomb, et. al. |
| WO9708313 | Ferrara, et. al. |
| WO9639515 | Cao, et. al. |
| WO9623065 | Smith, et. al. |
| WO9606641 | Fleurbaaij, et. al. |
| WO9524473 | Cao, et. al. |
| WO9822316 | Kyowa |
| WO9521868 | Rockwell, et. al. |
| WO02/060489 | Xia, et. al. |
| PDGFR-beta | |
| EP0869177 | Matsui, et. al. |
| WO09010013 | Matsui, et. al. |
| WO9737029 | Matsui, et. al. |
| PDGFR-alpha | |
| EP1000617 | Lammers, et. al. |
| EP0869177 | Matsui, et. al. |
| EP0811685 | Escobedo, et. al. |

Pharmaceutical Compositions Based on the Compounds of the Present Invention

This invention also relates to pharmaceutical compositions containing a compound of the present invention and pharmaceutically acceptable salts thereof. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions which are comprised of a pharmaceutically acceptable carrier and a pharmaceutically effective amount of a compound, or salt thereof, of the present invention. The term "pharmaceutically acceptable carrier" is meant as any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is that amount which produces a result or exerts an influence on the particular condition being treated. The compound of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compound can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such material is, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations which are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients which can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC\text{-}CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono-or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)
plasticizers (examples include but are not limited to diethyl phthalate and glycerol);
solvents (examples include but are not limited to ethanol, corn oil, cottonseed oil, glycerol, isopropanol, mineral oil, oleic acid, peanut oil, purified water, water for injection, sterile water for injection and sterile water for irrigation);
stiffening agents (examples include but are not limited to cetyl alcohol, cetyl esters wax, microcrystalline wax, paraffin, stearyl alcohol, white wax and yellow wax);
suppository bases (examples include but are not limited to cocoa butter and polyethylene glycols (mixtures));
surfactants (examples include but are not limited to benzalkonium chloride, nonoxynol 10, oxtoxynol 9, polysorbate 80, sodium lauryl sulfate and sorbitan mono-palmitate);
suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);
sweetening agents (examples include but are not limited to aspartame, dextrose, glycerol, mannitol, propylene glycol, saccharin sodium, sorbitol and sucrose);
tablet anti-adherents (examples include but are not limited to magnesium stearate and talc);
tablet binders (examples include but are not limited to acacia, alginic acid, carboxymethylcellulose sodium, compressible sugar, ethylcellulose, gelatin, liquid glucose, methylcellulose, and pregelatinized starch);
tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);
tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);
tablet direct compression excipients (examples include but are not limited to dibasic calcium phosphate);
tablet disintegrants (examples include but are not limited to alginic acid, carboxymethylcellulose calcium, microcrystalline cellulose, polacrillin potassium, sodium alginate, sodium starch glycollate and starch);
tablet glidants (examples include but are not limited to colloidal silica, corn starch and talc);
tablet lubricants (examples include but are not limited to calcium stearate, magnesium stearate, mineral oil, stearic acid and zinc stearate);
tablet/capsule opaquants (examples include but are not limited to titanium dioxide);
tablet polishing agents (examples include but are not limited to carnauba wax and white wax);
thickening agents (examples include but are not limited to beeswax, cetyl alcohol and paraffin);
tonicity agents (examples include but are not limited to dextrose and sodium chloride);
viscosity increasing agents (examples include but are not limited to alginic acid, bentonite, carbomers, carboxymethylcellulose sodium, methylcellulose, sodium alginate and tragacanth); and
wetting agents (examples include but are not limited to heptadecaethylene oxycetanol, lecithin, sorbitol monooleate, polyoxyethylene sorbitol monooleate, and polyoxyethylene stearate).

Pharmaceutical compositions according to the present invention can be illustrated as follows:

Sterile IV Solution: a 5 mg/mL solution of the desired compound of this invention is made using sterile, injectable water, and the pH is adjusted if necessary. The solution is diluted for administration to 1-2 mg/mL with sterile 5% dextrose and is administered as an IV infusion over 60 minutes.

Lyophilized powder for IV administration: A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:
  50 mg/mL of the desired, water-insoluble compound of this invention
  5 mg/mL sodium carboxymethylcellulose
  4 mg/mL Tween 80
  9 mg/mL sodium chloride
  9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Dosage of the Pharmaceutical Compositions of the Present Invention

Based upon standard laboratory techniques known to evaluate compounds useful for the treatment of any of the aforementioned disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered can range from about 0.001 mg/kg to about 200 mg/kg, and preferably from about 0.1 mg/kg to about 50 mg/kg body weight per day. A unit dosage may preferably contain from about 5 mg to about 4000 mg of active ingredient, and can be administered one or more times per day. The daily dosage for oral administration will preferably be from 0.1 to 50 mg/kg of total body weight. The daily dosage for administration by injection, including intravenous, intramuscular, subcutaneous and parenteral injections, and use of infusion techniques will preferably be from 0.1 to 10 mg/kg of total body weight. The daily rectal dosage regimen will preferably be from 0.1 to 50 mg/kg of total body weight. The daily vaginal dosage regimen will preferably be from 0.1 to 50 mg/kg of total body weight. The daily topical dosage regimen will preferably be from 0.1 to 10 mg/kg administered between one to four times daily. The transdermal concentration will preferably be that required to maintain a daily dose of from 0.1 to 10 mg/kg. The daily inhalation dosage regimen will preferably be from 0.1 to 10 mg/kg of total body weight. Other dosages and amounts can be selected routinely.

The specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination of the Compounds and Compositions of the Present Invention with Additional Active Ingredients Compounds of this invention can be administered as the sole pharmaceutical agent or in combination with one or more other pharmaceutical agents where the combination causes no unacceptable adverse effects. This may be of particular relevance for the treatment of hyper-proliferative diseases such as cancer. In this instance, the compound of this invention can be combined with known cytotoxic agents, signal transduction inhibitors, or with other anti-cancer agents, as well as with admixtures and combinations thereof.

In one embodiment, the compounds of the present invention can be combined with cytotoxic anti-cancer agents. Examples of such agents can be found in the 11$^{th}$ Edition of the *Merck Index* (1996). These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other cytotoxic drugs suitable for use with the compounds of the invention include, but are not limited to, those compounds acknowledged to be used in the treatment of neoplastic diseases in *Goodman and Gilman's The Pharmacological Basis of Therapeutics* (Ninth Edition, 1996, McGraw-Hill). These agents include, by no way of limitation, aminoglutethimide, L-asparaginase, azathioprine, 5-azacytidine cladribine, busulfan, diethylstilbestrol, 2', 2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other cytotoxic anti-cancer agents suitable for use in combination with the compounds of the invention also include newly discovered cytotoxic principles such as oxaliplatin, gemcitabine, capecitabine, epothilone and its natural or synthetic derivatives, temozolomide (Quinn et al., *J. Clin. Oncology* 2003, 21(4), 646-651), tositumomab (Bexxar), trabedectin (Vidal et al., *Proceedings of the American Society for Clinical Oncology* 2004, 23, abstract 3181), and the inhibitors of the kinesin spindle protein Eg5 (Wood et al., *Curr. Opin. Pharmacol.* 2001, 1, 370-377).

In another embodiment, the compounds of the present invention can be combined with other signal transduction inhibitors. Of particular interest are signal transduction inhibitors which target the EGFR family, such as EGFR, HER-2, and HER-4 (Raymond et al., *Drugs* 2000, 60 (Suppl.1), 15-23; Harari et al., *Oncogene* 2000, 19 (53), 6102-6114), and their respective ligands. Examples of such agents include, by no way of limitation, antibody therapies such as Herceptin (trastuzumab), Erbitux (cetuximab), and pertuzumab. Examples of such therapies also include, by no way of limitation, small-molecule kinase inhibitors such as ZD-1839/Iressa (Baselga et al., *Drugs* 2000, 60 (Suppl. 1), 33-40), OSI-774/Tarceva (Pollack et al. *J. Pharm. Exp. Ther.* 1999, 291(2), 739-748), CI-1033 (Bridges, *Curr. Med. Chem.* 1999, 6, 825-843), GW-2016 (Lackey et al., 92$^{nd}$ *AACR Meeting, New Orleans, Mar.* 24-28, 2001, abstract 4582), CP-724, 714 (Jani et al., *Proceedings of the American Society for Clinical Oncology* 2004, 23, abstract 3122), HKI-272 (Rabindran et al., *Cancer Res.* 2004, 64, 3958-3965), and EKB-569 (Greenberger et al., 11$^{th}$ *NCI-EORTC-AACR Symposium on New Drugs in Cancer Therapy, Amsterdam, November* 7-10, 2000, abstract 388).

In another embodiment, the compounds of the present invention can be combined with other signal transduction inhibitors targeting receptor kinases of the split-kinase domain families (VEGFR, FGFR, PDGFR, flt-3, c-kit, c-fms, and the like), and their respective ligands. These agents include, by no way of limitation, antibodies such as Avastin (bevacizumab). These agents also include, by no way of limitation, small-molecule inhibitors such as STI-571/Gleevec (Zvelebil, *Curr. Opin. Oncol., Endocr. Metab. Invest. Drugs* 2000, 2(1), 74-82), PTK-787 (Wood et al., *Cancer Res.* 2000, 60(8), 2178-2189), SU-11248 (Demetri et al., *Proceedings of the American Society for Clinical Oncology* 2004, 23, abstract 3001), ZD-6474 (Hennequin et al., 92$^{nd}$ *AACR Meeting, New Orleans, Mar.* 24-28, 2001, abstract 3152), AG-13736 (Herbst et al., *Clin. Cancer Res.* 2003, 9, 16 (suppl 1), abstract C253), KRN-951 (Taguchi et al., 95$^{th}$ *AACR Meeting, Orlando, Fla.*, 2004, abstract 2575), CP-547,632 (Beebe et al., *Cancer Res.* 2003, 63, 7301-7309), CP-673,451

(Roberts et al., *Proceedings of the American Association of Cancer Research* 2004, 45, abstract 3989), CHIR-258 (Lee et al., *Proceedings of the American Association of Cancer Research* 2004, 45, abstract 2130), MLN-518 (Shen et al., *Blood* 2003, 102, 11, abstract 476), and AZD-2171 (Hennequin et al., *Proceedings of the American Association of Cancer Research* 2004, 45, abstract 4539).

In another embodiment, the compounds of the present invention can be combined with inhibitors of the Raf/MEK/ERK transduction pathway (Avruch et al., *Recent Prog. Horm. Res.* 2001, 56, 127-155), or the PKB (akt) pathway (Lawlor et al., *J. Cell Sci.* 2001, 114, 2903-2910). These include, by no way of limitation, PD-325901 (Sebolt-Leopold et al., *Proceedings of the American Association of Cancer Research* 2004, 45, abstract 4003), and ARRY-142886 (Wallace et al., *Proceedings of the American Association of Cancer Research* 2004, 45, abstract 3891).

In another embodiment, the compounds of the present invention can be combined with inhibitors of histone deacetylase. Examples of such agents include, by no way of limitation, suberoylanilide hydroxamic acid (SAHA), LAQ-824 (Ottmann et al., *Proceedings of the American Society for Clinical Oncology* 2004, 23, abstract 3024), LBH-589 (Beck et al., *Proceedings of the American Society for Clinical Oncology* 2004, 23, abstract 3025), MS-275 (Ryan et al., *Proceedings of the American Association of Cancer Research* 2004, 45, abstract 2452), and FR-901228 (Piekarz et al., *Proceedings of the American Society for Clinical Oncology* 2004, 23, abstract 3028).

In another embodiment, the compounds of the present invention can be combined with other anti-cancer agents such as proteasome inhibitors, and m-TOR inhibitors. These include, by no way of limitation, bortezomib (Mackay et al., *Proceedings of the American Society for Clinical Oncology* 2004, 23, Abstract 3109), and CCI-779 (Wu et al., *Proceedings of the American Association of Cancer Research* 2004, 45, abstract 3849).

Generally, the use of cytotoxic and/or cytostatic anti-cancer agent in combination with a compound or composition of the present invention for the treatment of cancer will serve to:

(1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

EXAMPLES

Abbreviations used in this specification are as follows:

| | |
|---|---|
| HPLC | high pressure liquid chromatography |
| MS | mass spectrometry |
| ES | electrospray |
| DMSO | dimethylsulfoxide |
| MP | melting point |
| NMR | nuclear resonance spectroscopy |
| TLC | thin layer chromatography |
| rt | room temperature |

Preparation of 4-amino-3-fluorophenol

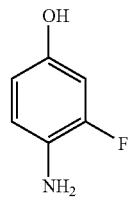

To a dry flask purged with Argon was added 10% Pd/C (80 mg) followed by 3-fluoro-4-nitrophenol (1.2 g, 7.64 mmol) as a solution in ethyl acetate (40 mL). The mixture was stirred under an $H_2$ atmosphere for 4 h. The mixture was filtered through a pad of Celite and the solvent was evaporated under reduced pressure to afford the desired product as a tan solid (940 mg, 7.39 mmol; 97% yield); $^1$H-NMR (DMSO-$d_6$) 4.38 (s, 2H), 6.29-6.35 (m, 1H), 6.41 (dd, J=2.5, 12.7, 1H), 6.52-6.62 (m, 1H), 8.76 (s, 1H).

Preparation of 4-(4-amino-3-fluorophenoxy)pyridine-2-carboxylic acid methylamide

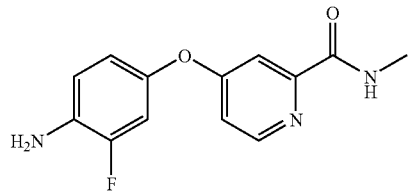 [SMILES: CNC(=O)c1cc(Oc2ccc(N)c(F)c2)ccn1]

A solution of 4-amino-3-fluorophenol (500 mg, 3.9 mmol) in N,N-dimethylacetamide (6 mL) cooled to 0° C. was treated with potassium tert-butoxide (441 mg, 3.9 mmol), and the brown solution was allowed to stir at 0° C. for 25 min. To the mixture was added 4-chloro-N-methyl-2-pyridinecarboxamide (516 mg, 3.0 mmol) as a solution in dimethylacetamide (4 mL). The reaction was heated at 100° C. for 16 h. The mixture was cooled to room temperature, quenched with $H_2O$ (20 mL), and extracted with ehtylacetate (4×40 mL). The combined organics were washed with $H_2O$ (2×30 mL), dried ($MgSO_4$), and evaporated to afford a red-brown oil. $^1$H-NMR indicated the presence of residual dimethylacetamide, thus the oil was taken up in diethylether (50 mL) and was further washed with brine (5×30 mL). The organic layer was dried ($MgSO_4$) and concentrated to give 950 mg of the desired product as a red-brown solid, which was used in the next step without purification.

A method of preparing 4-chloro-N-methyl-2-pyridinecarboxamide is described in Bankston et al., *Org. Proc. Res. Dev.* 2002, 6(6), 777-781.

Example 1

Preparation of 4{4-[3-(4-chloro-3-trifluoromethylphenyl)-ureido]-3-fluorophenoxy}-pyridine-2-carboxylic acid methylamide

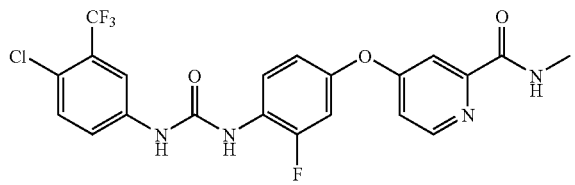 [SMILES: CNC(=O)c1cc(Oc2ccc(NC(=O)Nc3ccc(Cl)c(C(F)(F)F)c3)c(F)c2)ccn1]

To a solution of 4-(4-amino-3-fluorophenoxy)pyridine-2-carboxylic acid methylamide (177 mg, 0.68 mmol) in toluene (3 mL) was added 4-chloro-3-(trifluoromethyl)phenyl isocyanate (150 mg, 0.68 mmol). The mixture was stirred at rt for 72 h. The reaction was concentrated under reduced pressure and the residue was triturated with diethylether. The resulting solid was collected by filtration and dried in vacuo for 4 h to afford the title compound (155 mg, 0.32 mmol; 47% yield); $^1$H-NMR (DMSO-$d_6$) 2.78 (d, J=4.9, 3H), 7.03-7.08 (m, 1H), 7.16 (dd, J=2.6, 5.6, 1H), 7.32 (dd, J=2.7, 11.6, 1H), 7.39 (d, J=2.5, 1H), 7.60 (s, 2H), 8.07-8.18 (m, 2H), 8.50 (d, J=5.7, 1H), 8.72 (s, 1H), 8.74-8.80 (m, 1H), 9.50 (s, 1H); MS (HPLC/ES) 483.06 m/z=(M+1).

Example 2

Preparation of 4{4-[3-(4-chloro-3-trifluoromethylphenyl)-ureido]-3-fluorophenoxy}-pyridine-2-carboxylic acid methylamide hydrochloride The compound of example 1 as a free base (2.0 g) was dissolved in anhydrous tetrahydrofuran (15 mL) and a 4M HCl/dioxane was added (excess). The solution was then concentrated in vacuo to afford 2.32 grams of off-white solids. The crude salt was dissolved in hot ethanol (125 mL), activated carbon was added and the mixture heated at reflux for 15 minutes. The hot suspension was filtered through a pad of Celite 521 and allowed to cool to room temperature. The flask was placed in a freezer overnight. The crystalline solids were collected by suction filtration, washed with ethanol, then hexane and air-dried. The mother liquors were concentrated down and crystallization (in freezer) allowed taking place overnight. A second crop of solids was collected and combined with the first crop. The colorless salt was dried in a vacuum oven at 60° C. over two days. Yield of hydrochloride salt obtained 1.72 g (79%).
Melting point: 215° C.
Elemental analysis:

|   | Calcd. | Found |
|---|--------|-------|
| C | 48.57  | 48.68 |
| H | 3.11   | 2.76  |
| N | 10.79  | 10.60 |
| Cl| 13.65  | 13.63 |
| F | 14.63  | 14.88 |

Example 3

Preparation of 4{4-[3-(4-chloro-3-trifluoromethylphenyl)-ureido]-3-fluorophenoxy}-pyridine-2-carboxylic acid methylamide mesylate The compound of example 1 as a free base (2.25 g) was dissolved in ethanol (100 mL) and a stock solution of methanesulfonic acid (excess) was added. The solution was then concentrated in vacuo to afford a yellow oil. Ethanol was added and concentration repeated, affording 2.41 g of off-white solids. The crude salt was dissolved in hot ethanol (~125 mL) and then cooled slowly to crystallize. After reaching room temperature, the flask was placed in a freezer overnight. The colorless crystalline material was collected by suction filtration; the filter cake was washed with ethanol, then hexane and air-dried, to afford 2.05 g of material, which was dried in a vacuum oven at 60° C. overnight.
Melting point: 231° C.
Elemental analysis:

|   | Calcd. | Found |
|---|--------|-------|
| C | 45.64  | 45.34 |
| H | 3.31   | 3.08  |
| N | 9.68   | 9.44  |
| Cl| 6.12   | 6.08  |
| F | 13.13  | 13.42 |
| S | 5.54   | 5.59  |

Example 4

Preparation of 4{4-[3-(4-chloro-3-trifluoromethylphenyl)-ureido]-3-fluorophenoxy}-pyridine-2-carboxylic acid methylamide phenylsulfonate The compound of example 1 as a free base (2.25 g) was suspended in ethanol (50 mL) and benzensulfonic acid (0.737 g) in ethanol (50 mL) was added. The mixture was heated with vigorous stirring. All solid material dissolved to give a reddish solution. The solution was allowed to cool to room temperature and the flask scratched. Crystal formation was difficult to achieve, some seeds were found, added to solution and placed in freezer overnight. Grayish-tan solids had formed in the flask; the material was broken up & collected by suction filtration. The solids were washed with ethanol, then hexane and air-dried. Weighed product: 2.05 g, 69% yield.
Melting point: 213° C.
Elemental Analysis:

|   | Calcd. | Found |
|---|--------|-------|
| C | 50.59  | 50.24 |
| H | 3.30   | 3.50  |
| N | 8.74   | 8.54  |
| F | 11.86  | 11.79 |
| Cl| 5.53   | 5.63  |
| S | 5.00   | 5.16  |

Example 5 c-raf (raf-1) Biochemical Assay

The c-raf biochemical assay was performed with a c-raf enzyme that was activated (phosphorylated) by Lck kinase.

Lck-activated c-raf (Lck/c-raf) was produced in Sf9 insect cells by co-infecting cells with baculoviruses expressing, under the control of the polyhedrin promoter, GST-c-raf (from amino acid 302 to amino acid 648) and Lck (full-length). Both baculoviruses were used at the multiplicity of infection of 2.5 and the cells were harvested 48 h post infection.

MEK-1 protein was produced in Sf9 insect cells by infecting cells with the baculovirus expressing GST-MEK-1 (full-length) fusion protein at the multiplicity of infection of 5 and harvesting the cells 48 hours post infection. Similar purification procedure was used for GST-c-raf 302-648 and GST-MEK-1. Transfected cells were suspended at 100 mg of wet cell biomass per mL in a buffer containing 10 mM sodium phosphate, 140 mM sodium chloride pH 7.3, 0.5% Triton X-100 and the protease inhibitor cocktail. The cells were disrupted with Polytron homogenizer and centrifuged 30,000 g for 30 minutes. The 30,000 g supernatant was applied onto GSH-Sepharose. The resin was washed with a buffer containing 50 mM Tris, pH 8.0, 150 mM NaCl and 0.01% Triton X-100. The GST-tagged proteins were eluted with a solution containing 100 mM Glutathione, 50 mM Tris, pH 8.0, 150 mM NaCl and 0.01% Triton X-100. The purified proteins were dialyzed into a buffer containing 20 mM Tris, pH 7.5, 150 mM NaCl and 20% Glycerol.

Test compounds were serially diluted in DMSO using three-fold dilutions to stock concentrations ranging typically from 50 µM to 20 nM (final concentrations in the assay range from 1 µM to 0.4 nM). The c-Raf biochemical assay was performed as a radioactive filtermat assay in 96-well Costar polypropylene plates (Costar 3365). The plates were loaded with 75 µL solution containing 50 mM HEPES pH 7.5, 70 mM NaCl, 80 ng of Lck/c-raf and 1 µg MEK-1. Subsequently, 2 µL of the serially diluted individual compounds were added to the reaction, prior to the addition of ATP. The reaction was initiated with 25 µL ATP solution containing 5 µM ATP and 0.3 µCi [33P]-ATP. The plates were sealed and incubated at 32° C. for 1 h. The reaction was quenched with the addition of 50 µL of 4% Phosphoric Acid and harvested onto P30 filtermats (PerkinElmer) using a Wallac Tomtec Harvester. Filtermats were washed with 1% Phosphoric Acid first and deinonized $H_2O$ second. The filters were dried in a microwave, soaked in scintillation fluid and read in a Wallac 1205 Betaplate Counter (Wallac Inc., Atlanta, Ga., U.S.A.). The results were expressed as percent inhibition.

% Inhibition=$[100-(T_{ib}/T_i)] \times 100$ where $T_{ib}$=(counts per minute with inhibitor)−(background)

$T_i$=(counts per minute without inhibitor)−(background)

The compound of the present invention shows potent inhibition of raf kinase in this assay.

Example 6 p38 kinase in vitro assay

Purified and His-tagged p38 α2 (expressed in *E. Coli*) was activated in vitro by MMK-6 to a high specific activity. Using a microtiter format, all reactions were conducted in 100 µL volumes with reagents diluted to yield 0.05 µg/well of activated p38 α2 and 10 µg/well of myelin basic protein in assay buffer (25 mM HEPES 7.4, 20 mM $MgCl_2$, 150 mM NaCl). Test compounds (5 µL of a 10% DMSO solution in water) were prepared and diluted into the assay to cover a final concentration range from 5 nM to 2.5 µM. The kinase assay was initiated by addition of 25 µL of an ATP cocktail to give a final concentration of 10 µM cold ATP and 0.2 µCi [gamma-$^{33}$P] ATP per well (200-400 dpm/pmol of ATP). The plate was incubated at 32° C. for 35 min., and the reaction quenched with 7 µL of a 1 N aq HCl solution. The samples were harvested onto a P30 Filtermat (Wallac, Inc.) using a TomTec 1295 Harvester (Wallac, Inc.), and counted in a LKB 1205 Betaplate Liquid Scintillation Counter (Wallac, Inc.). Negative controls included substrate plus ATP alone. SW1353 cellular assay: SW1353 cells (human chondro-sarcoma) are seeded (1000 cells/100 µL DMEM 10% FCS/well) into 96-well plates and incubated overnight. After medium replacement, cells are exposed to test compounds for 1 h at 37° C., at which time human IL-1 (1 ng/mL, Endogen, Woburn, Wash.) and recombinant human TNFalpha (10 ng/mL) are added. Cultures are incubated for 48 h at 37° C., then supernatant IL-6 values are determined by ELISA. The compound of this invention shows significant inhibition of p38 kinase.

Example 7

Bio-Plex Phospho-ERK ½ immunoassay.

A 96 well pERK immunoassay, using laser flow cytometry (Bio-Rad) platform has been established to measure inhibition of basal pERK in breast cancer cell line. MDA-MB-231 cells were plated at 50,000 cells per well in 96 well microtitre plates in complete growth media. For effects of test compounds on basal pERK½ inhibition, the next day after plating, MDA-MB-231 cells were transferred to DMEM with 0.1% BSA and incubated with test compounds diluted 1:3 to a final concentration of 3 µM to 12 nM in 0.1% DMSO. Cells were incubated with test compounds for 2 h, washed, and lysed in Bio-Plex whole cell lysis buffer A. Samples are diluted with buffer B 1:1 (v/v) and directly transferred to assay plate or frozen at −80 C. degrees until processed. 50 µL of diluted MDA-MB-231 cell lysates were incubated with about 2000 of 5 micron Bio-Plex beads conjugated with an anti-ERK½ antibody overnight on a shaker at room temperature. The next day, biotinylated phospho-ERK½ sandwich immunoassay was performed, beads are washed 3 times during each incubation and then 50 µL of PE-strepavidin was used as a developing reagent. The relative fluorescence units of pERK½ were detected by counting 25 beads with Bio-Plex flow cell (probe) at high sensitivity. The IC50 was calculated by taking untreated cells as maximum and no cells (beads only) as background using in an Excel spreadsheet based program. The compound of this invention shows significant inhibition in this assay.

Example 8

Flk-1 (murine VEGFR-2) Biochemical Assay

This assay was performed in 96-well opaque plates (Costar 3915) in the TR-FRET format. Reaction conditions are as follows: 10 µM ATP, 25 nM poly GT-biotin, 2 nM Eu-labelled phospho-Tyr Ab, 10 nM APC, 7 nM Flk-1 (kinase domain), 1% DMSO, 50 mM HEPES pH 7.5, 10 mM $MgCl_2$, 0.1 mM EDTA, 0.015% BRIJ, 0.1 mg/mL BSA, 0.1% mercapto-ethanol). Reaction is initiated upon addition of enzyme. Final reaction volume in each well is 100 µL. Plates are read at both 615 and 665 nM on a Perkin Elmer Victor V Multilabel counter at about 1.5-2.0 hours after reaction initiation. Signal is calculated as a ratio: (665 nm/615 nm)*10000 for each well. The compound of this invention shows significant inhibition of VEGFR2 kinase.

Example 9

Murine PDGFR FRET biochemical assay

This assay was formatted in a 96-well black plate (Costar 3915). The following reagents are used: Europium-labeled anti-phosphotyrosine antibody pY20 (Perand streptavidin-APC; poly GT-biotin from, and mouse PDGFR. The reaction conditions are as follows: 1 nM mouse PDGFR is combined with 20 μM ATP, 7 nM poly GT-biotin, 1 nM pY20 antibody, 5 nM streptavidin-APC, and 1% DMSO in assay buffer (50 mM HEPES pH 7.5, 10 mM $MgCl_2$, 0.1 mM EDTA, 0.015% BRIJ 35, 0.1 mg/mL BSA, 0.1% mercaptoethanol). Reaction is initiated upon addition of enzyme. Final reaction volume in each well is 100 μL. After 90 minutes, the reaction is stopped by addition of 10 μL/well of 5 μM staurosporine. Plates are read at both 615 and 665 nm on a Perkin Elmer VictorV Multilabel counter at about 1 hour after the reaction is stopped. Signal is calculated as a ratio: (665 nm/615 nm)*10000 for each well. The compound of this invention shows significant inhibition of PDGFR kinase.

For $IC_{50}$ generation for both PDGFR and Flk-1, compounds were added prior to the enzyme initiation. A 50-fold stock plate was made with compounds serially diluted 1:3 in a 50% DMSO/50% dH2O solution. A 2 μL addition of the stock to the assay gave final compound concentrations ranging from 10 μM-4.56 nM in 1% DMSO. The data were expressed as percent inhibition: % inhibition=100-((Signal with inhibitor-background)/(Signal without inhibitor-background))*100

Example 10

MDA-MB231 proliferation assay

Human breast carcinoma cells (MDA MB-231, NCI) were cultured in standard growth medium (DMEM) supplemented with 10% heat-inactivated FBS at 37° C. in 5% $CO_2$ (vol/vol) in a humidified incubator. Cells were plated at a density of 3000 cells per well in 90 μL growth medium in a 96 well culture dish. In order to determine $T_{0h}$ CTG values, 24 hours after plating, 100 μL of CellTiter-Glo Luminescent Reagent (Promega) was added to each well and incubated at room temperature for 30 minutes. Luminescence was recorded on a Wallac Victor II instrument. The CellTiter-Glo reagent results in cell lysis and generation of a luminescent signal proportional to the amount of ATP present, which, in turn is directly proportional to the number of cells present.

Test compounds are dissolved in 100% DMSO to prepare 10 mM stocks. Stocks were further diluted 1:400 in growth medium to yield working stocks of 25 μM test compound in 0.25% DMSO. Test compounds were serially diluted in growth medium containing 0.25% DMSO to maintain constant DMSO concentrations for all wells. 60 μL of diluted test compound were added to each culture well to give a final volume of 180 μL. The cells with and without individual test compounds were incubated for 72 hours at which time ATP dependent luminescence was measured, as described previously, to yield $T_{72h}$ values. Optionally, the $IC_{50}$ values can be determined with a least squares analysis program using compound concentration versus percent inhibition.

% Inhibition=[1−($T_{72h\ test}$−$T_{0h}$)/($T_{72h\ ctrl}$−$T_{0h}$)]×100, where $T_{72h\ test}$=ATP dependent luminescence at 72 hours in the presence of test compound $T_{72h\ ctrl}$=ATP dependent luminescence at 72 hours in the absence of test compound $T_{0h}$=ATP dependent luminescence at Time Zero The compound of this invention shows significant inhibition of proliferation using this assay.

Example 11 pPDGFR-beta sandwich ELISA in AoSMC cells

100K P3-P6 Aortic SMC were plated in each well of 12-well cluster in 1000 μL volume/well of SGM-2 using standard cell culture techniques. Next day, cells were rinsed with 1000 μL D-PBS once, then serum starved in 500 μL SBM (smooth muscle cell basal media) with 0.1% BSA overnight. Compounds were diluted at a dose range from (10 μM to 1 nM in 10-fold dilution steps in DMSO. Final DMSO concentration 0.1%). Remove old media by inversion into the sink quickly then add 100 μL of each dilution to corresponding well of cells for 1 h at 37° C. Cells were then stimulated with 10 ng/mL PDGF-BB ligand for 7 min at 37° C. The media is decanted and 150 μL of isotonic lysis buffer with protease inhibitor tablet (Complete; EDTA-free) and 0.2 mM Na vanadate is added. Cells are lysed for 15 min at 4° C. on shaker in cold room. Lysates are put in eppendorf tubes to which 15 μL of agarose-conjugated anti-PDGFR-beta antibody is added and incubated at 4° C. overnight. Next day, beads are rinsed in 50-volumes of PBS three times and boiled in 1×LDS sample buffer for 5 minutes. Samples were run on 3-8% gradient Tris-Acetate gels and transferred onto Nitrocellulose. Membranes were blocked in 1% BSA/TBS-T for 1 hr. before incubation in anti-phospho-PDGFR-b (Tyr-857) antibody in blocking buffer (1:1000 dilution) for 1 h. After three washes in TBS-T, membranes were incubated in Goat anti-rabbit HRP IgG (1:25000 dilution) for 1 hr. Three more washes followed before addition of ECL substrate. Membranes were exposed to Hyperfilm-ECL. Subsequently, membranes were stripped and reprobed with anti-PDGFR-beta antibody for total PDGFR-beta.

Table 1 illustrates the results of in vitro kinase biochemical assays for p38 kinase, PDGFR kinase and VEGFR2 kinase. These three kinase targets are all involved in stroma activation and endothelial cell proliferation, leading to angiogenesis, and providing blood supply to the tumor tissue.

TABLE 1

|  | mPDGFR IC50, nM | mVEGFR2 IC50, nM | p38 IC50, nM |
| --- | --- | --- | --- |
| Example 1 | 83 | 5.5 | 24 |

Table 2 illustrates the results of two cellular assays for raf kinase activity, which are (i) inhibition of pERK in MDA-MB231 cells, a mechanistic readout of raf kinase activity, and (ii) a proliferation assay of MDA-MB231 cells, a functional assay of raf kinase activity. In addition, Table 2 illustrates the results of PDGFR driven phosphorylation of PDGFR-beta in aortic smooth muscle cells, which is a mechanistic readout of PDGFR kinase inhibition.

TABLE 2

| | pERK in cells (MDA-MB-231) IC50, nM | Proliferation (MDA-MB-231) IC50, nM | pPDGFR (AoSMC) IC50, nM |
|---|---|---|---|
| Example 1 | 22 | 600 | 43.6 |

Overall, compounds of the present invention provide a unique combination of inhibition of angiogenesis and tumor cell proliferation. They also possess an improved inhibition profile against several key kinase targets such as raf, p38, PDGFR, and VEGFR-2, which are all molecular targets of interest for the treatment of osteoporosis, inflammatory diseases, and hyper-proliferative diseases, including cancer.

It is believed that one skilled in the art, using the preceding information and information available in the art, can utilize the present invention to its fullest extent. It should be apparent to one of ordinary skill in the art that changes and modifications can be made to this invention without departing from the spirit or scope of the invention as it is set forth herein. All publications, applications and patents cited above and below are incorporated herein by reference.

The topic headings set forth above and below are meant as guidance where certain information can be found in the application, but are not intended to be the only source in the application where information on such topic can be found.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding U.S. Provisional Application Ser. No. 60/489,102, filed Jul. 23, 2003 and U.S. Provisional Application Ser. No. 60/540,326 filed Feb. 2, 2004 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of Formula (I) or a pharmaceutically acceptable salt thereof, or an isolated stereoisomer of a pharmaceutically acceptable salt thereof

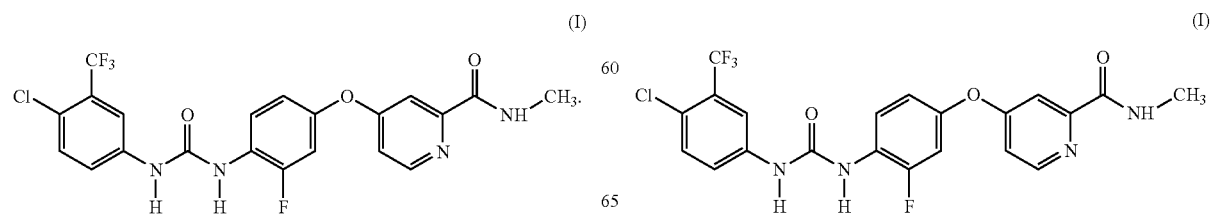

2. A pharmaceutically acceptable salt of a compound of Formula I

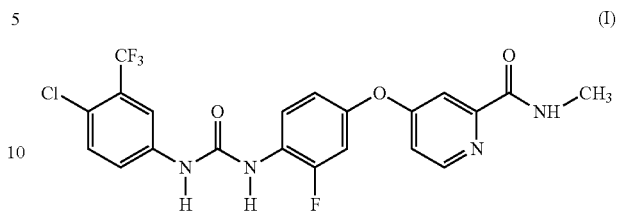

which is a basic salt of an organic acid or inorganic acid which is hydrochloric acid, hydrobromic acid, sulfuric acid, phosphoric acid, methanesulfonic acid, trifluoromethanesulfonic acid, benzenesulfonic acid, p-toluene sulfonic acid (tosylate salt), 1-napthalene sulfonic acid, 2-napthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, or mandelic acid.

3. A compound which is 4{4-[3-(4-chloro-3-trifluoromethylphenyl)-ureido]-3-fluorophenoxy}-pyridine-2-carboxylic acid methylamide, or a pharmaceutically acceptable salt thereof.

4. A pharmaceutically acceptable salt of a compound of claim 3 which is a basic salt of an organic acid or inorganic acid which is hydrochloric acid, hydrobromic acid, sulfuric acid, phosphoric acid, methanesulfonic acid, trifluoromethanesulfonic acid, benzenesulfonic acid, p-toluene sulfonic acid (tosylate salt), 1-napthalene sulfonic acid, 2-napthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, or mandelic acid.

5. A compound which is a hydrochloride, benzenesulfonate, or methanesulfonate salt of N-(4-chloro-3-(trifluoromethyl)phenyl)-N'-2-fluoro-(4-(2-(N-methylcarbamoyl)-4-pyridyloxy)phenyl) urea.

6. A pharmaceutical composition comprising a compound of claim 1 and a physiologically acceptable carrier.

7. A pharmaceutical composition comprising a compound of claim 2 and a physiologically acceptable carrier.

8. A pharmaceutical composition comprising a compound of claim 3 and a physiologically acceptable carrier.

9. A pharmaceutical composition which comprises a pharmaceutically acceptable salt of N-(4-chloro-3-(trifluoromethyl)phenyl)-N'-2-fluoro-(4-(2-(N-methylcarbamoyl)-4-pyridyloxy)phenyl) urea and a physiologically acceptable carrier.

10. A compound which is a metabolite of the compound of Formula (I) or a pharmaceutically acceptable salt thereof, or an isolated stereoisomer of a pharmaceutically acceptable salt thereof, where the metabolism site is either one of the two urea nitrogen atoms, or the pyridine nitrogen atom, or the methylamide functionality, or any combination of the above.

11. A compound of which is a metabolite of the compound of Formula (I),

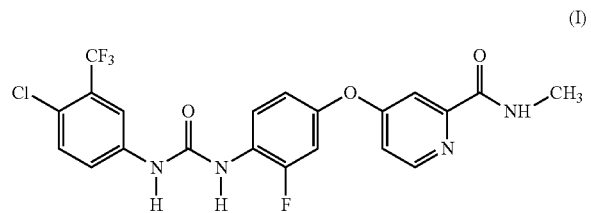 [SMILES: CNC(=O)c1cc(Oc2ccc(NC(=O)Nc3ccc(Cl)c(C(F)(F)F)c3)c(F)c2)ccn1]

(I)

where
a) either urea nitrogen atom carries a hydroxyl group, or
b) the pyridine nitrogen atom is oxidized, or
c) the amide functionality is de-methylated, or
d) the pyridine nitrogen atom is oxidized and the amide functionality is de-methylated, or
e) either urea nitrogen atom carries a hydroxyl group and the pyridine nitrogen atom is oxidized, or
f) either urea nitrogen atom carries a hydroxyl group and the amide functionality is de-methylated, or
g) either urea nitrogen atom carries a hydroxyl group and the pyridine nitrogen atom is oxidized and the amide functionality is de-methylated.

12. A compound which is:
4{4-[3-(4-chloro-3-trifluoromethylphenyl)-ureido]-3-fluorophenoxy}-pyridine-2-carboxylic acid amide,
4{4-[3-(4-chloro-3-trifluoromethylphenyl)-ureido]-3-fluorophenoxy}-1-hydroxy-pyridine-2-carboxylic acid methylamide, or
4{4-[3-(4-chloro-3-trifluoromethylphenyl)-ureido]-3-fluorophenoxy}-1-hydroxy-pyridine-2-carboxylic acid amide.

13. A compound of Formula (I)

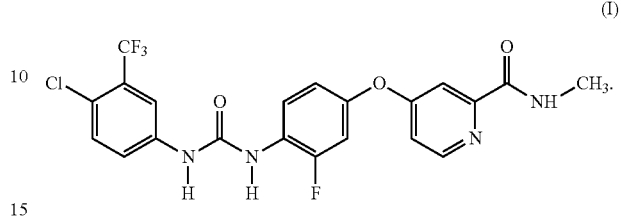

(I)

14. A pharmaceutical composition comprising the compound of claim 13 and a physiologically acceptable carrier.

15. A salt of a compound of Formula (I)

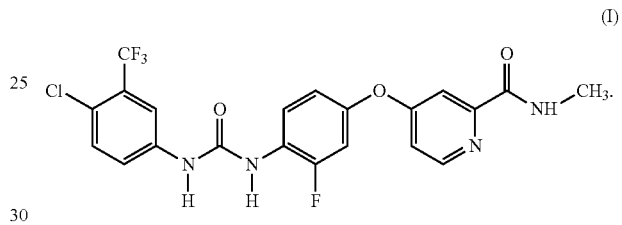

(I)

16. A pharmaceutical composition comprising a salt of claim 15 and a physiologically acceptable carrier.

* * * * *

UNITED STATES PATENT AND TRADEMARK OFFICE
CERTIFICATE OF CORRECTION

PATENT NO. : 8,637,553 B2  
APPLICATION NO. : 10/895985  
DATED : January 28, 2014  
INVENTOR(S) : Boyer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2400 days.

Signed and Sealed this
Sixteenth Day of June, 2015

Michelle K. Lee
*Director of the United States Patent and Trademark Office*